United States Patent
Takata et al.

(10) Patent No.: US 10,331,851 B2
(45) Date of Patent: Jun. 25, 2019

(54) CONTROL METHOD AND NON-TRANSITORY COMPUTER-READABLE RECORDING MEDIUM

(71) Applicant: Panasonic Corporation, Osaka (JP)

(72) Inventors: Kazutoyo Takata, Fukui (JP); Kazuki Kozuka, Fukui (JP); Kenji Kondo, Fukui (JP); Hirohiko Kimura, Fukui (JP); Toyohiko Sakai, Fukui (JP)

(73) Assignee: PANASONIC CORPORATION, Osaka (JP)

( * ) Notice: Subject to any disclaimer, the term of this patent is extended or adjusted under 35 U.S.C. 154(b) by 909 days.

(21) Appl. No.: 14/719,327

(22) Filed: May 22, 2015

(65) Prior Publication Data
US 2015/0347464 A1     Dec. 3, 2015

(30) Foreign Application Priority Data
May 29, 2014   (JP) .................. 2014-111728

(51) Int. Cl.
G06F 16/00     (2019.01)
G06F 19/00     (2018.01)
(Continued)

(52) U.S. Cl.
CPC .......... G06F 19/321 (2013.01); G06F 16/168 (2019.01); G06F 19/00 (2013.01);
(Continued)

(58) Field of Classification Search
CPC ....... A61B 5/743; A61B 5/7475; A61B 5/748; A61B 5/7435; A61B 6/461; A61B 6/462;
(Continued)

(56) References Cited

U.S. PATENT DOCUMENTS 8,150,110 B2 *   4/2012   Huo ................. G06T 5/009
                                                 382/128
2003/0013951 A1 *  1/2003   Stefanescu ........ G06F 17/30256
                                                 600/407
(Continued)

FOREIGN PATENT DOCUMENTS

JP     2004-160103     6/2004
JP     2008-257292     10/2008
(Continued)

OTHER PUBLICATIONS

Endo, Masahiro, et al. "Content-based image-retrieval system in chest computed tomography for a solitary pulmonary nodule: method and preliminary experiments." International journal of computer assisted radiology and surgery 7.2 (2012): 331-338. (Year: 2012).*

(Continued)

*Primary Examiner* — Mark D Featherstone
*Assistant Examiner* — Diedra McQuitery
(74) *Attorney, Agent, or Firm* — Wenderoth, Lind & Ponack, L.L.P.

(57) ABSTRACT

A display control unit vertically divides a case display area in accordance with the number of disease names selected by a user to create a number of sub-areas equal to the number of disease names. Each of the sub-areas is vertically elongated so that thumbnail images of similar cases of the corresponding disease name are displayed so as to be aligned in a column. The display control unit displays, in each sub-area, thumbnail images of similar cases of the corresponding disease name so that the thumbnail images are aligned in a column in order of decreasing similarity to a search query image displayed in a layout area.

21 Claims, 66 Drawing Sheets

(51) Int. Cl.
*G16H 50/00* (2018.01)
*G06F 16/16* (2019.01)
*G16H 50/70* (2018.01)
*G16H 40/60* (2018.01)
*G16H 30/40* (2018.01)
*G16H 30/00* (2018.01)
*H04N 21/4728* (2011.01)
*G06F 16/14* (2019.01)
*H04N 21/472* (2011.01)

(52) U.S. Cl.
CPC .............. *G16H 50/00* (2018.01); *G16H 50/70* (2018.01); *G06F 16/156* (2019.01); *G16H 30/00* (2018.01); *G16H 30/40* (2018.01); *G16H 40/60* (2018.01); *H04N 21/472* (2013.01); *H04N 21/4728* (2013.01)

(58) Field of Classification Search
CPC ......... A61B 6/463; A61B 6/464; A61B 6/465; A61B 6/467; A61B 6/469; A61B 6/5223; A61B 8/461; A61B 8/463; A61B 8/464; A61B 8/465; A61B 8/467; A61B 8/469; A61B 2090/364; G06F 3/048; G06F 3/0481; G06F 3/04817; G06F 3/04842; G06F 3/0484; G06F 17/30247; G06F 17/30244; G06F 19/30; G06F 19/32; G06F 19/321; G06F 19/3443; G06F 2203/04803; G06T 2207/10072; G06T 2207/20104; G06T 3/40
See application file for complete search history.

(56) References Cited

U.S. PATENT DOCUMENTS

| | | | |
|---|---|---|---|
| 2008/0243395 A1 | 10/2008 | Oosawa et al. | |
| 2009/0087049 A1* | 4/2009 | Takahashi | G16H 15/00 382/128 |
| 2010/0045800 A1* | 2/2010 | Chebil | G03B 13/36 348/169 |
| 2010/0202711 A1* | 8/2010 | Kondo | G06T 1/20 382/254 |
| 2010/0232661 A1* | 9/2010 | Hisanaga | G06F 19/321 382/128 |
| 2011/0099032 A1 | 4/2011 | Miyasa et al. | |
| 2013/0006087 A1* | 1/2013 | Kondo | G06F 19/3443 600/407 |
| 2013/0114867 A1* | 5/2013 | Kondo | G06F 19/321 382/128 |
| 2013/0253953 A1* | 9/2013 | Hisanaga | G06F 19/3443 705/3 |

FOREIGN PATENT DOCUMENTS

| | | | |
|---|---|---|---|
| JP | 2011-092286 | 5/2011 | |
| JP | 2014-004252 | 1/2014 | |
| WO | WO-2014169164 A1 * | 10/2014 | ........... G06T 7/0012 |

OTHER PUBLICATIONS

Akira Oosawa et al., "Development of "Synapse Case Match", Content-based Image Retrieval System for Supporting Image Diagnosis" Fujifilm Research&Development, No. 58, 2013, pp. 11-14.

* cited by examiner

FIG. 8

| DISEASE LIST | | |
|---|---|---|
| MYCOSIS | 14 | 731 |
|   ASPERGILLOSIS | 8 | 732 |
|   CRYPTOCOCCOSIS | 6 | 733 |
| NEOPLASTIC | 13 | 734 |
|   LUNG CANCER | 10 | 735 |
|   METASTATIC LUNG CANCER | 3 | 736 |
| NONNEOPLASTIC | 6 | 737 |
|   LUNG ABSCESS | 4 | 738 |
|   SARCOIDOSIS | 1 | 739 |
|   SEPTIC EMBOLI | 1 | 740 |
| MYCOBACTERIOSIS | 6 | 741 |
|   NONTUBERCULOUS MYCOBACTERIA (NTM) | 4 | 742 |
|   TUBERCULOSIS | 2 | 743 |
| OTHER | 2 | 744 |
|   BRONCHIECTASIS | 1 | 745 |
|   ... | 1 | |

DISTRIBUTIONS OF LESIONS ~750
- ☐ DIFFUSE ─751
- ▦ SEGMENTAL ─752
- ☐ BRONCHIAL ─753
- ☐ BILATERAL ─754
- ☐ MULTIPLE ─755
- ▦ SUBPLEURAL ─756
- ☐ HEMATOGENOUS ─757

FIG. 12

DISTRIBUTIONS OF LESIONS ~750
- ☐ DIFFUSE ─751
- ▦ SEGMENTAL ─752
- ☑ BRONCHIAL ─753
- ☐ BILATERAL ─754
- ☐ MULTIPLE ─755
- ▦ SUBPLEURAL ─756
- ☐ HEMATOGENOUS ─757

FIG. 14

DISTRIBUTIONS OF LESIONS ⸺750
- ☑ DIFFUSE ⸺751
- ▨ SEGMENTAL ⸺752
- ☐ BRONCHIAL ⸺753
- ☐ BILATERAL ⸺754
- ☐ MULTIPLE ⸺755
- ▨ SUBPLEURAL ⸺756
- ☑ HEMATOGENOUS ⸺757

FIG. 16
1000

| 1100 | PATIENT ID | 123456 |
|---|---|---|
| 1200 | NAME | JOHN DOE |
| 1300 | AGE | 28 |
| 1400 | GENDER | MALE |
| 1500 | PAST MEDICAL HISTORY | NO |
| 1600 | FAMILY HISTORY | NO |
| 1700 | CHIEF COMPLAINT | COUGH |
| 1800 | TEST INFORMATION | (SEE FIG. 17) |
| 1900 | DEFINITE DIAGNOSIS | MYCOPLASMA PNEUMONIAE |

FIG. 17
1800

| 1810 | TEST ID | 13227895 |
|---|---|---|
| 1820 | TEST DATE | 10:00 AM FEBRUARY 5, 20XX |
| 1830 | TEST TYPE | BLOOD TEST |
| 1840 | TEST RESULT | YYYY1 |

| TEST ID | 13227903 |
|---|---|
| TEST DATE | 11:00 AM FEBRUARY 5, 20XX |
| TEST TYPE | SIMPLE X-RAY (CHEST) |
| TEST RESULT | YYYY2 |

| TEST ID | 13227989 |
|---|---|
| TEST DATE | 9:00 AM FEBRUARY 9, 20XX |
| TEST TYPE | CT (CHEST) |
| TEST RESULT | YYYY3 |

| 1810 | TEST ID | 13227989 |
|---|---|---|
| 3100 | FINDINGS | MULTIPLE NODULES OF 0.5 TO 1.0 cm IN THE RIGHT LUNG FIELD WERE ... |
| 3200 | DIAGNOSIS | INFLAMMATORY NODULES OR TUBERCULOSIS IS SUSPECTED. |

FIG. 23

| PATIENT ID | PATIENT NAME | TEST DATE | TEST ID | TEST TYPE |
|---|---|---|---|---|
| 443982 | RICHARD ROE | DEC 1, 20XX | 23982874 | MR (HEAD) |
| 123456 | JOHN DOE | MAY 8, 20XX | 13227989 | CT (CHEST) |
| 345455 | ... | ... | ... | ... |
| 235982 | ... | ... | ... | ... |

800

| SERIES ID | DEFINITION | IMAGE |
|---|---|---|
|  |  |  |
|  |  |  |
|  |  |  |

| PATIENT ID | PATIENT NAME | TEST DATE | TEST ID | TEST TYPE |
|---|---|---|---|---|
| 443982 | RICHARD ROE | DEC 1, 20XX | 23982874 | MR (HEAD) |
| 123456 | JOHN DOE | MAY 8, 20XX | 13227989 | CT (CHEST) |
| 345455 | ... | ... | ... | ... |
| 235982 | ... | ... | ... | ... |

800

| SERIES ID | DEFINITION | IMAGE |
|---|---|---|
| CT152729 | PULMONARY CONDITION SLICE THICKNESS: 5 mm | |
| CT152730 | PULMONARY CONDITION SLICE THICKNESS: 1 mm | |
| CT152731 | MEDIASTINAL CONDITION SLICE THICKNESS: 5 mm | |

| DISEASE ID | MAJOR-CATEGORY DISEASE NAME | SUBCATEGORY DISEASE NAME | NUMBER OF RESULTS | SIMILAR CASE ID |
|---|---|---|---|---|
| DIS528 | NEOPLASTIC | LUNG CANCER | 10 | SIM258, SIM551, SIM1209, SIM2341, ... |
| DIS922 | MYCOSIS | ASPERGILLOSIS | 8 | ... |
| ... | MYCOSIS | CRYPTOCOCCOSIS | 6 | ... |
| ... | NONNEOPLASTIC | LUNG ABSCESS | 4 | ... |
| ... | MYCOBACTERIOSIS | NONTUBERCULOUS MYCOBACTERIA (NTM) | 4 | ... |
| ... | ... | ... | ... | ... |

FIG. 30

| DISEASE LIST | 730 |
|---|---|
| LUNG CANCER | 10 |
| ASPERGILLOSIS | 8 |
| CRYPTOCOCCOSIS | 6 |
| LUNG ABSCESS | 4 |
| NONTUBERCULOUS MYCOBACTERIA (NTM) | 4 |
| METASTATIC LUNG CANCER | 3 |
| TUBERCULOSIS | 2 |
| INFLAMMATORY NODULES | 1 |
| SEPTIC EMBOLI | 1 |
| BRONCHIECTASIS | 1 |
| UNKNOWN | 1 |

FIG. 31

| DISEASE LIST | 730 |
|---|---|
| MYCOSIS | 14 |
| NEOPLASTIC | 13 |
| NONNEOPLASTIC | 6 |
| MYCOBACTERIOSIS | 6 |
| OTHER | 2 |

FIG. 32

| DISEASE LIST | 730 |
|---|---|
| MYCOSIS | 14 |
|   ASPERGILLOSIS | 8 |
|   CRYPTOCOCCOSIS | 6 |
| NEOPLASTIC | 13 |
|   LUNG CANCER | 10 |
|   METASTATIC LUNG CANCER | 3 |
| NONNEOPLASTIC | 6 |
|   LUNG ABSCESS | 4 |
|   SARCOIDOSIS | 1 |
|   SEPTIC EMBOLI | 1 |
| MYCOBACTERIOSIS | 6 |
|   NONTUBERCULOUS MYCOBACTERIA (NTM) | 4 |
|   TUBERCULOSIS | 2 |
| OTHER | 2 |
|   BRONCHIECTASIS | 1 |
|   ... | 1 |

FIG. 34

| NAME OF DISTRIBUTION | NUMBER OF CASES | SIMILAR CASE ID |
|---|---|---|
| DIFFUSE | 3 | SIM2521, SIM4123, SIM5225 |
| SEGMENTAL | 0 | NO CASE |
| BRONCHIAL | 2 | SIM0006, SIM1892, SIM4399 |
| BILATERAL | 12 | ・・・ |
| MULTIPLE | 22 | ・・・ |
| SUBPLEURAL | 0 | NO CASE |
| HEMATOGENOUS | 5 | ・・・ |

FIG. 35
4410

| NUMBER OF ROWS | 2 |
|---|---|
| NUMBER OF COLUMNS | 2 |

~4411

| POSITION | SLICE ID |
|---|---|
| FIRST ROW AND FIRST COLUMN | CT12353515 |
| FIRST ROW AND SECOND COLUMN | — |
| SECOND ROW AND FIRST COLUMN | — |
| SECOND ROW AND SECOND COLUMN | — |

| | | |
|---|---|---|
| 4100 | SIMILAR CASE ID | SIM5232 |
| 4200 | SLICE ID | CT149391025 |
| 4300 | REGION-OF-INTEREST INFORMATION | xl, yt, xr, yb |
| 4400 | IMAGE FEATURE DATA | f1, f2, f3, ..., fN |
| 4500 | THUMBNAIL IMAGE DATA | $(I_{0,0}, I_{0,1}, ..., I_{w-1, h-1})$ |
| 4600 | DISTRIBUTION-OF-LESION INFORMATION | |
| 4700 | DEFINITE DIAGNOSIS (MAJOR-CATEGORY DISEASE NAME) | NEOPLASTIC |
| 4800 | DEFINITE DIAGNOSIS (SUBCATEGORY DISEASE NAME) | LUNG CANCER |
| 4900 | PLEURAL AREA INFORMATION | xpl, ypt, xpr, ypb |

| | | |
|---|---|---|
| 4610 | DIFFUSE | 1 |
| 4620 | SEGMENTAL | 0 |
| 4630 | BRONCHIAL | 0 |
| 4640 | BILATERAL | 1 |
| 4650 | MULTIPLE | 1 |
| 4660 | SUBPLEURAL | 0 |
| 4670 | HEMATOGENOUS | 1 |

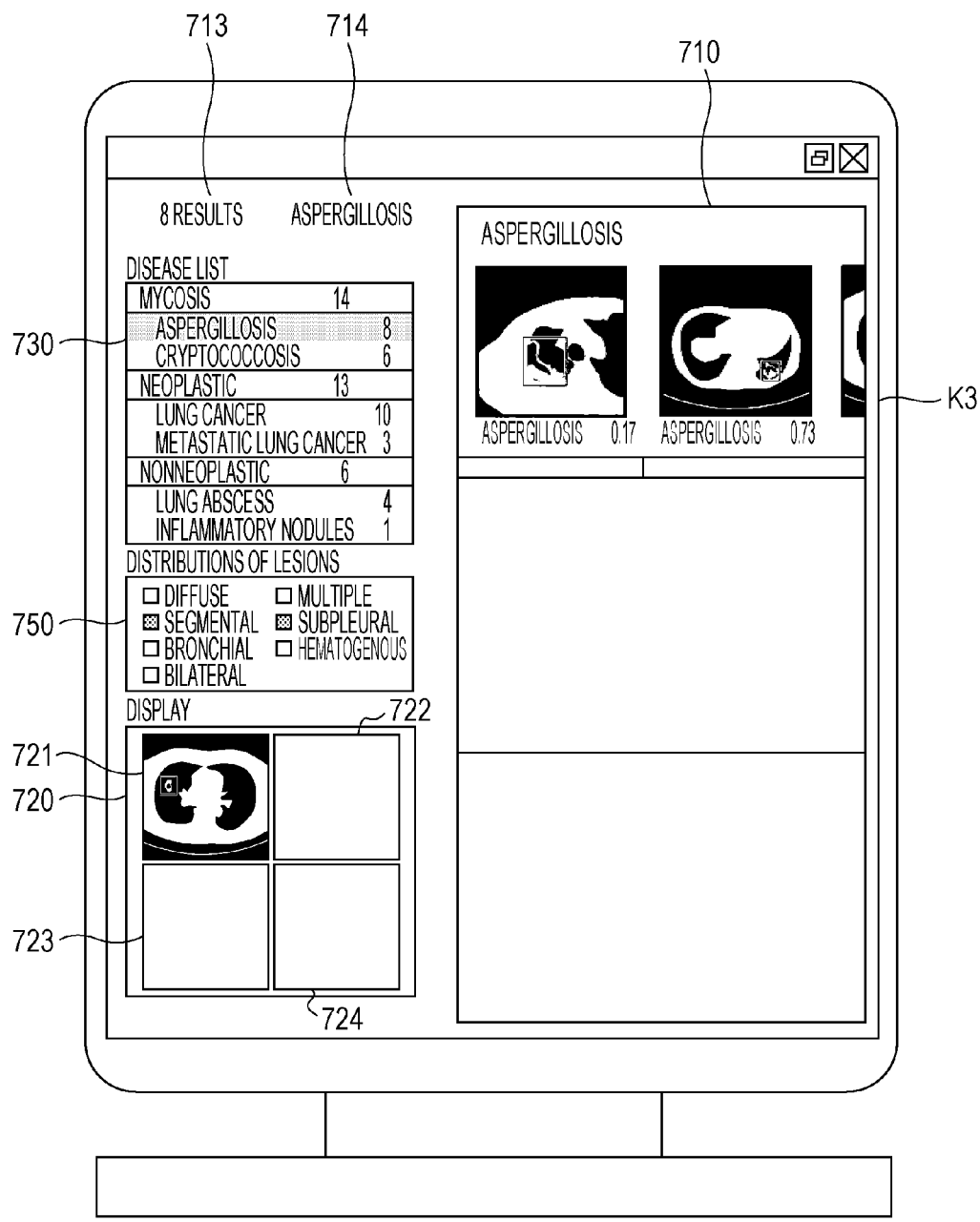

CONTROL METHOD AND NON-TRANSITORY COMPUTER-READABLE RECORDING MEDIUM

BACKGROUND

1. Technical Field

The present disclosure relates to a control method for controlling an information terminal for searching for similar medical images that are similar to a medical image to be interpreted, and to a non-transitory computer-readable recording medium.

2. Description of the Related Art

Medical imaging devices such as computed tomography (CT) and magnetic resonance imaging (MRI) devices have been developed and used widely in recent years. The advent of CT, MRI, and the like has enabled acquisition of a large number of high-definition digital medical images. Medical images interpreted by physicians are sequentially accumulated together with interpretation reports in a picture archiving and communication system (PACS). For instance, as disclosed in Japanese Unexamined Patent Application Publication No. 2008-257292, a technique for image retrieval has been being developed. In this technique, previous medical images that are similar to a medical image to be interpreted are searched for in the records of previous clinical cases accumulated in the PACS for the reference of new interpretation.

However, further improvements have been needed.

SUMMARY

One non-limiting and exemplary embodiment provides a further improvement.

In one general aspect, the techniques disclosed here feature a control method for controlling an information terminal for access to a case search system that searches for a medical image with reference to a medical image database having medical images registered therein. The information terminal includes a display and a computer, and a target medical image is displayed on the display, the target medical image being a medical image that is a target to be interpreted and that is selected from among candidates for image interpretation. The control method includes causing the computer of the information terminal to detect first designation information indicating a region of interest in the target medical image; causing the computer of the information terminal to receive from the case search system, in accordance with the region of interest indicated by the first designation information, a plurality of similar medical images each having a feature value having a predetermined similarity to a feature value of the region of interest; causing the computer of the information terminal to display a display screen including a first display area and a second display area, the first display area being used to display the target medical image, the second display area being an area in which a certain number of images among the plurality of similar medical images are displayed so as to be arranged horizontally in order of decreasing similarity to the target medical image, the display screen further including a third display area used to select a disease name; and causing the computer of the information terminal to, in response to selection of a plurality of disease names using the third display area, select disease-associated similar medical images corresponding to each of the selected plurality of disease names from among the plurality of similar medical images, and to display the selected disease-associated similar medical images in the second display area so that the selected disease-associated similar medical images are classified by each of the selected plurality of disease names and are arranged vertically in a corresponding one of sub-areas in order of decreasing similarity to the target medical image.

In an aspect of the present disclosure, a further improvement may be achievable.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 8 is an enlarged view of a disease list display area;

FIG. 11 is an enlarged view of a distribution list display area;

FIG. 12 is a diagram illustrating the distribution list display area in which a checkbox is checked;

FIG. 14 is a diagram illustrating the distribution list display area in which a plurality of checkboxes are checked;

FIG. 16 is a diagram illustrating the data configuration of patient information;

FIG. 17 is a diagram illustrating the data configuration of test information registered in the patient information illustrated in FIG. 16;

FIG. 19 is a diagram illustrating the data configuration of a diagnostic report;

FIG. 23 is a view of a test list screen;

FIG. 24 is a view of the test list screen obtained after a test is selected;

FIG. 29 is a diagram illustrating the data configuration of a disease list generated in S1300 in FIG. 27;

FIG. 30 is a diagram illustrating a first example display of the disease list display area;

FIG. 31 is a diagram illustrating a second example display of the disease list display area;

FIG. 32 is a diagram illustrating a third example display of the disease list display area;

FIG. 34 is a diagram illustrating the data configuration of the distribution list generated in S1400 in FIG. 27;

FIG. 35 is a diagram illustrating the data configuration of display box management information;

FIG. 46 is a diagram illustrating the data configuration of similar case data that additionally includes pleural area information;

FIG. 69 is a diagram illustrating a basic screen obtained after aspergillosis is selected in the disease list display area illustrated in FIG. 63.

DETAILED DESCRIPTION

Underlying Knowledge of Present Disclosure

Figure 1:
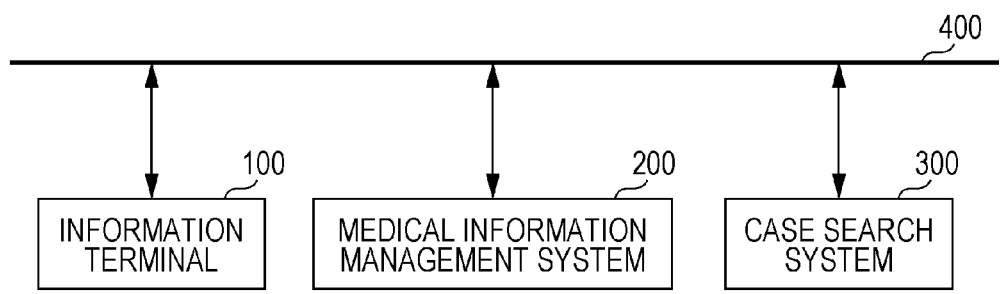
FIG. 1 is an overall configuration diagram of a hospital information system in which an information terminal according to embodiments of the present disclosure is used.

First, a description will be given of issues pertaining to an aspect of the present disclosure.

Japanese Unexamined Patent Application Publication No. 2008-257292 (hereinafter referred to as "Patent Literature 1") discloses an image-based diagnosis supporting apparatus that presents images of clinical cases which are useful for judging a disease or disorder (hereinafter referred to simply as a "disease") or presents statistical information and the like on the disease for image-based diagnosis which is based on an image to be used for diagnosis (hereinafter referred to as a "diagnostic image"). The image-based diagnosis supporting apparatus displays a search result screen which shows the diagnostic image and information on typical cases of individual diseases. Specifically, the search result screen shows (i) images of typical cases of the top three ranked diseases A, D, and G, (ii) similarities to the diagnostic image, the numbers of registered cases, and the numbers of typical cases for the individual diseases, (iii) the number of search results (or the total number of diseases found as a result of the search), and (iv) a "next page" soft button or the like for accessing information on the other diseases not shown on the current screen (see paragraphs [0062] to [0063] and FIG. 6(E) in Patent Literature 1).

When a disease of a patient is judged based on a diagnostic image, the name of the disease may not have been specified. In this case, it may be better to judge the disease by viewing a wide variety of images of clinical cases (hereinafter also referred to as "case images") having high similarity to the diagnostic image, instead of classifying case images obtained as a result of the search for each disease name in advance, than to diagnose the disease by initially viewing images illustrating typical cases of individual diseases. In Patent Literature 1, images of typical cases are displayed for each disease name in order of similarity on an initial screen for search results (see FIG. 6(E) in Patent Literature 1). In Patent Literature 1, therefore, the name of the disease of the patient is specified from a collection of disease names corresponding to typical cases selected in advance. That is, a physician is allowed to diagnose the disease within a range of limited selection options given on the initial screen. In this case, the physician may fail to accurately judge the disease. Observation of a wide variety of case images in the initial stage, on the other hand, may not necessarily enable the physician to efficiently or accurately specify the name of the disease of the patient, since the number of case images obtained as a result of the search may be very large, for example, two to three hundred.

OOSAWA et al. discloses, in "Development of 'SYN-APSE Case Match', Content-based Image Retrieval System for Supporting Image Diagnosis", FUJIFILM RESEARCH & DEVELOPMENT, FUJIFILM Corporation, Mar. 27, 2013, No. 58, pp. 11-14 (hereinafter referred to as "Non-Patent Literature 1"), a similar-case search system that uses a function to search for previous similar cases by using the image of a lesion to immediately extract and present exact information based on clinical knowledge accumulated in the PACS described above or the like to assist the physician in image-based diagnosis. Specifically, in the disclosed system, a plurality of case images having a feature similar to that of a lesion in a test image are searched for and displayed in order of similarity. Then, one reference case image is selected from among the plurality of displayed case images and is displayed along with the test image (Section 2.2, "System Features", on page 12 and FIG. 3 in Non-Patent Literature 1).

Even when, as in Non-Patent Literature 1, case images that show lesions similar to a lesion in a test image are displayed in order of similarity, the following issues may occur: The number of case images obtained as a result of the search may be very large, for example, two to three hundred. In addition, case images corresponding to a disease displayed in the test image in order of similarity as a result of the search made by the system may not necessarily appear in an actual clinical setting. Accordingly, merely displaying case images in order of similarity according to the results of the search made by the system may not be sufficient for the physician to efficiently or accurately specify the name of the disease of the patient. As described above, Non-Patent Literature 1 discloses that, even if the number of case images obtained as a result of the search is very large, the case images are merely displayed in order of similarity. Thus, Non-Patent Literature 1 experiences some difficulty in the process through which a large number of case images obtained as a result of the search are narrowed down or refined to efficiently or accurately specify the name of the disease of the patient.

In the examination of a lesion appearing in a medical image to be interpreted for which a disease name has not been specified, it is considered effective to refer to medical images similar to the medical image to be interpreted among other medical images for which disease names have been specified. When such a system is established, however, a large number of medical images are registered in the medical image database described above. In this case, it is still desirable to effectively provide the physician with similar medical images to be referenced for diagnosis using the medical image to be interpreted.

In light of the foregoing discussion, the following aspects are provided.

A first aspect of the present disclosure provides a control method for controlling an information terminal for access to a case search system that searches for a medical image with reference to a medical image database having medical images registered therein. The information terminal includes a display and a computer, and a target medical image is displayed on the display, the target medical image being a medical image that is a target to be interpreted and that is selected from among candidates for image interpretation. The control method includes causing the computer of the information terminal to detect first designation information indicating a region of interest in the target medical image; causing the computer of the information terminal to receive from the case search system, in accordance with the region of interest indicated by the first designation information, a plurality of similar medical images each having a feature value having a predetermined similarity to a feature value of the region of interest; causing the computer of the information terminal to display a display screen including a first display area and a second display area, the first display area being used to display the target medical image, the second display area being an area in which a certain number of images among the plurality of similar medical images are displayed so as to be arranged horizontally in order of decreasing similarity to the target medical image, the display screen further including a third display area used to select a disease name; and causing the computer of the information terminal to, in response to selection of a plurality of disease names using the third display area, select disease-associated similar medical images corresponding to each of the selected plurality of disease names from among the plurality of similar medical images, and to display the selected disease-associated similar medical images in the second display area so that the selected disease-associated similar medical images are classified by each of the selected plurality of disease names and are arranged vertically in a corresponding one of sub-areas in order of decreasing similarity to the target medical image.

According to this aspect, first, the plurality of similar medical images are displayed so as to be arranged horizontally in order of decreasing similarity to the target medical image. That is, before reference images are refined according to the relationship with the target medical image, as large a number of similar medical images as possible are displayed in the second display area with a limited number of images displayable, in accordance with the relationship with the target medical image in terms of similarity regardless of the disease name. Then, the similar medical images are displayed so as to be arranged horizontally in order of decreasing similarity to the target medical image. Accordingly, similar medical images with high similarity to the target medical image are collected in an upper portion of the second display area.

Then, after the similar medical images are refined by selecting one or more disease names, the similar medical images are classified according to each of the selected disease names. Thus, the name of a disease of a lesion appearing in the target medical image can be specified by comparing and referencing the similar medical images for each disease name, resulting in efficient improvement in comparison accuracy. Then, the similar medical images are displayed in the second display area so as to be arranged vertically in order of decreasing similarity to the target medical image. Accordingly, similar medical images with high similarity to the target medical image are collected in an upper portion of the second display area across the selected disease names.

Thus, even before reference images are refined according to the relationship with the target medical image or after the similar medical images are refined by selecting one or more disease names, similar medical images with high similarity to the target medical image are collected in an upper portion of the second display area.

Thus, even before reference images are refined according to the relationship with the target medical image or after the similar medical images are refined by selecting one or more disease names, the physician may be able to give priority to the study of similar medical images with high similarity to the target medical image by using a similar area (e.g., an upper portion) in the second display area.

Accordingly, providing a system with efficiently improved comparison accuracy may contribute to an improvement in medical treatment accuracy.

A second aspect of the present disclosure provides a control method for controlling an information terminal for access to a case search system that searches for a medical image with reference to a medical image database having medical images registered therein. The information terminal includes a display and a computer, and a target medical image is displayed on the display, the target medical image being a medical image that is a target to be interpreted and that is selected from among candidates for image interpretation. The control method includes causing the computer of the information terminal to detect first designation information indicating a region of interest in the target medical image; causing the computer of the information terminal to receive from the case search system, in accordance with the region of interest indicated by the first designation information, a plurality of similar medical images each having a feature value having a predetermined similarity to a feature value of the region of interest; causing the computer of the information terminal to display a display screen including a first display area and a second display area, the first display area being used to display the target medical image, the second display area being an area in which a certain number of images among the plurality of similar medical images are displayed so as to be arranged horizontally in order of decreasing similarity to the target medical image, the display screen further including a third display area used to select a disease name; and causing the computer of the information terminal to, in response to selection of a plurality of disease names using the third display area, select disease-associated similar medical images corresponding to each of the selected plurality of disease names from among the plurality of similar medical images, and to display the selected disease-associated similar medical images in the second display area so that the selected disease-associated similar medical images are classified by each of the selected plurality of disease names and are arranged horizontally in a corresponding one of sub-areas in order of decreasing similarity to the target medical image. A similar medical image having highest similarity to the target medical image among the similar medical images displayed in the second display area is displayed at a position that is closest to the first display area.

According to this aspect, first, the plurality of similar medical images are displayed in order of decreasing similarity to the target medical image. That is, before reference images are refined according to the relationship with the target medical image, as large a number of similar medical images as possible are displayed in the second display area with a limited number of images displayable, in accordance with the relationship with the target medical image in terms of similarity regardless of the disease name. Then, the similar medical images are displayed so as to be arranged horizontally in order of decreasing similarity to the target medical image. Accordingly, similar medical images with high similarity to the target medical image are collected in an upper portion of the second display area.

Then, after the similar medical images are refined by selecting one or more disease names, the similar medical images are classified according to each of the selected disease names. Thus, the name of a disease of a lesion appearing in the target medical image can be specified by comparing and referencing the similar medical images for each disease name, resulting in efficient improvement in comparison accuracy. Then, the similar medical images are displayed in the second display area so as to be arranged horizontally in order of decreasing similarity to the target medical image. In this aspect, furthermore, a similar medical image with highest similarity to the target medical image among the similar medical images displayed in the second display area is displayed at the closest position to the first display area. Accordingly, even in a case where the similar medical images are displayed in the second display area so as to be arranged horizontally, similar medical images with high similarity to the target medical image are collected to a location close to the first display area across the selected disease names.

Refining similar medical images by selecting one or more disease names refers to guiding the physician to a process for comparing the target medical image displayed in the first display area with the similar medical images displayed in the second display area. According to this aspect, after the similar medical images are refined by selecting one or more disease names, the first display area and the second display area are displayed on the display screen so that the disease-associated similar medical image with the highest similarity to the target medical image, which is classified and displayed, is located at the closest position to the first display area.

Accordingly, providing a system with efficiently improved comparison accuracy may contribute to an improvement in medical treatment accuracy.

In the first aspect or the second aspect, for example, the computer of the information terminal may be caused to, in response to selection of a single disease name using the third display area, display disease-associated similar medical images corresponding to the selected single disease name in the second display area so that the disease-associated similar medical images are arranged horizontally in order of decreasing similarity to the target medical image.

Alternatively, in the first aspect or the second aspect, for example, the computer of the information terminal may be caused to, in response to selection of a single disease name using the third display area, display disease-associated similar medical images corresponding to the selected single disease name in the second display area so that the disease-associated similar medical images are arranged vertically in order of decreasing similarity to the target medical image.

Further, in the first aspect or the second aspect, for example, the target medical image may have attached information that does not include disease information, and the received plurality of similar medical images may have attached information that includes disease information.

In some cases, examination may be made to specify the name of a disease displayed in the target medical image through, before the name of the disease for a lesion in the target medical image is specified, comparison between a similar medical image in which a disease name has already been specified and the target medical image. In this aspect, displaying the target medical image, in which a disease name has not been specified, in the first display area and displaying a similar medical image in which a disease name has been specified in the second display area may enable efficient comparison between the target medical image and the similar medical image to efficiently specify the name of the disease displayed in the target medical image. Providing a system that achieves the feature described above may contribute to an improvement in medical treatment accuracy.

Further, in the first aspect or the second aspect, for example, the computer of the information terminal may be caused to, in response to detection of an instruction to display a disease-associated similar medical image in a sub-area among the sub-areas in enlarged form, enlarge the disease-associated similar medical images included in the sub-area with respect to corresponding regions in the disease-associated similar medical images, which correspond to the region of interest, in such a manner that display sizes of display frames within which the disease-associated similar medical images are displayed are maintained to be equal to each other.

In this aspect, the computer of the information terminal is caused to, in response to detection of an instruction to display a disease-associated similar medical image in a sub-area among the sub-areas in enlarged form, enlarge the disease-associated similar medical images included in the sub-area with respect to corresponding regions in the disease-associated similar medical images, which correspond to the region of interest, in such a manner that display sizes of display frames within which the disease-associated similar medical images are displayed are maintained to be equal to each other.

With the configuration described above, in accordance with an instruction to display a disease-associated similar medical image in enlarged form within a sub-area among the sub-areas, the disease-associated similar medical images within the range corresponding to the sub-area are enlarged. This eliminates the need for the user to give an instruction to enlarge each of the disease-associated similar medical images corresponding to the sub-area, leading to an improvement in operational efficiency.

In addition, in a case where the disease-associated similar medical images within the range corresponding to the sub-area are enlarged, the display sizes of display frames within which the disease-associated similar medical images are displayed are maintained to be equal to each other. Accordingly, while the disease-associated similar medical images corresponding to the sub-area are enlarged, a display with a limited number of images displayable may be efficiently used to display the disease-associated similar medical images corresponding to the sub-area in enlarged form.

In addition, the disease-associated similar medical images are enlarged with respect to corresponding regions thereof which correspond to the region of interest. Accordingly, each of the disease-associated similar medical images is enlarged with respect to a region in which the physician takes an interest within the disease-associated similar medical image.

In addition, if the total number of similar medical images is very large, it will not be efficient to simply compare every similar medical image with the target medical image. In this aspect, the similar medical images are classified according to a disease name. In this aspect, additionally, images within one of the sub-areas are selectively enlarged. Accordingly, even if the total number of similar medical images is very large, the physician may be able to concentrate their attention on images corresponding to a disease name in which the physician takes an interest among the disease-associated similar medical images classified according to a disease name. This may enable the physician to more efficiently select necessary information on the display screen while displaying the similar medical images according to each of a plurality of disease names.

Accordingly, it may be possible to, while efficiently using the display area of the display, enlarge each of the disease-associated similar medical images with respect to a region in which the physician takes an interest in accordance with a single instruction. As a result, for example, even if the number of medical images similar to the target medical image is very large, similar medical images to be referenced for the diagnosis of the target medical image are effectively selected, which may contribute to an improvement in medical treatment decision made by the physician.

In addition, in the first aspect or the second aspect, for example, each of the received plurality of similar medical images may include second designation information indicating a corresponding region thereof which corresponds to the region of interest. The computer of the information terminal may be caused to, in the enlarging of the disease-associated similar medical images with respect to the corresponding regions in the disease-associated similar medical images, which correspond to the region of interest, enlarge the disease-associated similar medical images in accordance with a size of the corresponding regions indicated by the second designation information.

In some cases, a plurality of similar medical images may have different corresponding regions thereof which correspond to the region of interest for the following reasons. For example, lesions in individual similar medical images may have different sizes, and, furthermore, different physicians gave regions corresponding to the region of interest.

If a corresponding region of each of the plurality of similar medical images, which corresponds to the region of interest, is enlarged at a certain rate common to the plurality of similar medical images, the following issue may occur: A similar medical image having a comparatively small corresponding region which corresponds to the region of interest is enlarged so that the corresponding region which corresponds to the region of interest is enlarged to be comparatively small, whereas a similar medical image having a comparatively large corresponding region which corresponds to the region of interest is enlarged so that the corresponding region which corresponds to the region of interest is enlarged to be comparatively large. That is, when the plurality of similar medical images are enlarged, the sizes of the enlarged corresponding regions which correspond to the region of interest may not be uniform, resulting in a reduction in the efficiency of comparison with the target medical image.

According to this aspect, in enlarging of each of the plurality of similar medical images with respect to the corresponding region thereof which corresponds to the region of interest, each of the plurality of similar medical images is enlarged in accordance with the size of the corresponding regions thereof which correspond to the region of interest, which is indicated by the second designation information.

With the configuration described above, the variation in the size of the enlarged corresponding regions which correspond to the region of interest when the plurality of similar medical images are enlarged may be made to fall within a certain range for the plurality of similar medical images.

Accordingly, the physician may be able to observe the enlarged corresponding regions of the plurality of similar medical images, which correspond to the region of interest, with substantially similar sizes. This may prevent the occurrence of an oversight caused by the way in which the corresponding regions of some similar medical images, which correspond to the region of interest, have been enlarged but are still so small, leading to an improvement in diagnosis accuracy.

In addition, in the first aspect or the second aspect, for example, the computer of the information terminal may be caused to enlarge the disease-associated similar medical images so that, in a case where the size of the corresponding regions indicated by the second designation information is equal to a first size, the corresponding regions are enlarged a larger amount than in a case where the size of the corresponding regions indicated by the second designation information is equal to a second size larger than the first size.

According to this aspect, the variation in the size of the enlarged corresponding regions which correspond to the region of interest when the plurality of similar medical images are enlarged may be made to fall within a certain range for the plurality of similar medical images. Specifically, in a similar medical image having a comparatively small corresponding region which corresponds to the region of interest, the corresponding region which corresponds to the region of interest is enlarged to be comparatively large, whereas, in a similar medical image having a comparatively large corresponding region which corresponds to the region of interest, the corresponding region which corresponds to the region of interest is enlarged to be comparatively small. This may allow the enlarged corresponding region which corresponds to the region of interest to fall in a similar range to some extent, regardless of the size of the corresponding region which corresponds to the region of interest.

Accordingly, the physician may be able to observe the enlarged corresponding regions of the plurality of similar medical images, which correspond to the region of interest, with substantially similar sizes. This may prevent the occurrence of an oversight caused by the way in which the corresponding regions of some similar medical images, which correspond to the region of interest, have been enlarged but are still so small, which may contribute to an improvement in diagnosis accuracy.

Alternatively, in the first aspect or the second aspect, for example, each of the received plurality of similar medical images may include second designation information indicating a corresponding region thereof which corresponds to the region of interest. The computer of the information terminal may be caused to, in enlarging of each of the plurality of similar medical images with respect to the corresponding region in the similar medical image, which corresponds to the region of interest, enlarge each of the plurality of similar medical images with an enlargement factor that makes a size of the corresponding region indicated by the second designation information have a certain ratio to the display size of the display frame within which each of the plurality of similar medical images is displayed.

In some cases, a plurality of similar medical images may have different corresponding regions thereof which correspond to the region of interest for the following reasons. For example, lesions in individual similar medical images may have different sizes, and, furthermore, different physicians gave regions corresponding to the region of interest.

If a corresponding region of each of the plurality of similar medical images, which corresponds to the region of interest, is enlarged at a certain rate, the following issue may occur: A similar medical image having a comparatively small corresponding region which corresponds to the region of interest is enlarged so that the corresponding region which corresponds to the region of interest is enlarged to be comparatively small, whereas a similar medical image having a comparatively large corresponding region which corresponds to the region of interest is enlarged so that the corresponding region which corresponds to the region of interest is enlarged to be comparatively large. That is, when the plurality of similar medical images are enlarged, the sizes of the enlarged corresponding regions which correspond to the region of interest may not be uniform, resulting in a reduction in the efficiency of comparison with the target medical image.

According to this aspect, in enlarging of each of the plurality of similar medical images with respect to the corresponding region thereof which corresponds to the region of interest, each of the plurality of similar medical images is enlarged with an enlargement factor that makes a size of the corresponding region thereof which corresponds to the region of interest, which is indicated by the second designation information, have a certain ratio to the display size of the display frame within which each of the plurality of similar medical images is displayed.

With the configuration described above, the size of the enlarged corresponding regions which correspond to the region of interest when the plurality of similar medical images are enlarged may be made substantially uniform in view of the relationship with the display size of each display frame.

Accordingly, the physician may be able to observe the enlarged corresponding regions of the plurality of similar medical images, which correspond to the region of interest, with substantially similar sizes. This may prevent the occurrence of an oversight caused by the way in which the corresponding regions of some similar medical images, which correspond to the region of interest, have been enlarged but are still so small, which may contribute to an improvement in diagnosis accuracy.

Further, in the first aspect or the second aspect, for example, the control method may further include causing the computer of the information terminal to transmit information indicating the feature value of the region of interest to the case search system; and causing the computer of the information terminal to receive from the case search system a similar medical image having a feature value having the predetermined similarity to the feature value of the region of interest.

Further, in the first aspect or the second aspect, for example, the control method may further include causing the computer of the information terminal to transmit the target medical image and the first designation information indicating the region of interest to the case search system; and causing the computer of the information terminal to receive from the case search system a similar medical image having a feature value having the predetermined similarity to the feature value of the region of interest, which is obtained from the target medical image and the first designation information.

Further, in the first aspect or the second aspect, for example, the target medical image may be a medical image of a lung, and the similar medical image may be a medical image of a lung. The first display image may include first distribution information for selection of a similar medical image that belongs to a predetermined first range indicating that a corresponding region of the similar medical image, which corresponds to the region of interest, is a large area of a lung; second distribution information for selection of a similar medical image that belongs to a predetermined second range lower than the first range, the second range indicating that a corresponding region of the similar medical image, which corresponds to the region of interest, is a portion of a lung; and third distribution information for selection of a similar medical image in which a corresponding region which corresponds to the region of interest includes a pleura. The computer of the information terminal may be caused to, in response to selection of distribution information among the first distribution information, the second distribution information, and the third distribution information, select a similar medical image corresponding to the selected distribution information from among the plurality of similar medical images and to display the selected similar medical image in the second display area.

According to this aspect, the plurality of similar medical images displayed in the second display area are classified according to the distribution type of the corresponding regions thereof which corresponds to the region of interest. This may enable efficient selection of, for example, a similar medical image similar to the region of interest included in the target medical image in terms of symptom among a large number of displayed similar medical images.

In addition, in the first aspect or the second aspect, for example, the computer of the information terminal may be caused to, in response to selection of the first distribution information, display a similar medical image corresponding to the first distribution information among the plurality of similar medical images in a display frame with an initial display size; in response to selection of the second distribution information, display a similar medical image corresponding to the second distribution information in a display frame in such a manner that the similar medical image is enlarged with respect to a corresponding region thereof which corresponds to the region of interest; and, in response to selection of the third distribution information, display a similar medical image corresponding to the third distribution information in a display frame in such a manner that the similar medical image is enlarged with respect to a corresponding region thereof which corresponds to the region of interest and in such a manner that the corresponding region includes the pleura.

According to this aspect, when similar medical images are classified according to the distribution type of the region corresponding to the region of interest, the similar medical images are displayed in accordance with the distribution type, in addition to being classified. This may enable the operator to classify the similar medical images in accordance with the distribution type of the region corresponding to the region of interest, and may eliminate the need for further operations such as enlarging the similar medical images in accordance with the distribution type or centering the region corresponding to the region of interest. Accordingly, after classification according to the distribution type of the region corresponding to the region of interest, the complexity of repeated similar operations of each of a large number of classified similar medical images may be significantly reduced. This results in a significant reduction in the risk of physician's thoughts or physician's concentration on medical treatment decision being interrupted by such complexity operations, helping the physician maintain their thoughts or concentration on medical treatment decision. The accuracy of medical treatment decision may be improved.

Further, in the first aspect or the second aspect, for example, the first distribution information may be information indicating a distribution that belongs to a bilateral category, a multiple category, a diffuse category, or a hematogenous category. The second distribution information may be information indicating a distribution that belongs to a segmental category or a bronchial category. The third distribution information may be information indicating a distribution that belongs to a subpleural category.

According to this aspect, similar medical images of a distribution that belongs to the bilateral, multiple, diffuse, or hematogenous category are displayed with an initial display size, similar medical images of a distribution that belongs to the segmental or bronchial category are displayed in enlarged form, and similar medical images of a distribution that belongs to the subpleural category are displayed in enlarged form in such a manner that a pleura is included.

For a distribution that belongs to the bilateral, multiple, diffuse, or hematogenous category, the lesion may occupy the entire lung or the lesion may occupy a large area of the lung. Thus, there is a medical need to display the similar medical images in the initial display size or without enlarging them. On the other hand, for a distribution that belongs to the segmental or bronchial category, the above possibility is less likely to occur. Thus, selecting a distribution that belongs to the segmental or bronchial category to display the similar medical images of the selected distribution in enlarged form can remove the step for enlarged display, preventing the physician's concentration from being interrupted. For a distribution that belongs to the subpleural category, the positional relationship between the pleura and the lesion is an important index for diagnosis. Thus, there is a medical need to display a similar medical image of this distribution in enlarged form so as to include the pleura.

A third aspect of the present disclosure provides a control method for controlling an information terminal for access to a case search system that searches for a medical image with reference to a medical image database having medical images registered therein. The information terminal includes a display and a computer, and a target medical image is displayed on the display, the target medical image being a medical image that is a target to be interpreted and that is selected from among candidates for image interpretation. The control method includes causing the computer of the information terminal to detect first designation information indicating a region of interest in the target medical image; causing the computer of the information terminal to receive from the case search system, in accordance with the region of interest indicated by the first designation information, a plurality of similar medical images each having a feature value having a predetermined similarity to a feature value of the region of interest; causing the computer of the information terminal to display a display screen including a first display area and a second display area, the first display area being used to display the target medical image, the second display area being an area in which a certain number of images among the plurality of similar medical images are displayed so as to be arranged vertically in order of decreasing similarity to the target medical image, the display screen further including a third display area used to select a disease name; and causing the computer of the information terminal to, in response to selection of a plurality of disease names using the third display area, select disease-associated similar medical images corresponding to each of the selected plurality of disease names from among the plurality of similar medical images, and to display the selected disease-associated similar medical images in the second display area so that the selected disease-associated similar medical images are classified by each of the selected plurality of disease names and are arranged horizontally in a corresponding one of sub-areas in order of decreasing similarity to the target medical image. A similar medical image having highest similarity to the target medical image among the similar medical images displayed in the second display area is displayed at a position that is closest to the first display area.

According to this aspect, first, the plurality of similar medical images are displayed so as to be arranged horizontally in order of decreasing similarity to the target medical image. That is, before reference images are refined according to the relationship with the target medical image, as large a number of similar medical images as possible are displayed in the second display area with a limited number of images displayable, in accordance with the relationship with the target medical image in terms of similarity regardless of the disease name. Then, the similar medical images are displayed so as to be arranged horizontally in order of decreasing similarity to the target medical image. Accordingly, similar medical images with high similarity to the target medical image are collected in an upper portion of the second display area.

Then, after the similar medical images are refined by selecting one or more disease names, the similar medical images are classified according to each of the selected disease names. Thus, the name of a disease of a lesion appearing in the target medical image can be specified by comparing and referencing the similar medical images for each disease name, resulting in efficient improvement in comparison accuracy. Then, the similar medical images are displayed in the second display area so as to be arranged vertically in order of decreasing similarity to the target medical image. Accordingly, similar medical images with high similarity to the target medical image are collected in an upper portion of the second display area across the selected disease names.

Thus, even before reference images are refined according to the relationship with the target medical image or after the similar medical images are refined by selecting one or more disease names, similar medical images with high similarity to the target medical image are collected in an upper portion of the second display area.

Thus, even before reference images are refined according to the relationship with the target medical image or after the similar medical images are refined by selecting one or more disease names, the physician may be able to give priority to the study of similar medical images with high similarity to the target medical image by using a similar area (e.g., an upper portion) in the second display area.

In this aspect, furthermore, a similar medical image with highest similarity to the target medical image among the similar medical images displayed in the second display area is displayed at the closest position to the first display area. Accordingly, similar medical images with high similarity to the target medical image are collected to a location close to the first display area across the selected disease names.

Refining similar medical images by selecting one or more disease names refers to guiding the physician to a process for comparing the target medical image displayed in the first display area with the similar medical images displayed in the second display area. According to this aspect, after the similar medical images are refined by selecting one or more disease names, the first display area and the second display area are displayed on the display screen so that the disease-associated similar medical image with the highest similarity to the target medical image, which is classified and displayed, is located at the closest position to the first display area.

Accordingly, providing a system with efficiently improved comparison accuracy may contribute to an improvement in medical treatment accuracy.

First Embodiment

An embodiment of the present disclosure will now be described hereinafter with reference to the drawings. In the drawings, the same or similar components are represented by the same numerals. In a first embodiment, search results are displayed on a landscape display, by way of example.

FIG. 1 is an overall configuration diagram of a hospital information system in which an information terminal according to this embodiment is used. As illustrated in FIG. 1, the hospital information system includes an information terminal 100, a medical information management system 200, and a case search system 300.

The information terminal 100, the medical information management system 200, and the case search system 300 are connected to one another via a network 400 so as to be capable of communicating with one another.

The medical information management system 200 and the case search system 300 may not necessarily be located in the hospital, and may be implemented by software operating on a data center, a private cloud server, a public cloud server, or the like located outside the hospital. In a case where the medical information management system 200 and the case search system 300 are located in the hospital, the network 400 may be a local area network (LAN). Examples of a LAN include wired LANs specified by the Institute of Electrical and Electronics Engineers (IEEE) 802.3 series standards, wireless LANs specified by the IEEE 802.11 series standards, and networks including both such wired and wireless LANs. In a case where the medical information management system 200 and the case search system 300 are implemented by using a server located outside the hospital, the network 400 may be the Internet.

The information terminal 100 may be a personal computer or an information terminal such as a tablet terminal. The medical information management system 200 may be a picture archiving and communication system (PACS), an electronic medical record system, or the like.

Figure 2:
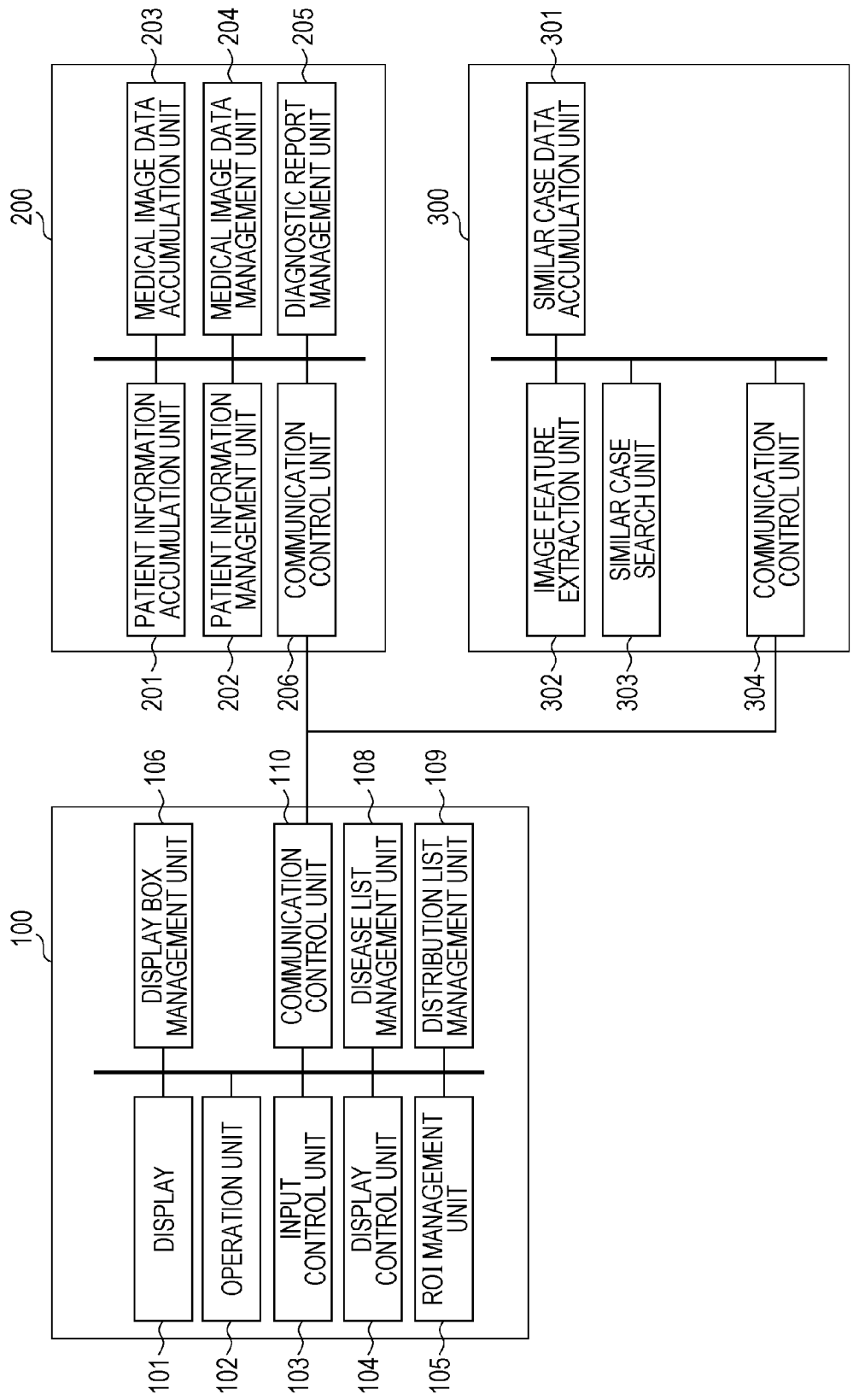
FIG. 2 is a block diagram illustrating the configuration of the information terminal, a medical information management system, and a case search system.

FIG. 2 is a block diagram illustrating the configuration of the information terminal 100, the medical information management system 200, and the case search system 300. As illustrated in FIG. 2, the information terminal 100 includes a display 101, an operation unit 102, an input control unit 103, a display control unit 104, a region of interest (ROI) management unit 105, a display box management unit 106, a disease list management unit 108, a distribution list management unit 109, and a communication control unit 110.

The display 101 may be, for example, a liquid crystal monitor for displaying a medical chart image and a medical image to be used for diagnosis, and also displaying a report entry image or the like in which the results of diagnosis are entered. While image-based diagnosis requires at least one display 101, two to three displays 101 are typically used for image-based diagnosis. In this embodiment, two displays 101 are used, one of which is a display 101*a* (an example of a second display), and the other of which is a display 101*b* (an example of a first display) (see FIG. 3).

Figure 3:
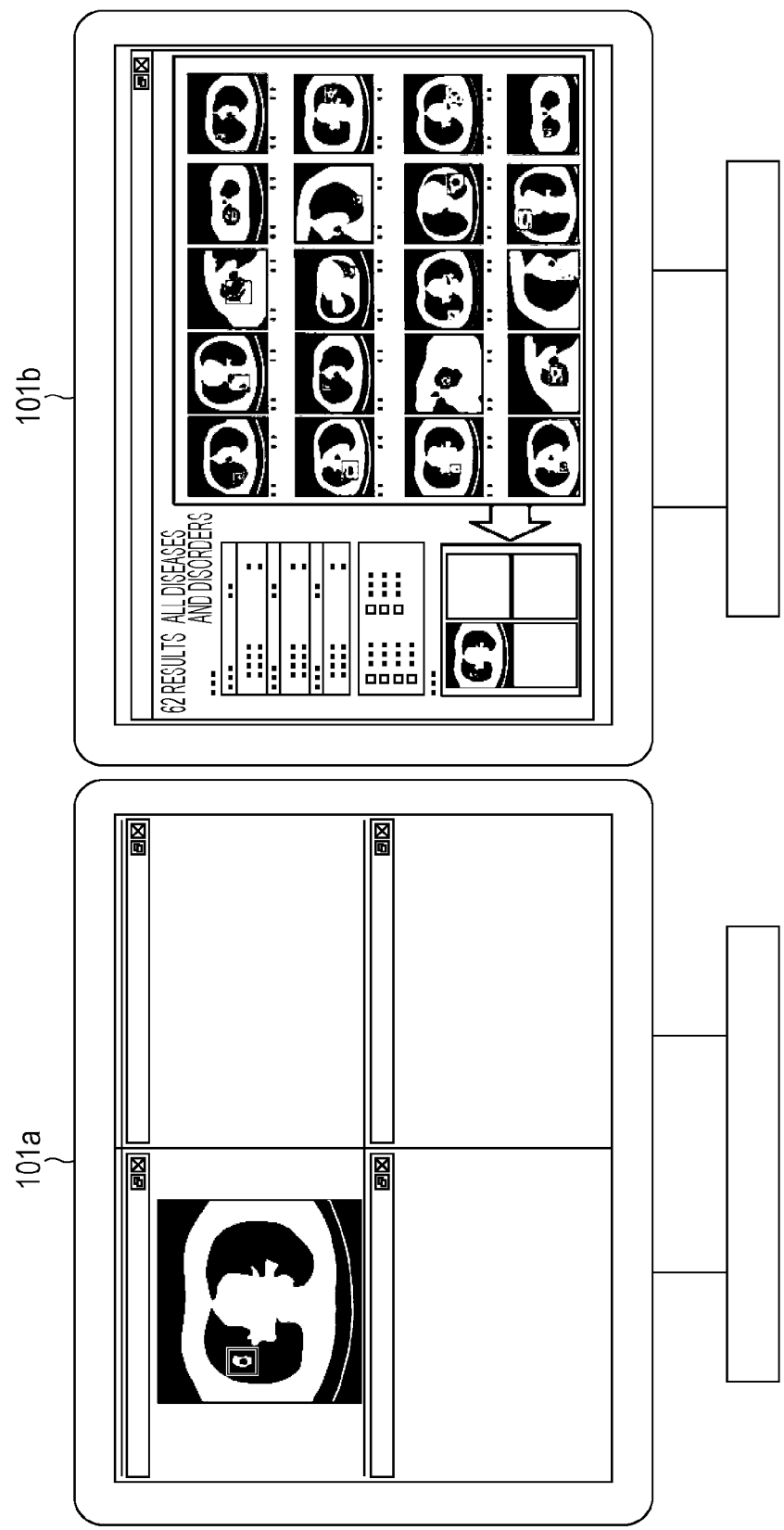
FIG. 3 illustrates external views of two displays.

Further, a display screen of the display 101*a* is an example of a second display screen, and a display screen of the display 101*b* is an example of a first display screen. FIG. 3 illustrates external views of the two displays 101*a* and 101*b*. In FIG. 3, four medical image viewers arranged in a grid of two rows and two columns are displayed on the display 101*a*, and a screen for the case search system 300 is displayed on the display 101*b*. In a case where a single display 101 is used, the first display screen and the second display screen are displayed in separate areas on the display screen of the single display 101.

The operation unit 102 includes, for example, a keyboard and a mouse, and accepts a variety of operations input by a user on the information terminal 100. For example, the operation unit 102 accepts operations such as an operation performed by the user on a medical image or medical chart image displayed on the display 101, and an operation for entering the results of diagnosis in a report input screen.

Upon detection of a user's operation on the operation unit 102, the input control unit 103 interprets the operation, and notifies the other components of the content of the operation. For example, the input control unit 103 detects the position of the mouse pointer on the display 101 by using coordinate data output from the mouse serving as the operation unit 102, and causes the mouse pointer to be displayed on the display 101. If a graphical user interface (GUI) component (e.g., a GUI button) generated by the display control unit 104 is displayed at the display position of the mouse pointer when a click of the mouse is detected, the input control unit 103 determines that the user has selected the GUI component, and notifies the other components that the GUI component has been selected by the user.

The display control unit 104 generates a GUI of the information terminal 100, and displays the GUI on the display 101.

The ROI management unit 105 generates region-of-interest information indicating a region of interest (ROI) set in a search query image described below for a similar case search, and stores the region-of-interest information in a memory to manage the region-of-interest information.

The display box management unit 106 stores display box management information 4410 described below (FIG. 35) in the memory to manage the display box management information 4410.

The disease list management unit 108 generates a disease list (FIG. 29) that is a list of diseases corresponding to similar cases displayed in a case display area 710 (FIG. 6), and stores the disease list in the memory to manage the disease list.

The distribution list management unit 109 generates a distribution list (FIG. 34) that is a list of distributions of lesions of the similar cases displayed in the case display area 710, and stores the distribution list in the memory to manage the distribution list.

The communication control unit 110 includes, for example, a communication device for connecting the information terminal 100 to the network 400, and controls communication between the information terminal 100 and the medical information management system 200 and communication between the information terminal 100 and the case search system 300. Further, the communication control unit 110 accepts from other blocks a request for transmitting a variety of types of data, and transmits data to the medical information management system 200 or the case search system 300. In addition, the communication control unit 110 receives data transmitted from the medical information management system 200 or the case search system 300, and passes the data to the corresponding block.

As illustrated in FIG. 2, the medical information management system 200 includes a patient information accumulation unit 201, a patient information management unit 202, a medical image data accumulation unit 203, a medical image data management unit 204, a diagnostic report management unit 205, and a communication control unit 206.

The patient information accumulation unit 201 accumulates patient information 1000 (FIG. 16) in which personal information such as the gender and age of a patient, clinical information such as the past medical history that the patient has, and test information on medical tests that the patient has undergone, such as a blood test, are registered.

The patient information management unit 202 performs processes, such as a process for registering data input by a user in the patient information 1000 (FIG. 16) accumulated in the patient information accumulation unit 201 to update the patient information 1000, and a process for outputting the patient information 1000 to the display control unit 104, to manage the patient information 1000. The medical image data accumulation unit 203 accumulates medical image data representing test images of the patient.

The medical image data management unit 204 stores the medical image data in the medical image data accumulation unit 203 to manage the medical image data.

The diagnostic report management unit 205 manages a diagnostic report 3000 (FIG. 19) which shows the results of the diagnosis made by the physician based on the results of tests given to the patient.

The communication control unit 206 includes, for example, a communication device for connecting the medical information management system 200 to the network 400. The communication control unit 206 accepts from other blocks a request for transmitting a variety of types of data, and transmits data to the information terminal 100 or the case search system 300. In addition, the communication control unit 206 receives data transmitted from the information terminal 100 or the case search system 300, and passes the data to the corresponding block.

As illustrated in FIG. 2, the case search system 300 includes a similar case data accumulation unit 301, an image feature extraction unit 302, a similar case search unit 303, and a communication control unit 304.

The similar case data accumulation unit 301 accumulates similar case data 4000 (FIG. 20) in which image features extracted from a large number of similar cases selected as target data for a similar case search from among similar cases managed in advance in the medical information management system 200, generated thumbnail images, and the like are registered.

The image feature extraction unit 302 extracts an image feature in region-of-interest information on the search query image transmitted from the communication control unit 110 of the information terminal 100. The region-of-interest information is an example of first designation information indicating a region of interest.

The similar case search unit 303 compares the image feature extracted by the image feature extraction unit 302 with each of image features in one or more similar cases accumulated in the similar case data accumulation unit 301, and generates similar case search results.

The communication control unit 304 includes, for example, a communication device for connecting the case search system 300 to the network 400. The communication control unit 304 accepts from other blocks a request for transmitting a variety of types of data, and transmits data to the information terminal 100 or the medical information management system 200. In addition, the communication control unit 304 receives data transmitted the information terminal 100 or the medical information management system 200, and passes the data to the corresponding block.

Figure 4:
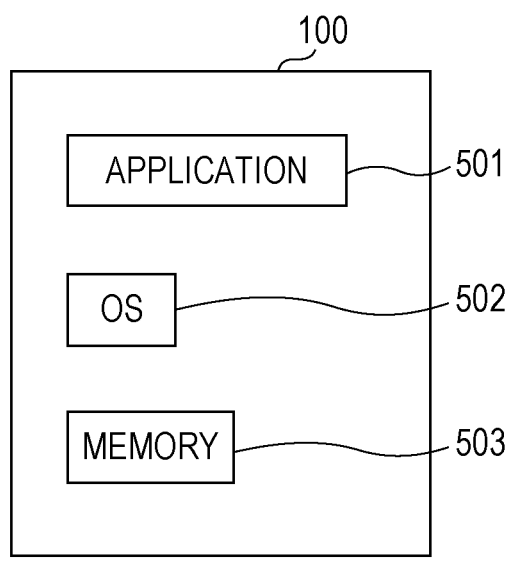
FIG. 4 is a diagram illustrating an example configuration of an implementation of the information terminal.

FIG. 4 is a diagram illustrating an example configuration of an implementation of the information terminal 100. As illustrated in FIG. 4, the information terminal 100 includes an application 501, an operating system (OS) 502, a memory 503, and other hardware (not illustrated).

The application 501 is application software for causing a personal computer or a tablet terminal to function as the information terminal 100, and is executed by a processor of the information terminal 100. The information terminal 100 may implement the application 501 by reading the application 501 from a computer-readable recording medium, or may implement the application 501 by downloading the application 501 from a network.

The application 501 includes a medical information management application and a similar case search application. The medical information management application is an application for allowing the information terminal 100 to operate in coordination with the medical information management system 200, and the similar case search application is an application for allowing the information terminal 100 to operate in coordination with the case search system 300.

The medical information management application and the similar case search application transmit and receive data to and from each other so that services provided by the medical information management system 200 and the case search system 300 are integrated in the information terminal 100.

The OS 502 is basic software of the information terminal 100, and is executed by a processor of the information terminal 100. The memory 503 includes storage devices such as a random access memory (RAM) and a read-only memory (ROM), which are included in the information terminal 100, and stores data sets included in the application 501.

The processor of the information terminal 100 executes the application 501 to implement the functions of the input control unit 103, the display control unit 104, the ROI management unit 105, the display box management unit 106, the disease list management unit 108, the distribution list management unit 109, and the communication control unit 110, which are illustrated in FIG. 2.

In this embodiment, the information terminal 100 may be implemented by the application 501, or may be implemented by the application 501 and the OS 502. Alternatively, the information terminal 100 may be implemented by the application 501, the OS 502, and the memory 503, or may be implemented by the application 501, the OS 502, the memory 503, and any other hardware (not illustrated). The information terminal 100 according to this embodiment is achievable through any of the implementations described above.

Figure 5:
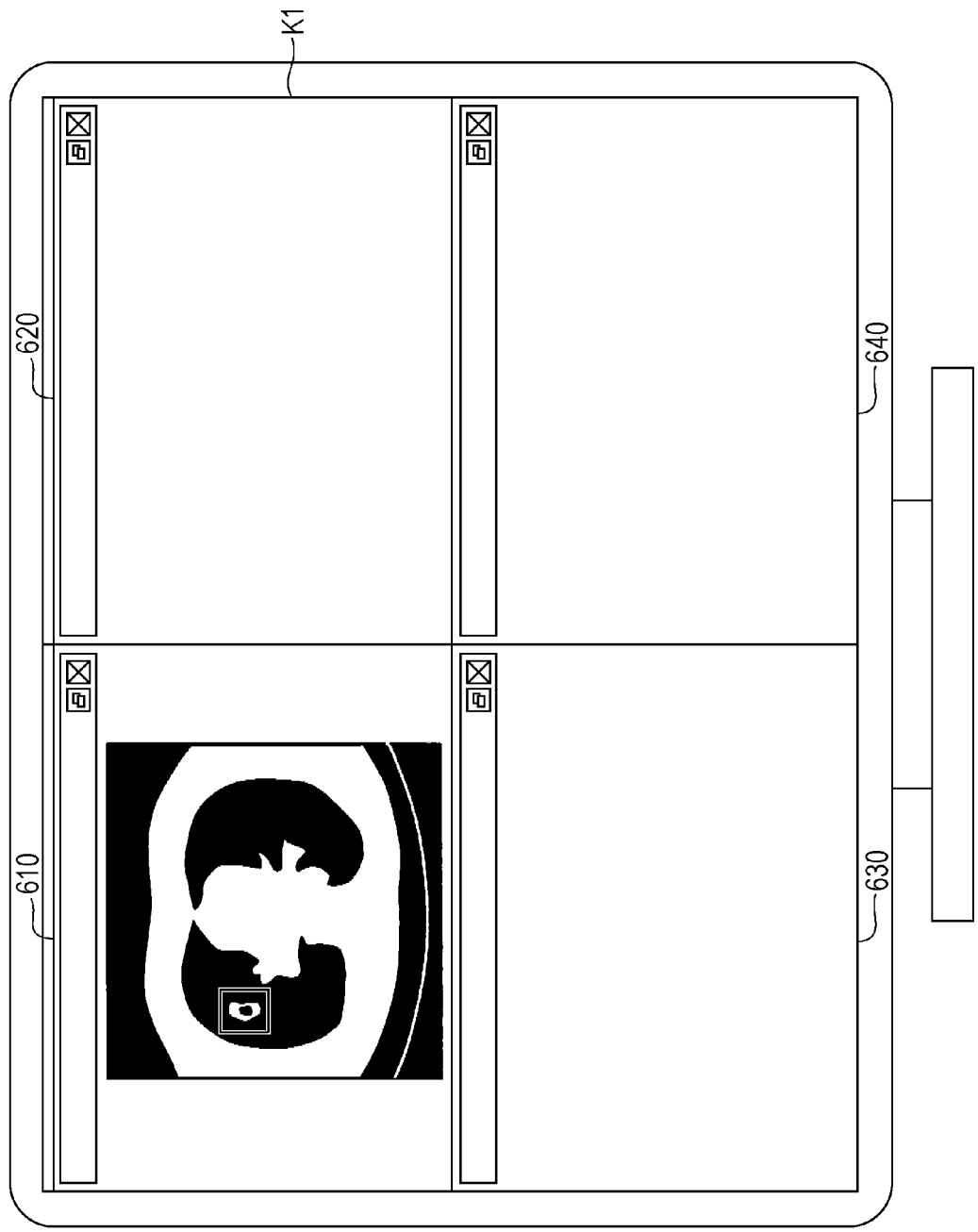
FIG. 5 is a diagram illustrating an example of a basic screen displayed on a display immediately after a similar case search application is started on the information terminal.

FIG. 5 is a diagram illustrating an example of a basic screen K1 displayed on the display 101a immediately after the similar case search application is started on the information terminal 100. The basic screen K1 illustrated in FIG. 5 includes four medical image viewers 610 to 640. Typical medical images are recorded in Digital Imaging and Communication in Medicine (DICOM) format, and the medical image viewers 610 to 640 are DICOM-compatible viewers. The medical images as used in this embodiment are chest CT images constituted by a large number of tomographic images (hereinafter referred to as "slice images") in DICOM format. This is merely an example, and CT images of any other body part (e.g., the head, abdomen, legs, or arms) may be used.

Each of the chest CT images displayed in the medical image viewers 610 to 640 is switched from one slice image to another through an operation with the mouse or keyboard. The slice images constituting the chest CT images are arranged in order from, for example, the neck toward the abdomen.

For example, when the input control unit 103 detects a rotation of the mouse wheel while the mouse pointer is on the medical image viewer 610, the display control unit 104 switches the slice image currently displayed in the medical image viewer 610 in accordance with the amount of rotation which is detected. For example, when the mouse wheel is rotated rearward (or toward the user of the mouse) by an amount corresponding to one click while the mouse is in the medical image viewer 610, the display control unit 104 switches the currently displayed slice image to the slice image corresponding to the next slice position. For example, when the mouse wheel is rotated forward (or away from the user of the mouse) by an amount corresponding to one click while the mouse is in the medical image viewer 610, the display control unit 104 switches the currently displayed slice image to the slice image corresponding to the preceding slice position. Accordingly, the user, such as a physician, retrieves the desired slice image while rotating the mouse wheel forward or rearward to appropriately switch between slice images to be displayed in the medical image viewer 610.

In place of chest CT images, magnetic resonance imaging (MRI) images or simple X-ray images may be used as medical images. Furthermore, four medical image viewers are used in the example illustrated in FIG. 5. This is merely an example, and a different number of medical image viewers, such as six or eight medical image viewers, may be used. As the number of medical image viewers used increases, the number of images to be simultaneously compared also increases whilst the display area per image decreases. Accordingly, the number of medical image viewers may be made variable, as desired, in accordance with the display size of the display 101*a*. By way of example, the number of medical image viewers may be changed, as desired, by the user or an administrator.

Before the similar case search application is started, a slice image of a chest CT image of a certain patient is displayed in the entire area of the display 101*a*. When the similar case search application is started by the user such as a radiologist in this situation, the slice image being displayed in the entire area of the display 101*a* is displayed in the medical image viewer 610.

That is, a search query image being displayed in the entire area of the display 101*a* when the user starts the similar case search application is initially displayed in the medical image viewer 610. The display control unit 104 may superimpose the region of interest (ROI) of the target to be subjected to a similar case search on a search query image for display. The search query image is an example of a target medical image that is a medical image to be interpreted.

In FIG. 5, no images are displayed in the medical image viewers 620 to 640. If there are a plurality of test images of a patient to be diagnosed and a plurality of test images are displayed on the display 101*a* before the similar case search application is started, the display control unit 104 may directly display the plurality of test images in the medical image viewers 620 to 640.

Figure 6:
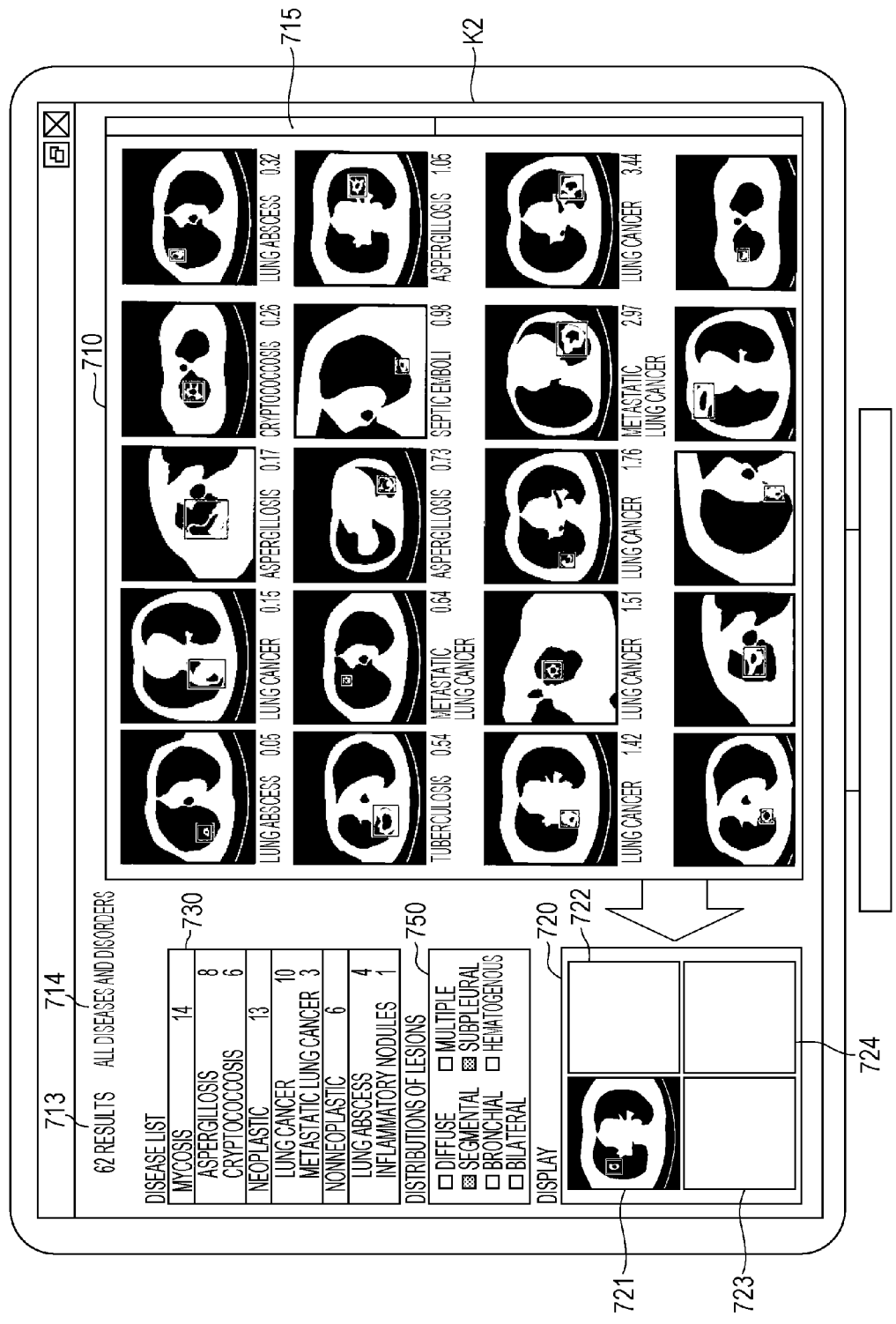
FIG. 6 is a diagram illustrating an example of a basic screen displayed on a display immediately after the similar case search application is started on the information terminal.

FIG. 6 is a diagram illustrating an example of a basic screen K2 displayed on the display 101*b* immediately after the similar case search application is started on the information terminal 100. The basic screen K2 illustrated in FIG. 6 includes a case display area 710, a layout area 720, a disease list display area 730, and a distribution list display area 750. The layout area 720 is an example of a first display area, and the case display area 710 is an example of a second display area. The disease list display area 730 is an example of a third display area.

The case display area 710 is an area where thumbnail images of similar cases that are similar to the search query image are displayed in order of similarity. The thumbnail image of a similar case is an example of a similar medical image.

Since the case display area 710 shows a large number of similar cases, further processing for resolution conversion or pixel-value conversion will take time. To avoid this inconvenience, the thumbnail images are created in advance from the original slice images, and are stored in the case search system 300.

Further description will now be given of resolution conversion and pixel-value conversion. Each original slice image has a resolution of 512 pixels by 512 pixels, whereas each thumbnail image has a lower resolution. Thus, resolution conversion is needed. Each of the thumbnail images is generated through the resolution reduction and grayscale conversion of the corresponding one of the original slice images.

For example, the grayscale conversion process is performed in the following way. The slice images obtained by CT imaging have pixel values (CT values) of 2000 grayscale values from −1000 to +1000 (expressed in Hounsfield units (HU)), and are not directly displayed on a standard 8-bit grayscale display. Even if such slice images can be displayed, it is difficult for a person to distinguish the areas of pulmonary emphysema (with a CT value of −1000 HU), normal lung tissue (with a CT value of approximately −900 HU), the area of ground-glass opacity (with a CT value of −800 HU), soft tissue (with a CT value of −100 to −50 HU), water (with a CT value of 0 HU), and bone (with a CT value of 1000 HU), in the range of the 2000 grayscale values, from one another with the naked eye.

Thus, slice images are typically reconstructed with 8-bit pixel values for display on a display, where a window level and a window width are set for each pixel value. The window level represents the CT value of the center of the window, and the window width represents the difference between the upper limit and lower limit of a range centered about the center of the window.

For example, in a case where a DICOM image is reconstructed with the pulmonary condition, the window level is set to −550 to −800 and the window width is set to 1000 to 1600. Thus, a thumbnail image is also generated through the processing described above to reduce the pixel values of the original slice image to 8-bit pixel values.

The thumbnail images displayed in the case display area 710 are thumbnail images representing similar cases for which the distance from the feature vector of the case to be diagnosed is less than or equal to a predetermined threshold value. The distance is a Euclidean distance, by way of example. Any other distance measure, such as city block, may be used as the distance. As the distance between the two images to be compared decreases, the similarity between them increases. The feature vectors are not obtained from the thumbnail images but are obtained from the original images, that is, the slice images.

Figure 7:
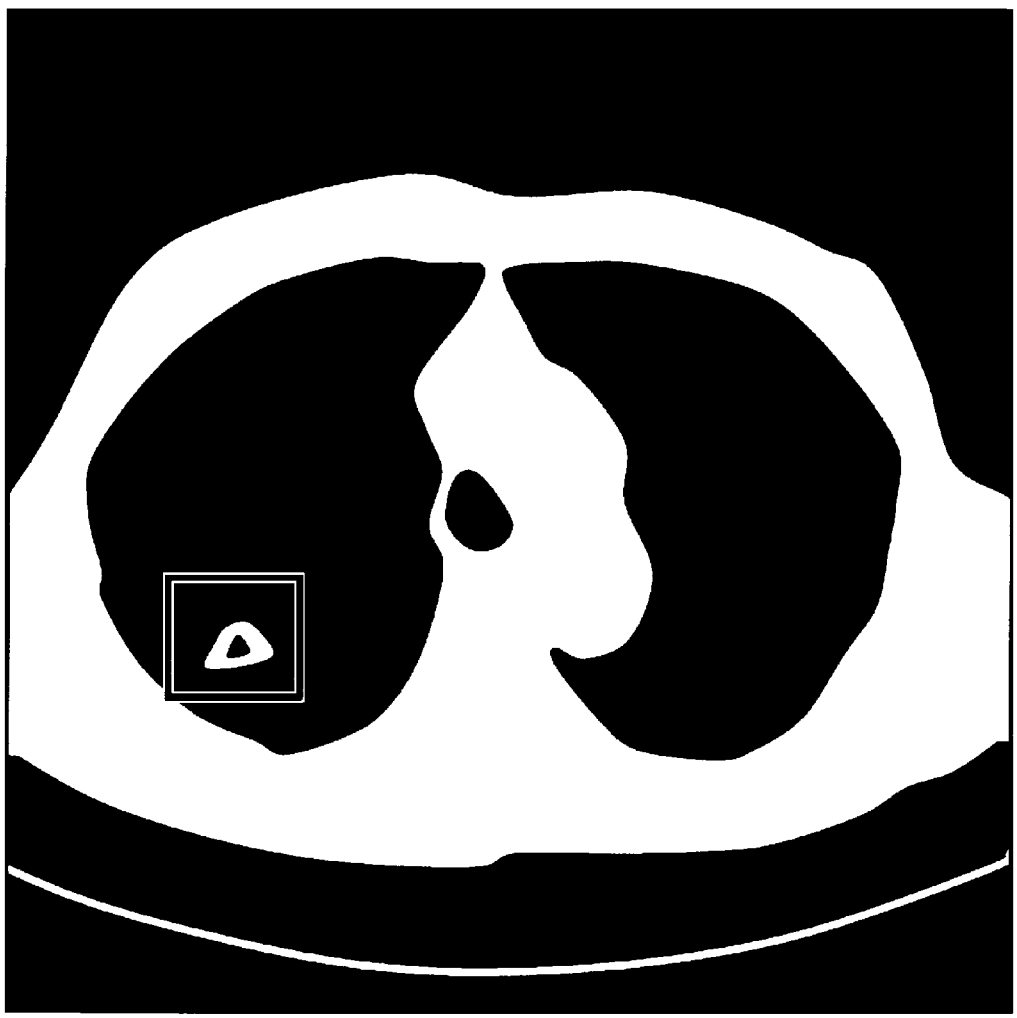
FIG. 7 is a diagram illustrating a display area for a certain similar case extracted from among similar cases displayed in a case display area.

FIG. 7 is a diagram illustrating a display area for a certain similar case extracted from among the similar cases displayed in the case display area 710. A thumbnail image is displayed in the display area for the similar case, and a definitely diagnosed disease display area 711 and a distance display area 712 are placed below the thumbnail image. The definitely diagnosed disease display area 711 shows the name of the definitely diagnosed disease of the target similar case. The name of the definitely diagnosed disease is the name of a disease as which the target similar case has been diagnosed in definite diagnosis. The distance display area 712 shows the distance between the feature vector for the slice image of the target similar case and the feature vector for the search query image. In the example illustrated in FIG. 7, the definitely diagnosed disease display area 711 shows "nontuberculous mycobacteria (NTM)". Thus, the illustrated thumbnail image is a thumbnail image of a similar case diagnosed as "nontuberculous mycobacteria (NTM)" in definite diagnosis. The distance display area 712 shows "0.05", which indicates that the distance between the slice image of the similar case and the search query image is "0.05".

Referring back to FIG. 6, for example, a number-of-search-result display area 713 is placed in an upper left portion of the basic screen K2. The number-of-search-result display area 713 shows the number of similar cases similar to the case to be diagnosed. The number of similar cases is obtained from the case search system 300 as a result of the search.

If the number of similar cases is very large, not all the similar cases will be displayed in the case display area 710 at the same time. For example, a vertical scrollbar 715 is placed on the right side of the case display area 710 to enable vertical scrolling. The display control unit 104 provides vertical scrolling through the thumbnail images displayed in the case display area 710 in accordance with the amount of movement of the scrollbar 715 for display. This allows currently invisible similar cases to be displayed in the case display area 710 to enable the user to observe the similar cases.

The scrollbar 715 may be a horizontal scrollbar. In this case, the display control unit 104 may be configured to provide horizontal scrolling through the thumbnail images displayed in the case display area 710 in accordance with the amount of movement of the scrollbar 715. Alternatively, the display control unit 104 may be configured to, in response to pressing any arrow key on the keyboard while the mouse pointer is in the case display area 710, provide scrolling through the thumbnail images displayed in the case display area 710, over a period during which the key is pressed, in the direction corresponding to the pressed key.

The information terminal 100 is configured to acquire from the case search system 300 thumbnail images for which the distance from the search query image is less than or equal to a predetermined threshold value. This is merely an example. For example, the information terminal 100 may acquire a certain number of thumbnail images from the case search system 300 in order of decreasing similarity. Alternatively, the information terminal 100 may acquire thumbnail images from the case search system 300 so that a certain number of thumbnail images corresponding to a certain definitely diagnosed disease name are always included.

The thumbnail images may be displayed in the case display area 710 in such a manner that, for example, the thumbnail image with the shortest distance from the search query image is displayed at the left end of the top row and the distance sequentially increases from left to right, where, once the right end of the same row is reached, the next, large-distance thumbnail image is displayed at the left end of the second row from the top. That is, the following display technique may be used: The thumbnail images are displayed in the case display area 710, from left to right, top to bottom, in order of increasing distance.

Other display technique may be used in this embodiment. For example, the thumbnail images may be displayed in such a manner that the thumbnail image with the shortest distance is displayed at the top end of the first column from the left and the distance sequentially increases from top to bottom, where, once the bottom end of the same column is reached, the next, large-distance thumbnail image is displayed at the top end of the second column from the left. Alternatively, the plurality of display techniques described above may be switched between by the user.

In the example described above, distance is used as similarity measure. Any index indicating the similarity between images, such as cosine similarity, may be used. In a case where cosine similarity is used, as the value approaches 1, the similarity between two images to be compared increases.

The similar cases to be displayed in the case display area 710 can be refined according to a disease name, e.g., a disease name displayed in the disease list display area 730, or by distribution of lesions, e.g., a distribution of lesions displayed in the distribution list display area 750, which will be described in detail below. A condition under which the similar cases are refined in the current setting is displayed in a display condition display area 714. In the example illustrated in FIG. 6, the state immediately after a similar case search has been performed is illustrated, and no refinement is performed. Thus, "all diseases and disorders" is displayed in the display condition display area 714.

The layout area 720 is displayed in, for example, a lower left portion of the basic screen K2 illustrated in FIG. 6. The layout area 720 is used so that an image that the user wishes to observe in more detail among the thumbnail images of the similar cases displayed in the case display area 710 is displayed in a medical image viewer on the display 101a. As illustrated in FIG. 5, the four medical image viewers 610 to 640 arranged in a grid of two rows and two columns are displayed on the display 101a. Further, the layout area 720 has four display boxes 721 to 724 arranged in a grid of two rows and two columns. In the manner described above, the number and layout of medical image viewers 610 to 640 displayed on the display 101a is consistent with the number and layout of display boxes 721 to 724 in the layout area 720. In accordance with the display of the search query image in the medical image viewer 610 illustrated in FIG. 5, the thumbnail image of the search query image is initially displayed in the display box 721. The display box 721 in which the thumbnail image of the search query image is displayed is an example of a first display box.

Each of the other display boxes 722 to 724 shows a thumbnail image of a similar case in accordance with an image displayed in the corresponding one of the medical image viewers 620 to 640. That is, when the input control unit 103 detects that one of the thumbnail images displayed in the case display area 710 has been dragged and dropped onto one of the display boxes 722 to 724, the display control unit 104 causes the thumbnail image to be displayed in the display box, and also causes the slice image corresponding to the thumbnail image to be displayed in the medical image viewer corresponding to the display box. Accordingly, the medical image viewers 610 to 640 are associated with the display boxes 721 to 724 in a one-to-one correspondence.

In the example illustrated in FIG. 6, the display boxes 722 to 724 are blank, and the medical image viewers 620 to 640 illustrated in FIG. 5 are also blank accordingly.

The user performs a drag-and-drop operation using the mouse to move the thumbnail image that the user wishes to observe in more detail from the case display area 710 to the layout area 720. For example, when the user moves a thumbnail image to the display box 722, the slice image corresponding to the thumbnail image is displayed in the medical image viewer 620 corresponding to the display box 722. Also, when the user moves a thumbnail image to the display box 723, the slice image corresponding to the thumbnail image is displayed in the medical image viewer 630 corresponding to the display box 723. That is, a thumbnail image is moved to any display box among the display boxes 721 to 724, resulting in a thumbnail image of a similar case being displayed adjacent to the thumbnail image of the search query image. This enables the user to compare the case to be diagnosed and the similar case on the level of thumbnail images and to quickly determine the similarity between the two cases. Since thumbnail images have a smaller amount of information than slice images, the user is able to roughly estimate how much the case to be diagnosed and the similar case which is adjacent in the layout area 720 are similar. This enables the user to efficiently narrow a large number of similar cases displayed in the case display area 710 down to a final set of candidates of similar cases to be compared with the case to be diagnosed in more detail on the level of slice images.

The search query image and the slice image of the similar case are also displayed on the display 101a in the same position and layout as those in the layout area 720. After the completion of narrowing down to a final set of candidates of similar cases in the layout area 720, the case to be diagnosed and similar cases obtained as the final set of candidates are displayed on the display 101a on the level of slice images without inputting any operation. This guides the user smoothly to the next operation step of detailed image interpretation of the case to be diagnosed and the similar cases obtained as the final set of candidates.

The disease list display area 730 with the heading "disease list" is displayed in an upper left portion of the basic screen K2 illustrated in FIG. 6. The disease list display area 730 shows the names of the definitely diagnosed diseases of all the similar cases obtained as a result of the similar case search. The case to be diagnosed is labeled the name of a definitely diagnosed disease after diagnosis, and is then accumulated in the case search system 300 as a similar case. Thus, each similar case is labeled in advance the name of a definitely diagnosed disease which is obtained through diagnosis.

FIG. 8 is an enlarged view of the disease list display area 730. In FIG. 8, the names of definitely diagnosed diseases are displayed separately as the names of major-category diseases (731, 734, 737, 741, and 744) and the names of subcategory diseases (732, 733, 735, 736, 738, 739, 740, 742, 743, and 745). In the example illustrated in FIG. 8, "mycosis" 731, "neoplastic" 734, "nonneoplastic" 737, "mycobacteriosis" 741, and "other" 744 are displayed as the names of major-category diseases.

In the example illustrated in FIG. 8, furthermore, "aspergillosis" 732 and "cryptococcosis" 733 are displayed as the names of subcategory diseases of the "mycosis" 731. Further, "lung cancer" 735 and "metastatic lung cancer" 736 are displayed as the names of subcategory diseases of the "neoplastic" 734. Further, "lung abscess" 738, "sarcoidosis" 739, and "septic emboli" 740 are displayed as the names of subcategory diseases of the "nonneoplastic" 737. Further, "nontuberculous mycobacteria (NTM)" 742 and "tuberculosis" 743 are displayed as the names of subcategory diseases of the "mycobacteriosis" 741. Further, "bronchiectasis" 745 is displayed as the name of a subcategory disease of the "other" 744.

Figure 9:
FIG. 9 is a diagram illustrating a basic screen on which similar cases are refined according to "mycosis"
Figure 10:
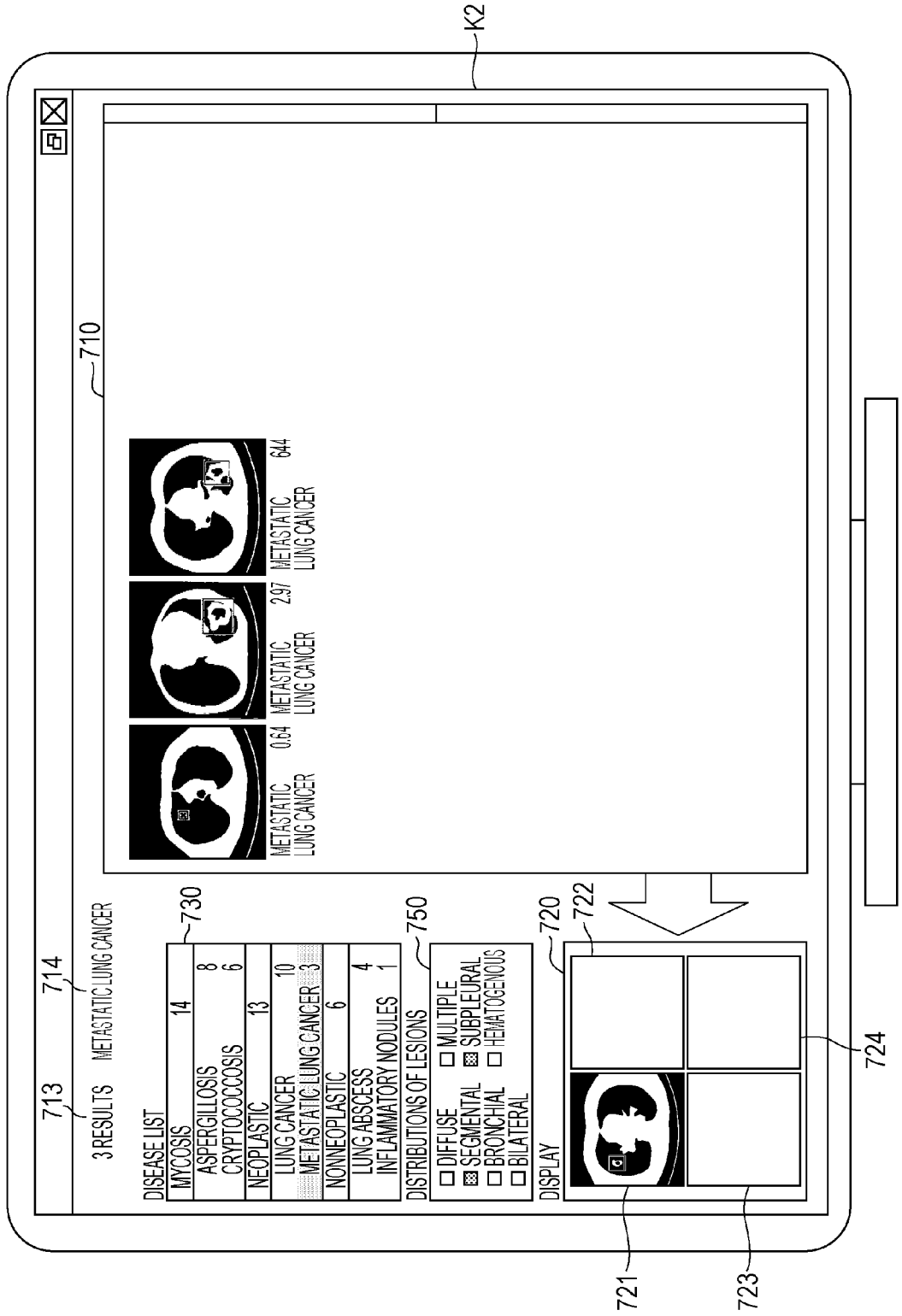
FIG. 10 is a diagram illustrating a basic screen on which similar cases are refined according to "metastatic lung cancer"

Further, next to the names of the major-category diseases and the subcategory diseases are the numbers of cases of the respective diseases. By selecting a row corresponding to any of the names of the major-category diseases or subcategory diseases in the disease list display area 730, the user can refine the similar cases to be displayed in the case display area 710. As illustrated in FIG. 6, immediately after a similar case search is made, 62 similar cases including diverse diseases and disorders are set as targets to be displayed. As a result of clicking on the row corresponding to the "mycosis" 731 in FIG. 8 with the mouse, as illustrated in FIG. 9, the display control unit 104 displays similar cases of mycosis in the case display area 710. As a result of clicking on the row corresponding to the "metastatic lung cancer" 736 in FIG. 8 with the mouse, as illustrated in FIG. 10, the display control unit 104 displays similar cases of metastatic lung cancer in the case display area 710.

In this case, the display control unit 104 displays the name of the disease used for refinement in the display condition display area 714 so that the user can identify how the similar cases currently being displayed in the case display area 710 have been refined. FIG. 9 is a diagram illustrating the basic screen K2 on which similar cases are refined according to "mycosis". FIG. 10 is a diagram illustrating the basic screen K2 on which similar cases are refined according to "metastatic lung cancer".

In the example illustrated in FIG. 9, "mycosis" is displayed in the display condition display area 714 since refinement is performed in accordance with "mycosis". In the example illustrated in FIG. 10, "metastatic lung cancer" is displayed in the display condition display area 714 since refinement is performed in accordance with "metastatic lung cancer".

In this case, furthermore, the display control unit 104 displays in the number-of-search-result display area 713 the number of similar cases being displayed in the case display area 710 so that the user can identify the number of similar cases being displayed in the case display area 710. Since there are 14 similar cases of "mycosis", "14 results" is displayed in the number-of-search-result display area 713 in the example illustrated in FIG. 9. Since there are three similar cases of "metastatic lung cancer", "3 results" is displayed in the number-of-search-result display area 713 in the example illustrated in FIG. 10.

With the function described above, similar cases corresponding to the name of a disease suspected by a physician before image-based diagnosis are displayed in the case display area 710, enabling the physician to easily make sure that the case to be diagnosed is consistent with the name of the suspected disease.

In the examples illustrated in FIG. 9 and FIG. 10, thumbnail images of similar cases corresponding to a single disease name selected in the disease list display area 730 are arranged horizontally in order of decreasing similarity to the search query image. Specifically, in the example illustrated in FIG. 9, the following display technique is displayed: The thumbnail images are displayed in such a manner that the thumbnail image with the shortest distance from the search query image is displayed at the left end of the first row and the distance sequentially increases from left to right, where, once the right end of the same row is reached, the next, large-distance thumbnail image is displayed at the left end of the second row from the top. In the example illustrated in FIG. 10, the thumbnail images of the three similar cases are displayed in the first row in such a manner that the distance sequentially increases from left to right.

In the manner described above, in this embodiment, when a single disease name is selected in the disease list display area 730, the display control unit 104 displays thumbnail images of similar cases corresponding to the selected single disease name so that the thumbnail images are arranged horizontally in order of decreasing similarity.

When a plurality of disease names are selected in the disease list display area 730, the display control unit 104 divides the case display area 710 into sub-areas in accordance with the number of selected disease names, and displays thumbnail images of similar cases of each of the selected diseases in the corresponding one of the sub-areas.

Figure 48:
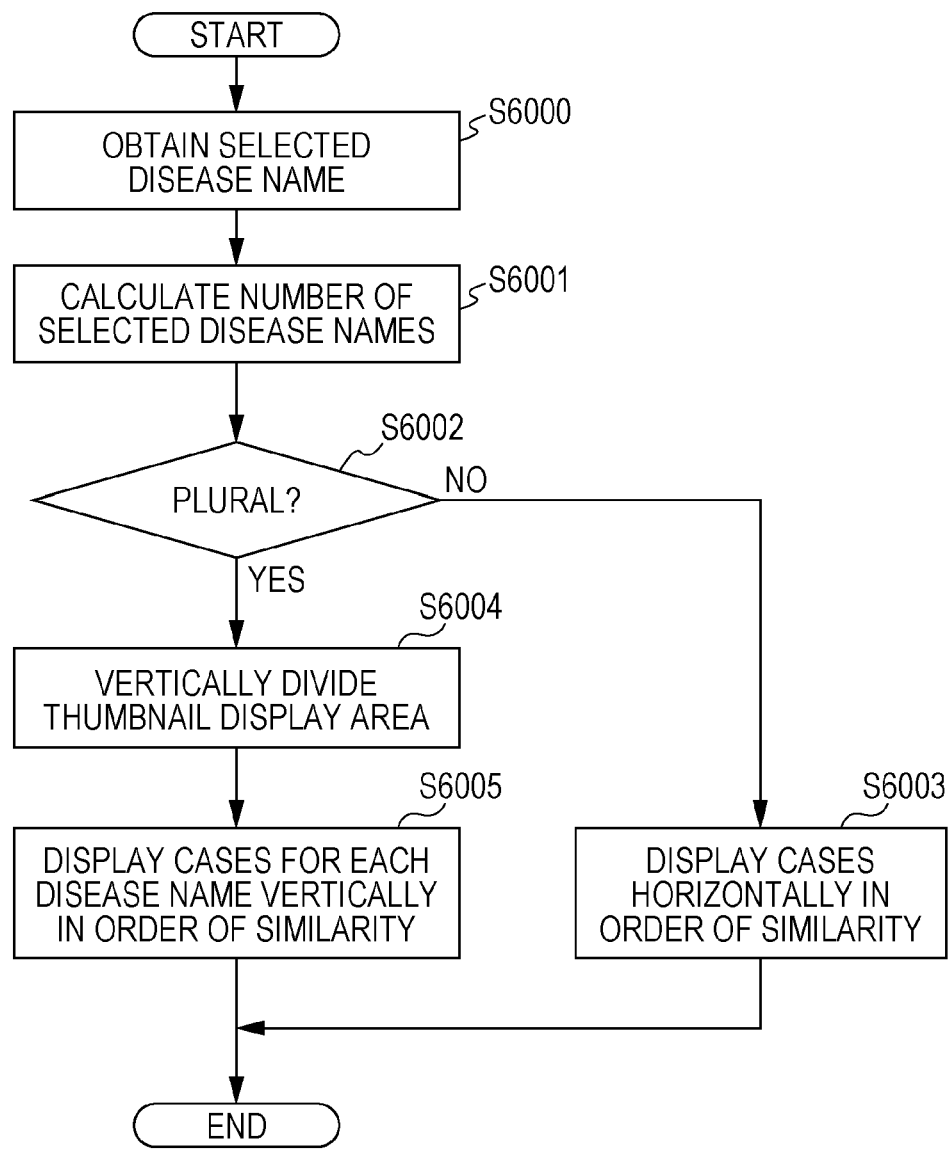
FIG. 48 is a flowchart illustrating an example of a display process performed when a disease name is selected in the disease list display area.

FIG. 48 is a flowchart illustrating an example of a display process performed when a disease name is selected in the disease list display area 730. A display process performed for the case display area 710 when a disease name displayed in the disease list display area 730 is selected will be described in detail with reference to the flowchart illustrated in FIG. 48.

First, in S6000, the display control unit 104 obtains a disease name selected by the user in the disease list display area 730. The operation of the user to select a disease name will be described below.

In S6001, the display control unit 104 calculates the number of disease names selected in S6000.

In S6002, the display control unit 104 determines whether or not the number of disease names calculated in S6001 is plural. If the number of disease names is not plural (NO in S6002), the process proceeds to S6003. If the number of disease names is plural (YES in S6002), the process proceeds to S6004.

The processing of S6003 is a display process performed for the case display area 710 when one disease name is selected in the disease list display area 730. In this case, as illustrated in FIG. 9 or FIG. 10, thumbnail images of similar cases corresponding to the disease name selected in S6000 are displayed in the case display area 710 so as to be arranged horizontally in order of increasing distance. Specifically, the thumbnail images of the similar cases are displayed in such a manner that the similar case with the shortest distance from (or the highest similarity to) the search query image is displayed at the left end of the first row from the top and the distance increases (or the similarity decreases) from left to right, where, once the right end of the first row is reached, the similar case with the next large distance is displayed at the left end of the second row from the top.

In typical keyword-based image retrieval on the Internet or the like, search results are generally displayed in such a manner that the search results are arranged from left to right across the screen in order of decreasing relevance to the keyword. That is, when a plurality of images are displayed in a horizontal and vertical arrangement on a search result screen, the user tends to view the search result screen with a preconception that an image closer to the upper left corner has a higher relevance to the keyword. In this embodiment, to fit the preconception described above, a plurality of similar cases are arranged horizontally in order of decreasing similarity to the search query image.

The processing of S6004 and S6005 is a display process performed for the case display area 710 when a plurality of disease names are selected in the disease list display area 730.

In S6004, the display control unit 104 vertically divides the case display area 710 into sub-areas in accordance with the number of disease names calculated in S6001. Through this process, a number of sub-areas equal to the number of disease names obtained in S6000 are created. The created sub-areas are vertically elongated so that thumbnail images of similar cases having each of the disease names are aligned in a column.

In S6005, the display control unit 104 displays, in each of the sub-areas created in S6004, thumbnail images of similar cases having the corresponding one of the disease names so that the thumbnail images are aligned in a column in order of decreasing similarity.

Figure 49:
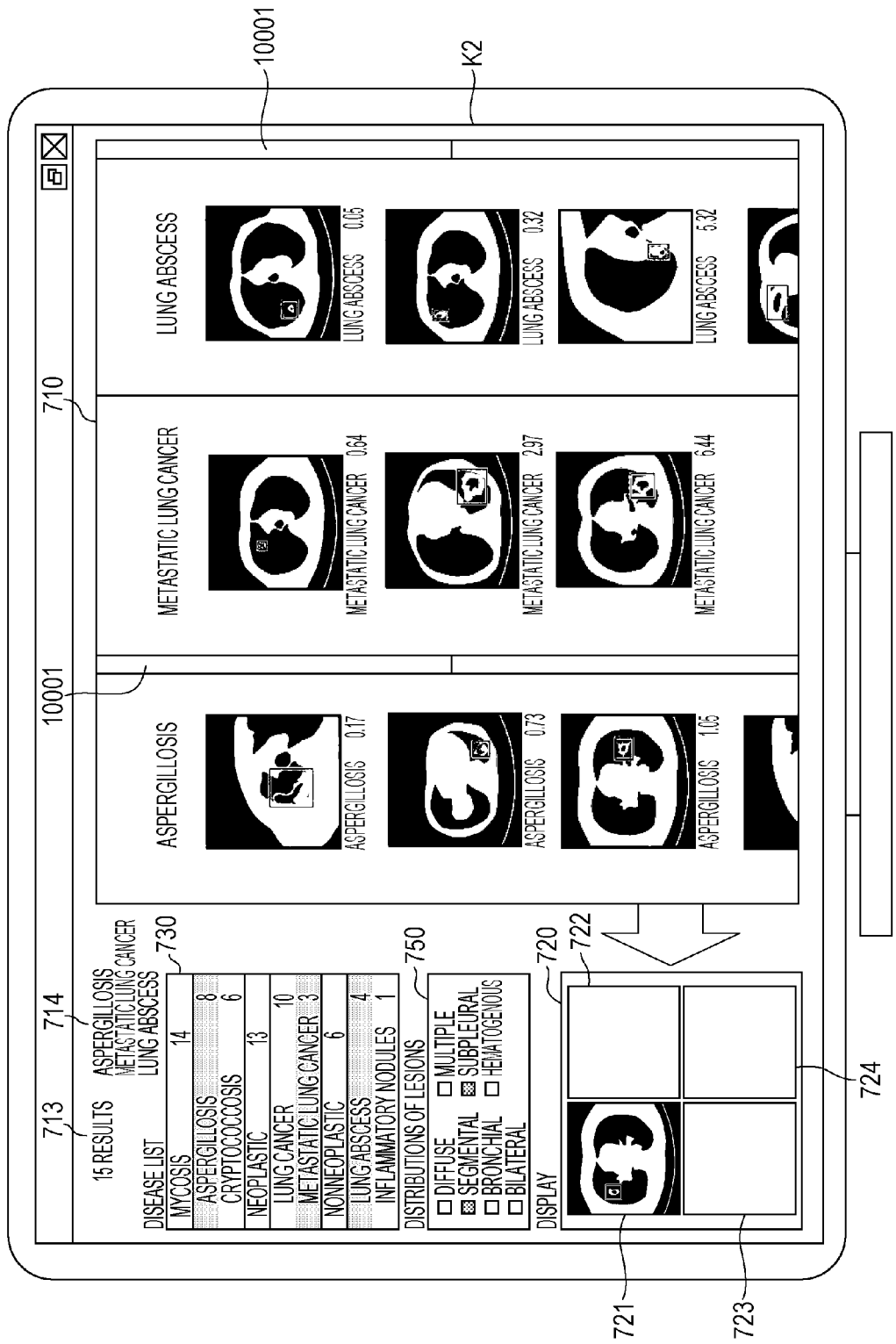
FIG. 49 is a diagram illustrating an example of a basic screen created when a plurality of disease names are selected.

FIG. 49 is a diagram illustrating an example of the basic screen K2, which is created when a plurality of disease names are selected. The illustrated basic screen K2 shows the state after three disease names, namely, aspergillosis, metastatic lung cancer, and lung abscess, are selected in the disease list display area 730 illustrated in FIG. 6. Accordingly, "aspergillosis", "metastatic lung cancer", and "lung abscess" are displayed in the display condition display area 714. Since there are 15 similar cases corresponding to the three disease names, "15 results" is displayed in the number-of-search-result display area 713. Furthermore, since the three disease names are selected, the case display area 710 is vertically divided into three sub-areas each corresponding to one of the three disease names. In each of the sub-areas, thumbnail images of similar cases of the corresponding one of the disease names are displayed so as to be aligned in a column in order of decreasing similarity.

In the illustrated example, three sub-areas with the headings "aspergillosis", "metastatic lung cancer", and "lung abscess", which correspond to the three disease names, are displayed in order from left to right. In each of the sub-areas, thumbnail images of similar cases corresponding to the corresponding one of the disease names are displayed so as to be aligned in a column.

With the display described above, even before reference images similar to the search query image are refined or after similar cases are refined by selecting one or more disease names, thumbnail images of similar cases with high similarity to the search query image among the similar cases are collected in an upper portion of the case display area 710. This enables the physician to give priority to the study of a thumbnail image of a similar case having high similarity to the search query image, even before reference images for the search query image are refined or after thumbnail images of similar cases are refined by selecting one or more disease names. Accordingly, by providing a system with efficiently improved comparison accuracy, this embodiment may contribute to an improvement in medical treatment accuracy.

If there are thumbnail images to be displayed in a sub-area, the number of which is greater than or equal to a certain value, and not all the thumbnail images are displayed in the sub-area at the same time, the display control unit 104 may provide the sub-area with a scrollbar 10001. In the example illustrated in FIG. 49, there are thumbnail images to be displayed in each of two sub-areas, namely, the sub-area for "aspergillosis" in the first column from the left and the sub-area for "lung abscess" in the third column from the left, the number of which is greater than or equal to a certain value, and not all the thumbnail images are displayed in such sub-areas at the same time. Thus, vertical scrollbars 10001 are placed in the two sub-areas. When each of the scrollbars 10001 slides up, the display control unit 104 scrolls the corresponding one of the sub-areas down with the heading of the associated disease name or while maintaining the heading of the associated disease name in place by a distance corresponding to the amount of sliding. When each of the scrollbars 10001 slides down, the display control unit 104 scrolls the corresponding one of the sub-areas up with the heading of the associated disease name or while maintaining the heading of the associated disease name in place by a distance corresponding to the amount of sliding. This enables the user to view the thumbnail images of all the similar cases corresponding to the selected disease name. The value used to determine whether the scrollbar 10001 is displayed may be equal to the number of thumbnail images that can be displayed in a sub-area at the same time, in view of the relationship between the size of the sub-area and the size of each thumbnail image. In the example illustrated in FIG. 49, up to three thumbnail images can be displayed in each sub-area at the same time. Thus, it may be sufficient that the display control unit 104 provides a sub-area with the scrollbar 10001 if there are four or more thumbnail images to be displayed in the sub-area.

Figure 50:
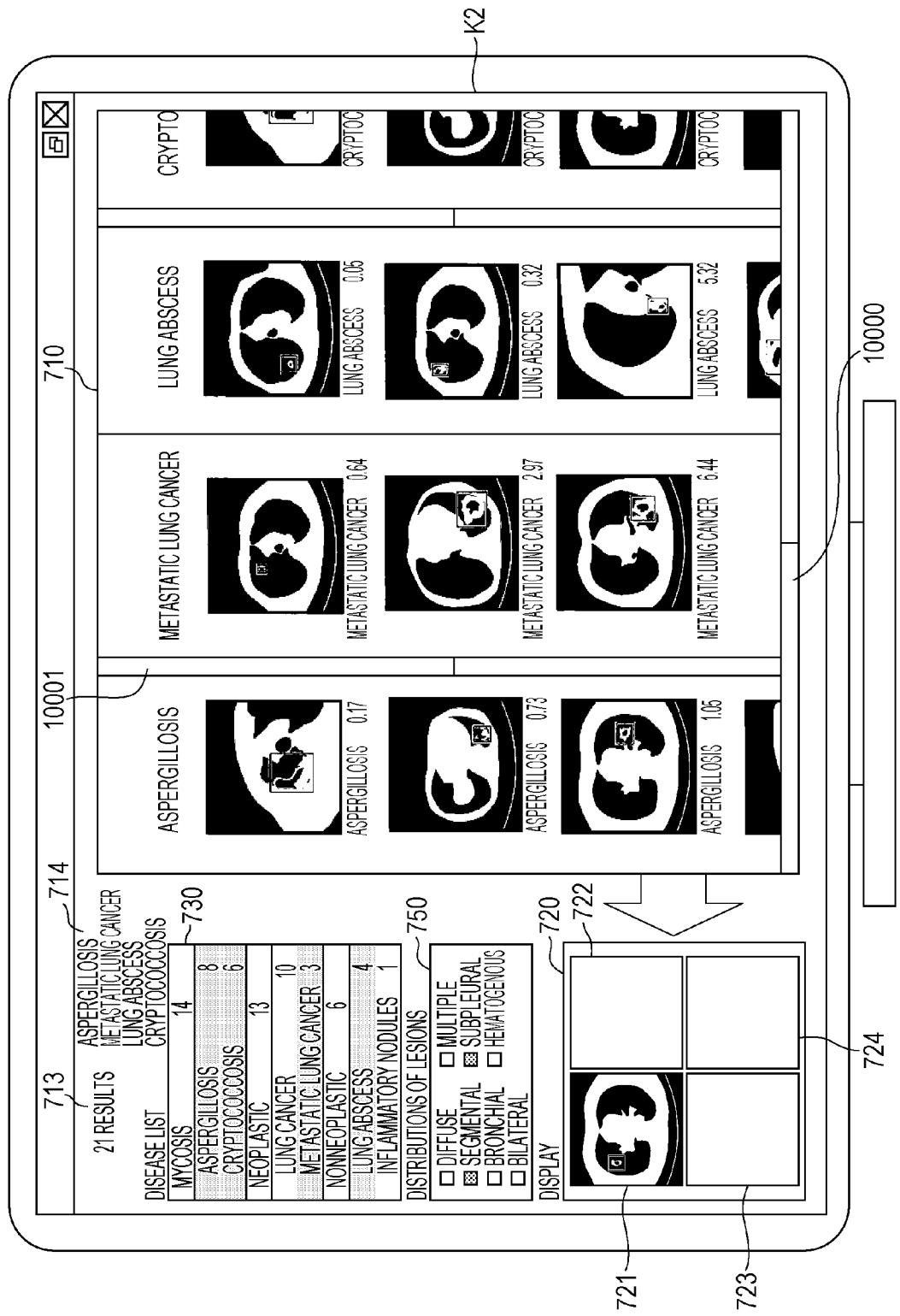
FIG. 50 is a diagram illustrating a basic screen on which the number of selected disease names is greater than or equal to a certain value.

In FIG. 49, if the number of selected disease names is greater than or equal to a certain value, as illustrated in FIG. 50, the case display area 710 may be extended using a scrollbar 10000 or the like. FIG. 50 is a diagram illustrating the basic screen K2 on which the number of selected disease names is greater than or equal to a certain value. In a case where the size of a thumbnail image to be displayed in the case display area 710 is kept at a predetermined value or more in terms of image interpretability, if the number of selected disease names is greater than or equal to a certain value, not all the selected disease names will be displayed in the case display area 710 at the same time. Accordingly, if the number of selected disease names is greater than or equal to a certain value, the display control unit 104 provides the case display area 710 with the scrollbar 10000 to substantially extend the case display area 710.

In the example illustrated in FIG. 50, the basic screen K2, which is obtained after four disease names, namely, aspergillosis, metastatic lung cancer, lung abscess, and cryptococcosis, are selected in the disease list display area 730 illustrated in FIG. 6, is illustrated. As illustrated in FIG. 50, the case display area 710 is vertically divided into four sub-areas each corresponding to one of the four disease names, and shows, in each of the sub-areas, thumbnail images of similar cases of the corresponding one of the disease names. Part of the sub-area for cryptococcosis, which is in the fourth column from the left, is not currently visible. Accordingly, the display control unit 104 provides the case display area 710 with a horizontal scrollbar 10000. When the scrollbar 10000 slides to the right, the display control unit 104 scrolls the case display area 710 to the left by a distance corresponding to the amount of sliding to make the sub-area for cryptococcosis, part of which is not currently visible, visible in the case display area 710 in its entirety. In the manner described above, in a case where the number of selected disease names is greater than or equal to a certain value, scrolling the case display area 710 with the scrollbar 10000 allows the user to view the similar cases corresponding to all the selected disease names. In the foregoing description, the scrollbar 10000 is used by way of example. However, this embodiment is not limited to this example. For example, the following method may be used: The case display area 710 is scrolled to the right by dragging the mouse to the left while the mouse is in the case display area 710, and the case display area 710 is scrolled to the left by dragging the mouse to the right while the mouse is in the case display area 710.

The number of disease names used to determine whether the scrollbar 10000 is displayed may be equal to a predetermined number of sub-areas that can be displayed in the case display area 710 at the same time in view of, for example, the relationship between the size of the case display area 710 and the size of each thumbnail image. In the example illustrated in FIG. 50, the number of sub-areas, the entirety of which can be displayed in the case display area 710 at the same time, is three. Thus, the scrollbar 10000 is displayed when the user selects four or more disease names.

In S6003, if one disease name is selected in the disease list display area 730, thumbnail images are displayed in the case display area 710, by way of example, so as to be aligned side-by-side in a row in order of decreasing similarity. However, this embodiment is not limited to this example. For example, if one disease name is selected in the disease list display area 730, the display control unit 104 may display thumbnail images in the case display area 710 so that the thumbnail images are aligned in a column in order of decreasing similarity.

Figure 51:
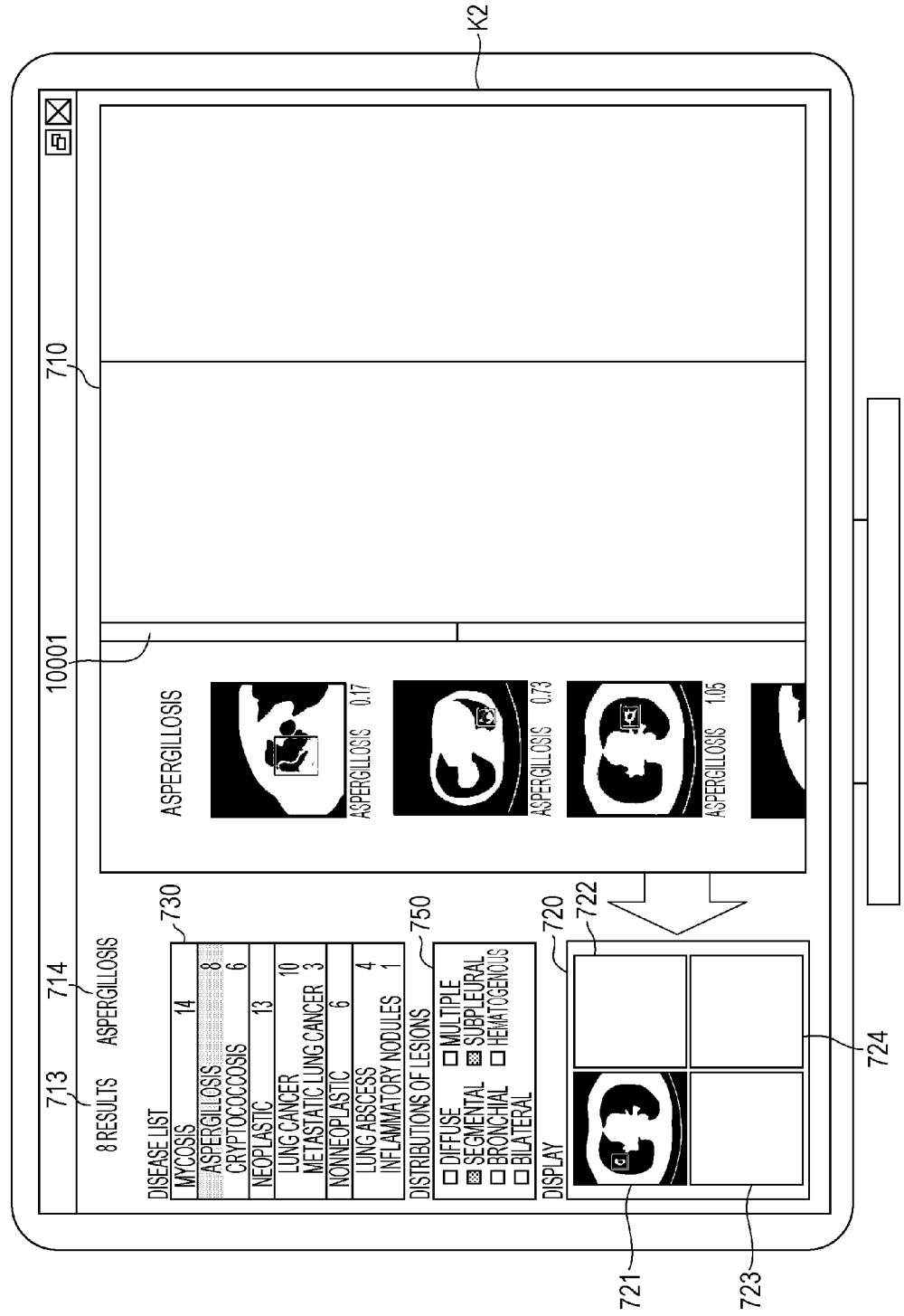
FIG. 51 is a diagram illustrating a basic screen on which aspergillosis has been selected in the disease list display area illustrated in FIG. 6.

FIG. 51 is a diagram illustrating the basic screen K2, which is obtained after aspergillosis is selected in the disease list display area 730 illustrated in FIG. 6. In the example illustrated in FIG. 51, thumbnail images of aspergillosis, which is selected as a disease name, are displayed in the case display area 710 so as to be aligned in a column in order of decreasing similarity. The display described above enables the user to view the retrieved clinical cases within the same line of sight as that when a plurality of disease names are selected, improving searching usability.

Referring back to FIG. 6, the distribution list display area 750 with the heading "distributions of lesions" is displayed in a left middle portion of the basic screen K2. The distribution list display area 750 shows types of distributions of lesions seen in all the similar cases obtained from the case search system 300 as a result of the similar case search.

FIG. 11 is an enlarged view of the distribution list display area 750. In the example illustrated in FIG. 11, the names of seven distributions of lesions are displayed, and checkboxes are displayed to the left of the respective names of the distributions of lesions. In the example illustrated in FIG. 11, "diffuse" 751, "segmental" 752, "bronchial" 753, "bilateral" 754, "multiple" 755, "subpleural" 756, and "hematogenous" 757 are displayed as distributions of lesions.

The distributions of lesions described above are defined in advance, and each similar case is given in advance a distribution flag value ("1" for Applicable or "0" for Not Applicable) indicating the applicability of the similar case to each of the "diffuse" 751 to the "hematogenous" 757. In some similar cases, the distribution flag values for all the distributions of lesions may be set to Not Applicable ("0"), and, in other similar cases, the distribution flag values for a plurality of distributions of lesions may be set to Applicable ("1").

The case search system 300 according to this embodiment searches for a similar case that has a region of interest similar to a region of interest set by a user in a slice image of the case to be diagnosed. A lesion may be present in a slice image other than the slice image in which the region of interest has been set by the user. Further, the user may wish to, after searching for a similar case on the basis of the slice image in which the region of interest has been set, compare a slice image other than the slice image in which the region of interest has been set with the similar case found as a result of the search. In this case, the user inputs a slice-based forwarding operation on the medical image viewer 610 to display a different slice image, and compares the displayed slice image with the found similar case. If a similar case related to the lesion of interest among all the similar cases found as a result of the search is displayed in the case display area 710, the operation of extracting a slice image having the desired lesion from among slice images other than the slice image in which the region of interest has been set can be smoothly performed. Accordingly, this embodiment provides a function of refining the found similar cases according to the desired distribution of lesions to make the operation described above smoother.

In this embodiment, the "diffuse" 751 to the "hematogenous" 757 illustrated in FIG. 11 are used as distributions of lesions in the pulmonary field. In addition, as illustrated in FIG. 11, the display control unit 104 displays the checkboxes and the names of the distributions of lesions in such a manner that the distributions of lesions available for refinement are active and the distributions of lesions not available for refinement are inactive. Here, being "active" refers to having higher luminance than the state of being "inactive", and being "inactive" refers to having lower luminance than the state of being "active".

In the example illustrated in FIG. 11, the "diffuse" 751, the "bronchial" 753 to the "multiple" 755, and the "hematogenous" 757 are displayed as active, whereas the "segmental" 752 and the "subpleural" 756 are displayed as inactive, because of the following reasons: The distribution flag values for the "diffuse" 751, the "bronchial" 753 to the "multiple" 755, and the "hematogenous" 757 are currently set to "1" (Applicable) in at least one similar case among all the similar cases obtained through the similar case search, whereas the distribution flag values for the "segmental" 752 and the "subpleural" 756 are currently set to "0" (Not Applicable) in all the obtained similar cases.

When the input control unit 103 detects that a check mark is placed in one or more of the active checkboxes, the display control unit 104 causes only similar cases that meet the lesion condition(s) for which the checkbox is checked to be displayed in the case display area 710.

Note that the distribution flag values for the "segmental" 752 and the "subpleural" 756 are set to "0" (Not Applicable) in any of the similar cases obtained as a result of the search. Thus, if the checkboxes for the "segmental" 752 and the "subpleural" 756 are allowed to be checked, even though a check mark is placed in the checkboxes for such distributions of lesions, no similar case will be displayed in the case display area 710. In this case, it is meaningless to place a check mark. To avoid this situation, in this embodiment, a distribution of lesions for which the distribution flag value is set to "0" (Not Applicable) in any of the similar cases obtained as a result of the search is displayed as inactive.

Figure 13:
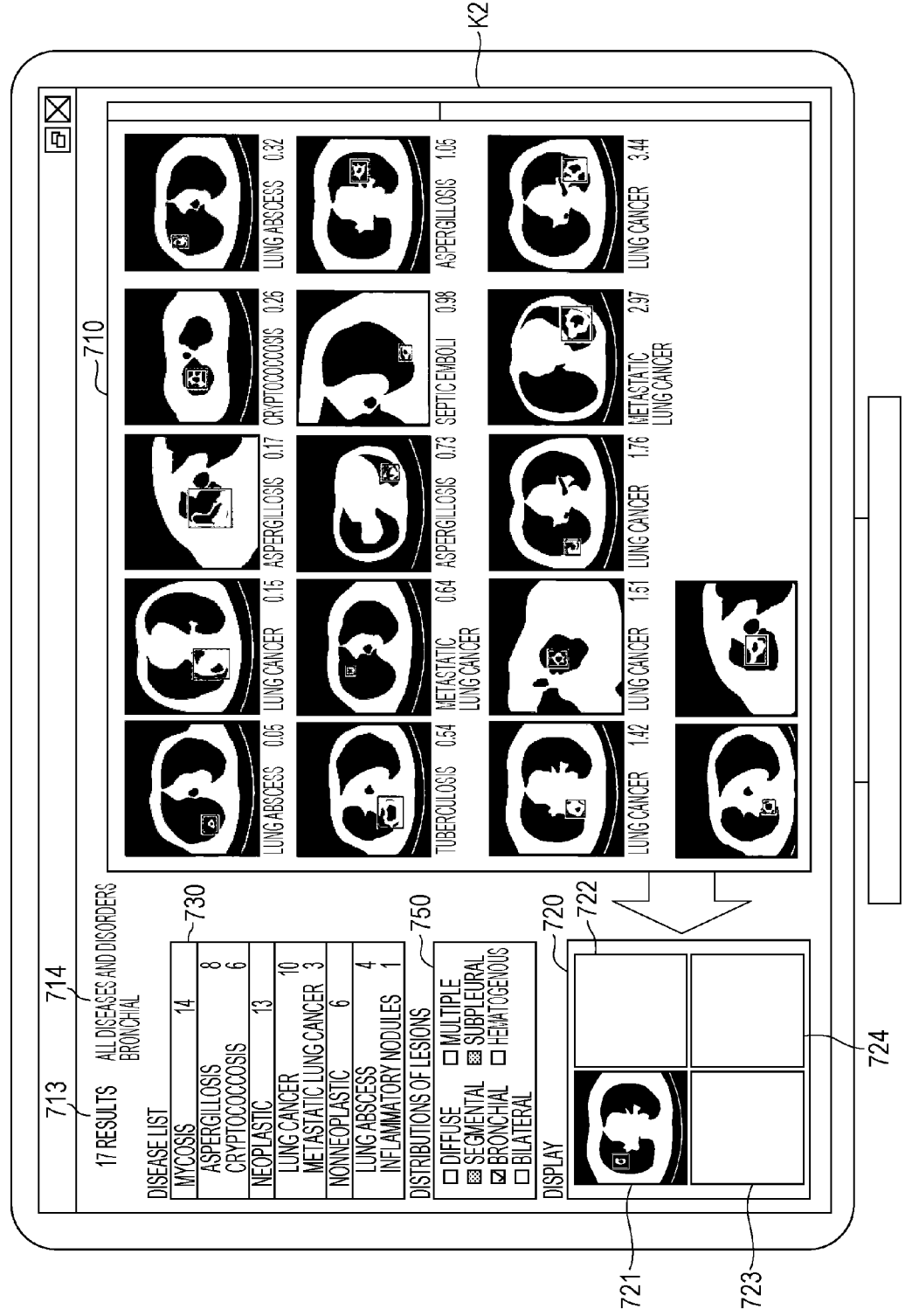
FIG. 13 is a diagram illustrating a basic screen on which refinement is performed in accordance with a bronchial distribution of lesions.

FIG. 12 is a diagram illustrating the distribution list display area 750 in which a checkbox is checked. FIG. 13 is a diagram illustrating the basic screen K2 on which refinement is performed in accordance with a bronchial distribution of lesions. As illustrated in FIG. 12, when a check mark is placed in the checkbox for the "bronchial" 753, as illustrated in FIG. 13, the display control unit 104 displays similar cases having a bronchial distribution of lesions in the case display area 710. In the illustrated example, 17 similar cases have a bronchial distribution of lesions. Thus, the display control unit 104 displays "17 results" in the number-of-search-result display area 713. The display control unit 104 further displays the disease name to be displayed and the name of the distribution of lesions, i.e., "bronchial", in the display condition display area 714. In the example illustrated in FIG. 13, there is no refinement according to a disease name in the disease list display area 730, "all diseases and disorders" is displayed in the display condition display area 714.

Figure 15:
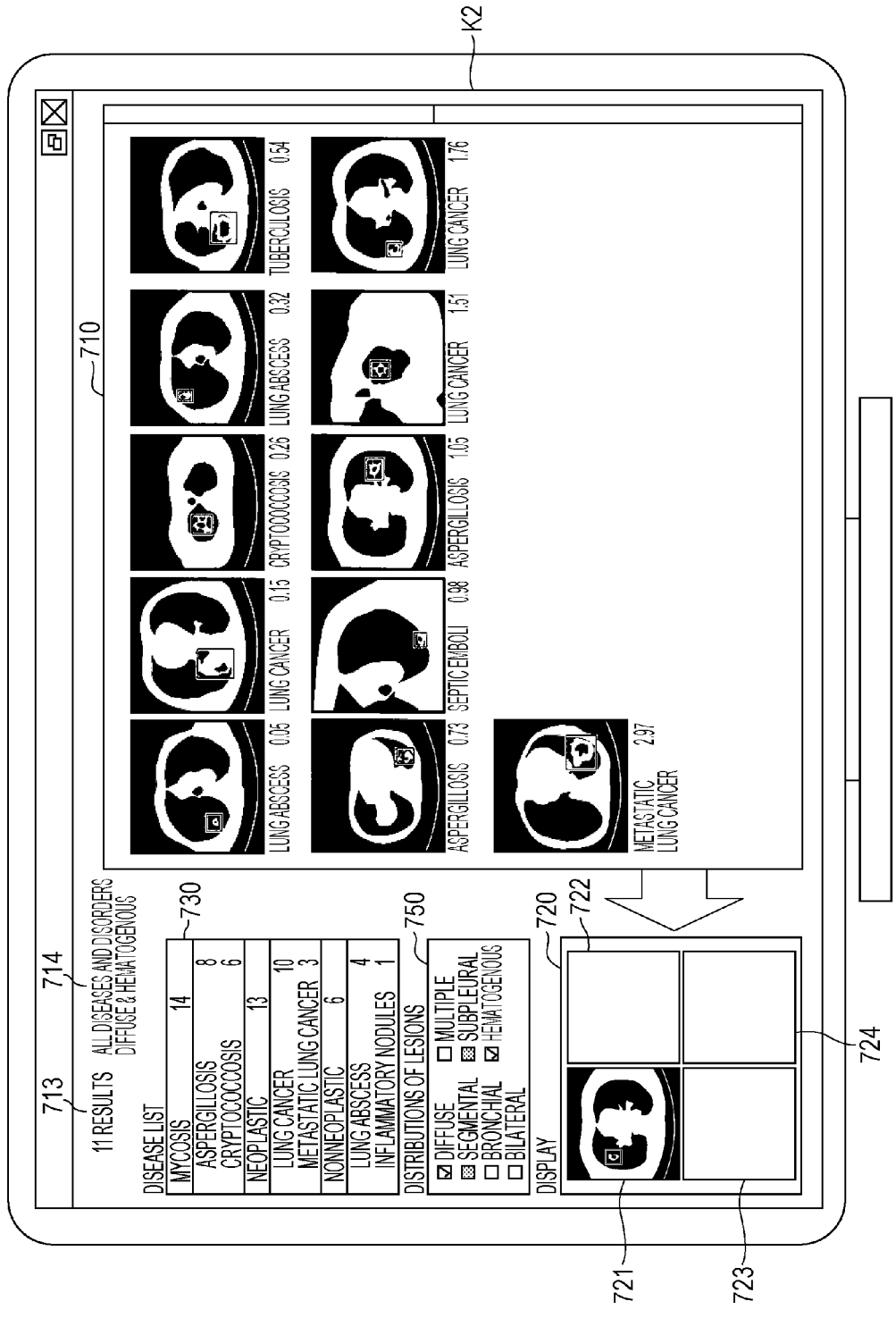
FIG. 15 is a diagram illustrating a basic screen on which refinement is performed in accordance with a plurality of distributions of lesions.

FIG. 14 is a diagram illustrating the distribution list display area 750 when a plurality of checkboxes are checked. FIG. 15 is a diagram illustrating the basic screen K2 on which refinement is performed in accordance with a plurality of distributions of lesions. In the example illustrated in FIG. 14, check marks are placed in the checkboxes for the "diffuse" 751 and the "hematogenous" 757. Accordingly, as illustrated in FIG. 15, the display control unit 104 displays similar cases having diffuse and hematogenous distributions of lesions in the case display area 710. In the illustrated example, 11 similar cases have diffuse and hematogenous distributions of lesions. Thus, the display control unit 104 displays "11 results" in the number-of-search-result display area 713. The display control unit 104 further displays the disease name to be displayed (here, "all diseases and disorders", since there is no refinement according to a disease name) and the names of the distributions of lesions, i.e., "diffuse & hematogenous", in the display condition display area 714.

FIG. 16 is a diagram illustrating the data configuration of patient information 1000. The patient information 1000 is accumulated in the patient information accumulation unit 201 on a patient-by-patient basis, and is managed by the patient information management unit 202 of the medical information management system 200. The patient information 1000 has personal information such as the gender and age of a patient, clinical information such as the past medical history that the patient has, and test information on medical tests that the patient has undergone, such as a blood test. As illustrated in FIG. 16, the patient information 1000 includes a patient ID 1100, a name 1200, an age 1300, a gender 1400, a past medical history 1500, a family history 1600, a chief complaint 1700, test information 1800, and a definite diagnosis 1900.

The patient ID 1100 is an identifier specific to the patient. The name 1200, the age 1300, the gender 1400, the past medical history 1500, the family history 1600, and the chief complaint 1700 are the name, age, gender, past medical history, family history, and chief complaint of the patient identified by the patient ID 1100, respectively. The test information 1800 indicates information concerning one or more medical tests that the patient has already undergone, as illustrated in FIG. 17.

FIG. 17 is a diagram illustrating the data configuration of the test information 1800 registered in the patient information 1000 illustrated in FIG. 16. The test information 1800 is information concerning tests performed on the patient, and a piece of test information is created for each test. The test information 1800 includes a test ID 1810, a test date 1820, a test type 1830, and a test result 1840. The test ID 1810 is an identifier specific to each test. The test date 1820 is the date on which the test was performed. The test type 1830 is the type of the test. Examples of the type of the test include blood tests, respiratory tests, endoscopic examinations, simple X-ray imaging tests, and CT imaging tests.

The test result 1840 includes the values of various indices, such as white blood cell count (or leukocyte count), lactate dehydrogenase (LDH), and glutamic-pyruvic transaminase (GPT) for a blood test. The test result 1840 also includes, for example, a decision made by a physician based on various indices. For an imaging test such as a simple X-ray imaging test or a CT imaging test, the test result 1840 includes pointer information on a pointer to a captured image and pointer information on a pointer to a report obtained as a result of image-based diagnosis. Images captured during tests are accumulated in DICOM format in the medical image data accumulation unit 203 of the medical information management system 200.

In a case where the test type 1830 is an imaging test such as simple X-ray, CT, MRI, or positron emission tomography (PET), medical image data obtained with such imaging tests is accumulated in a medical image database 2000 stored in the medical image data accumulation unit 203 of the medical information management system 200.

Figure 18:
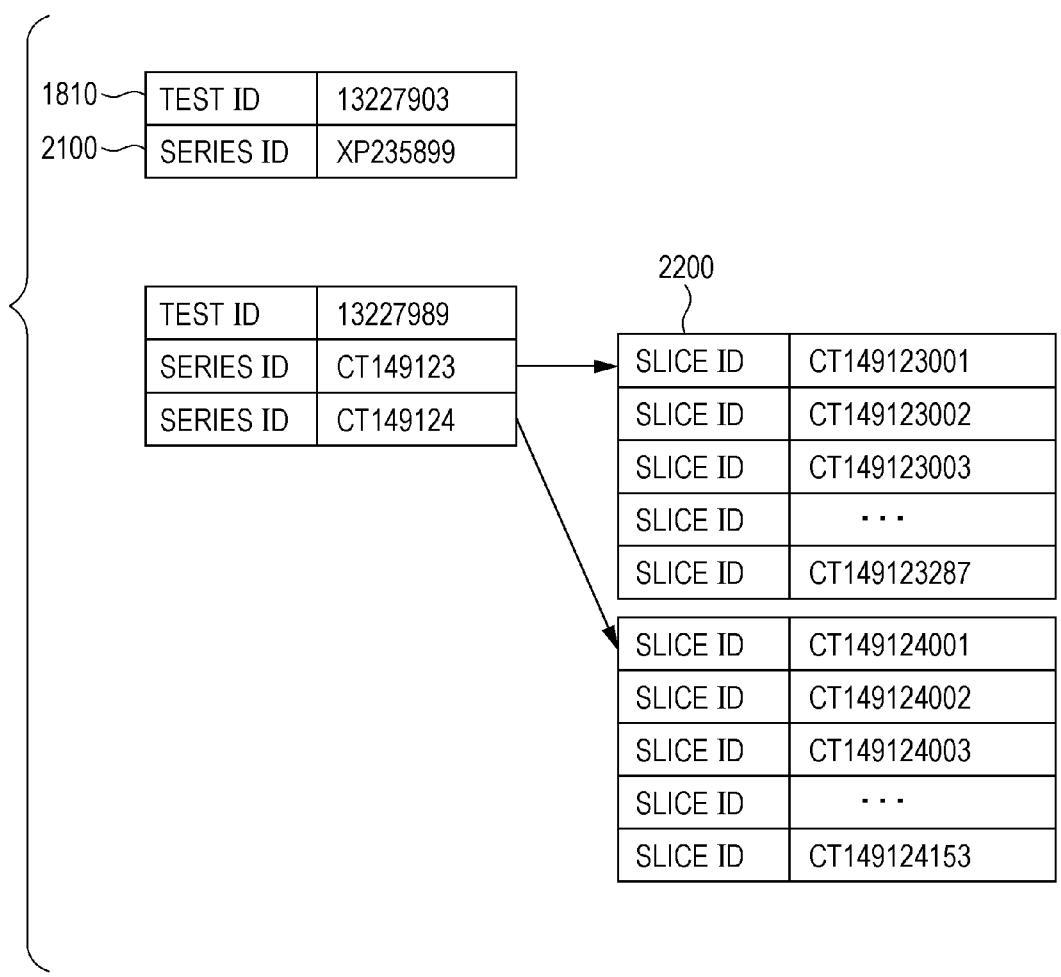
FIG. 18 is a diagram illustrating the data configuration of a medical image database.

FIG. 18 is a diagram illustrating the data configuration of the medical image database 2000. The medical image database 2000 includes a test ID 1810 and a series ID 2100. A plurality of series IDs 2100 may be associated with a single test ID 1810 since a plurality of types of imaging sessions (e.g., simple CT, contrast CT, etc.) may be performed in a single test. That is, a number of series corresponding to the number of types of imaging sessions are obtained.

A series is also obtained for each condition of the reconstruction of captured images, as well as for each type of imaging session. For example, when captured images are reconstructed under the pulmonary condition and the mediastinal condition, one series is obtained for each of these conditions. In images reconstructed under the pulmonary condition, blood vessels in the lungs, bronchi, alveoli, and the like are displayed highlighted. In images reconstructed under the mediastinal condition, the mediastinal structures, such as blood vessels and lymph nodes, are displayed highlighted. The pulmonary condition and the mediastinal condition are obtained by the reconstruction of images obtained in single imaging sessions. Thus, two imaging sessions, or simple CT and contrast CT, are performed, and images are reconstructed under the pulmonary condition and the mediastinal condition in each of the two imaging sessions, thereby obtaining two series for the pulmonary condition and two series for the mediastinal condition.

For imaging tests such as CT and MRI, a plurality of slice images are obtained in a single imaging session. Thus, a plurality of slice IDs 2200 are associated with one series ID 2100. In FIG. 18, two series IDs "CT149123" and "CT149124" are associated with the test ID "13227989". Thus, it is found that CT images of two series have been obtained with the test. It is also found that a plurality of slice IDs 2200 are associated with each of the series IDs "CT149123" and "CT149124".

In a case where the test type 1830 is an imaging test such as simple X-ray, CT, MRI, or PET, a diagnostic report 3000 as illustrated in FIG. 19 is accumulated in the diagnostic report management unit 205 of the medical information management system 200. The diagnostic report 3000 includes a diagnosis from a physician for each test. FIG. 19 is a diagram illustrating the data configuration of the diagnostic report 3000.

The diagnostic report 3000 includes a test ID 1810, findings 3100, and a diagnosis 3200. The test ID 1810 is the same as the test ID 1810 illustrated in FIG. 17. Accordingly, the diagnostic report 3000 and the test information 1800 are associated with each other. The findings 3100 include a note indicating the physician's findings of the test. The diagnosis 3200 includes a note indicating the physician's diagnosis for the test.

Figure 20:
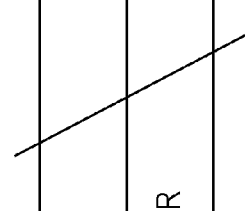
FIG. 20 is a diagram illustrating the data configuration of similar case data.

FIG. 20 is a diagram illustrating the data configuration of similar case data 4000. The similar case data 4000 is data to be referred to in order to search for a similar case that is similar to the case to be diagnosed, and a piece of similar case data is created for each similar case. The similar case data 4000 is an example of information attached to similar case data, in which disease information is set. The similar case data 4000 is accumulated for each similar case in the similar case data accumulation unit 301 of the case search system 300. As illustrated in FIG. 20, the similar case data 4000 includes a similar case ID 4100, a slice ID 4200, region-of-interest information 4300, image feature data 4400, thumbnail image data 4500, distribution-of-lesion information 4600, a definite diagnosis (major-category disease name) 4700, and a definite diagnosis (subcategory disease name) 4800.

The similar case ID 4100 is an identifier of the similar case data 4000. Since a piece of similar case data is generated for each region of interest set in a slice image of a similar case, the similar case ID 4100 can also be referred to as an identifier of the region of interest. In the example illustrated in FIG. 20, the similar case ID 4100 is constituted by a symbol sequence including "SIM" and a number which follows it.

Figure 21:
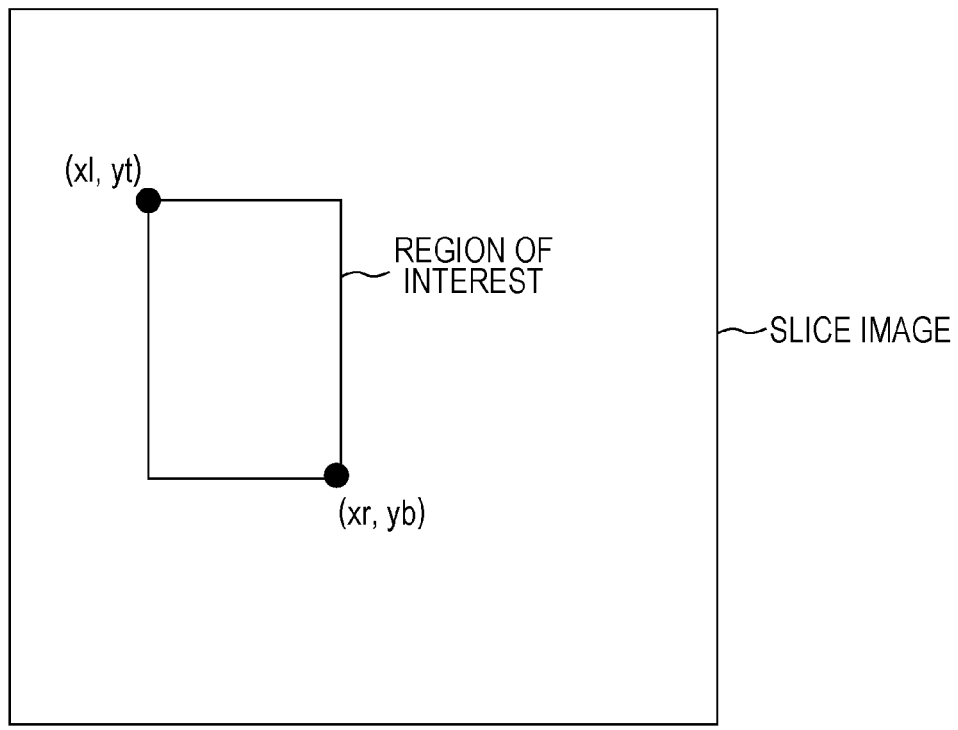
FIG. 21 is a schematic diagram illustrating a region of interest set in a slice image.

The slice ID 4200 is an identifier of a slice image in which a region of interest is set, and is the same as the slice ID 2200 illustrated in FIG. 18. The region-of-interest information 4300 is information indicating the position of the region of interest set in the slice image. FIG. 21 is a schematic diagram illustrating a region of interest set in a slice image. In the example illustrated in FIG. 21, the region of interest has a rectangular shape. Thus, the region-of-interest information 4300 includes four values, namely, the coordinates (xl, yt) of the upper left corner of the region of interest and the coordinates (xr, yb) of the lower right corner of the region of interest. The region of interest may also be of any other shape than rectangular, in which case a parameter capable of uniquely identifying the region is used as the region-of-interest information 4300. For example, the region of interest may be circular. In this case, the coordinates of the center of the circular region and the radius of the circular region may be used as the region-of-interest information 4300.

The image feature data 4400 is certain-number dimensional (here, N-dimensional) feature values extracted from the region of interest defined in the region-of-interest information 4300. The thumbnail image data 4500 is image data of a thumbnail image generated based on a DICOM slice image identified by the slice ID 4200 to display in the case display area 710. In the thumbnail image data 4500, for example, pixel values of the thumbnail image are arranged in raster scan order from the upper left corner to the lower right corner of the thumbnail image. As described previously, a DICOM image obtained with a CT test is an 11-bit image having a size of 512 pixels×512 pixels (with a pixel value of −1000 to +1000). In this embodiment, accordingly, to increase the speed of display of a thumbnail image, a DICOM image on which the thumbnail image is based is subjected to resolution reduction and grayscale conversion to create a thumbnail image with 8-bit pixel values in advance, and the resulting thumbnail image is registered in the similar case data 4000. Thumbnail images may be created by, for example, the medical information management system 200, and transmitted to the case search system 300. Alternatively, thumbnail images may be created by the case search system 300 by obtaining DICOM images from the medical information management system 200.

The distribution-of-lesion information 4600 is a distribution flag value ("1" for Applicable or "0" for Not Applicable) indicating the applicability of the target similar case to each of the predetermined distributions of lesions identified by "diffuse" 4610, "segmental" 4620, "bronchial" 4630, "bilateral" 4640, "multiple" 4650, "subpleural" 4660, and "hematogenous" 4670.

The definite diagnosis (major-category disease name) 4700 indicates the name of a disease that is definitely diagnosed in the target similar case and that is classified as a major category (hereinafter referred to as a "major-category disease"). The definite diagnosis (major-category disease name) 4700 is used to refine similar cases according to a major-category disease name.

The definite diagnosis (subcategory disease name) 4800 indicates the name of a disease that is definitely diagnosed in the target similar case and that is classified as a subcategory (hereinafter referred to as a "subcategory disease"). The definite diagnosis (subcategory disease name) 4800 is used to refine similar cases according to a subcategory disease name.

In the definite diagnosis (major-category disease name) 4700, the name of a major-category disease that is uniquely associated with the definite diagnosis (subcategory disease name) 4800 is defined in advance. The definite diagnosis (major-category disease name) 4700 is stored in the similar case data 4000 using the association relationship between them.

In the definite diagnosis (subcategory disease name) 4800, a series ID 2100 is identified in the medical image data accumulation unit 203 by a slice ID 2200 illustrated in FIG.

18. Further, a test ID 1810 is identified in the patient information accumulation unit 201 by the identified series ID 2100, and associated patient information 1000 (FIG. 16) is identified by the test ID 1810. Accordingly, the definite diagnosis 1900 of the patient is identified by the identified patient information 1000.

Next, a process from the start of image interpretation to the start of a similar case search by using the information terminal 100 in coordination with the medical information management system 200 and the case search system 300 will be described.

Figure 22:
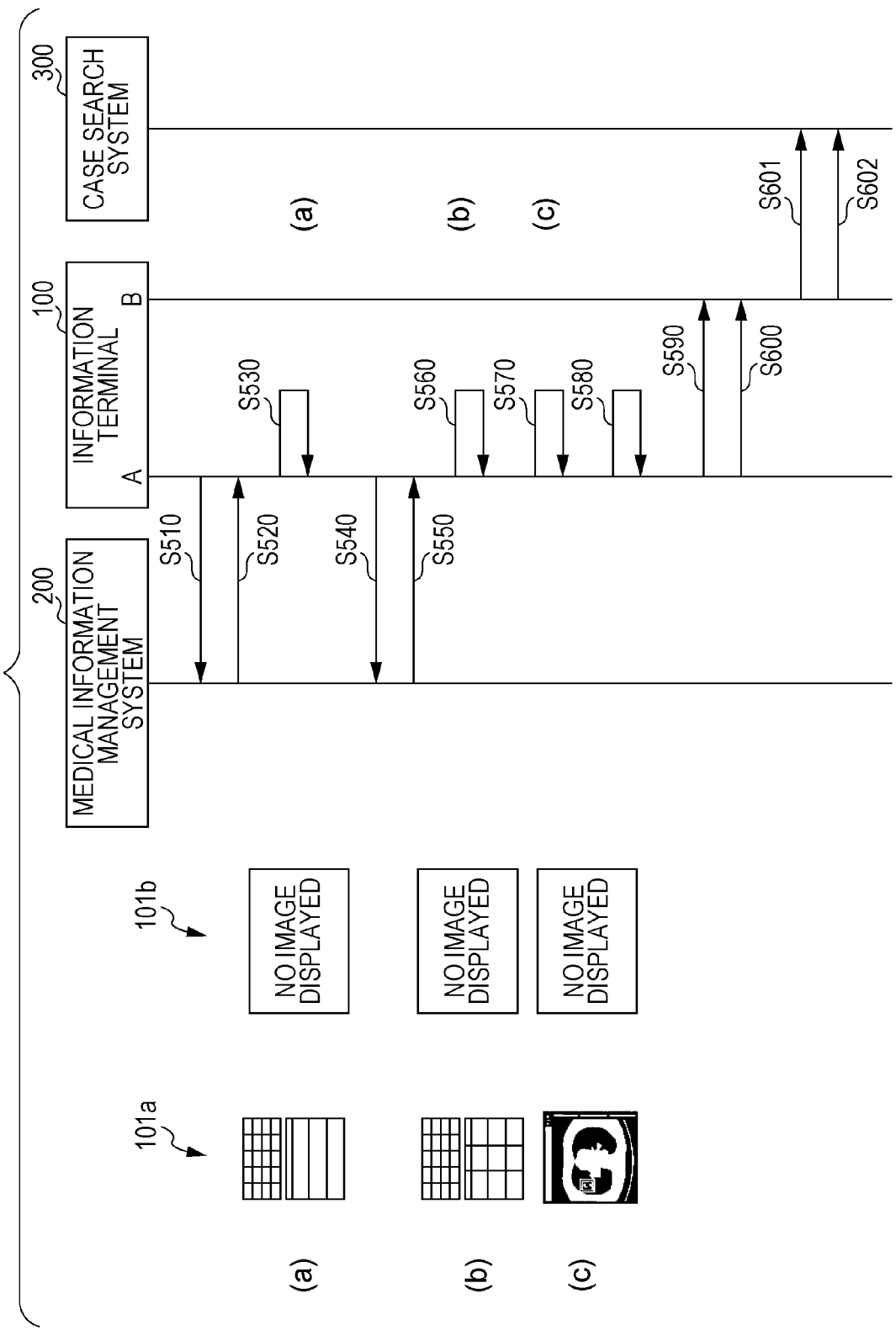
FIG. 22 is a sequence diagram illustrating a process in which the information terminal obtains a case to be diagnosed from the medical information management system and then sends a similar case search request to the case search system and the case search system receives the similar case search request.

FIG. 22 is a sequence diagram illustrating a process in which the information terminal 100 obtains a case to be diagnosed from the medical information management system 200 and then sends a similar case search request to the case search system 300 and the case search system 300 receives the similar case search request. In FIG. 22, rectangular objects to the left of the sequence diagram, which are arranged side-by-side in two lines, represent screens displayed on the displays 101*a* and 101*b* through the processing of the respective steps. In FIG. 22, furthermore, in the information terminal 100, "A" represents the medical information management application, and "B" represents the similar case search application. It is assumed that the medical information management application is started in advance before the commencement of the above-described sequence.

First, the information terminal 100 accepts a request for displaying a test list in which image interpretation is to be performed by a user (a specialist who provides image interpretation) through the operation unit 102, and transmits the request for displaying the test list to the communication control unit 206 of the medical information management system 200 via the input control unit 103 and the communication control unit 110 (S510).

The patient information management unit 202 of the medical information management system 200 lists tests in which image interpretation is yet to be performed after the completion of an imaging test to generate a test list in which image interpretation is to be performed. Then, the patient information management unit 202 transmits the generated test list to the communication control unit 110 of the information terminal 100 via the communication control unit 206 (S520). The test list includes the patient information 1000 on the patient, and the test information 1800.

The display control unit 104 of the information terminal 100 displays the test list received by the communication control unit 110 on the display 101 (S530).

In this case, the test list is displayed on the display 101*a*, whereas no image is displayed on the display 101*b*.

FIG. 23 is a view of a test list screen. The test list includes an area 800 where tests with image interpretation yet to be performed are displayed, and an area 810 where information concerning series included in the tests is displayed. The area 800 has the following fields: "patient ID", "patient name", "test date", "test ID", and "test type". The "patient ID" and "patient name" fields show the patient ID 1100 and the name 1200 registered in the patient information 1000, respectively. The "test date", "test ID", and "test type" fields show the test date 1820, the test ID 1810, and the test type 1830 registered in the test information 1800, respectively. The area 810 is an area for displaying the details of a test selected by the user in the area 800, and has the following fields: "series ID", "definition", and "image". In FIG. 23, no test (corresponding to each row) is selected by the user in the area 800, and thus no image is displayed in the area 810.

The user selects a test in which image interpretation is about to be performed from among the tests displayed in the area 800. When the selection of the test is detected by the input control unit 103, as illustrated in FIG. 22, the communication control unit 110 transmits a request for displaying all the series included in the test ID of the selected test to the medical information management system 200 (S540).

When the communication control unit 206 of the medical information management system 200 receives the display request, the patient information management unit 202 refers to the medical image database 2000 illustrated in FIG. 18 to obtain all the slice images of all the series included in the test ID designated in the display request, and transmits the slice images to the information terminal 100 via the communication control unit 206 (S550). For example, in the example illustrated in FIG. 18, when the test with the test ID "13227989" is selected by the user, all the slice images included in the series with the series IDs "CT149123" and "CT149124" are transmitted in S550.

When the communication control unit 110 of the information terminal 100 obtains the images of all the series, the display control unit 104 displays a series list in the area 810 to display information concerning all the series included in the designated test ID in list form (S560).

In this case, the area 810 for a test list, which is displayed on the display 101*a*, shows a list of series corresponding to the test selected in the area 800, whereas no image is displayed on the display 101*b*.

FIG. 24 is a view of the test list screen obtained after a test is selected. In the area 800 illustrated in FIG. 24, a selected row is highlighted. In the example illustrated in FIG. 24, the test for "John Doe" in the second row is selected in the area 800. Accordingly, the "series IDs", "definitions", and "images" for the selected test are displayed in the area 810. The series IDs associated with the test ID of the selected test in the medical image database 2000 are displayed in the "series ID" field, and thumbnail images of single typical slice images of the displayed series ID are displayed in the "image" field. Each of the single typical slice images of the series ID is an image corresponding to a predetermined slice position. The predetermined slice position may be the initial slice position or the center slice position. The "definition" indicates an imaging condition or a reconstruction condition for the associated series. The "definition" is registered in association with, for example, a series ID 2100 in the medical image database 2000 in FIG. 18, although not illustrated in the drawings.

Figure 47:
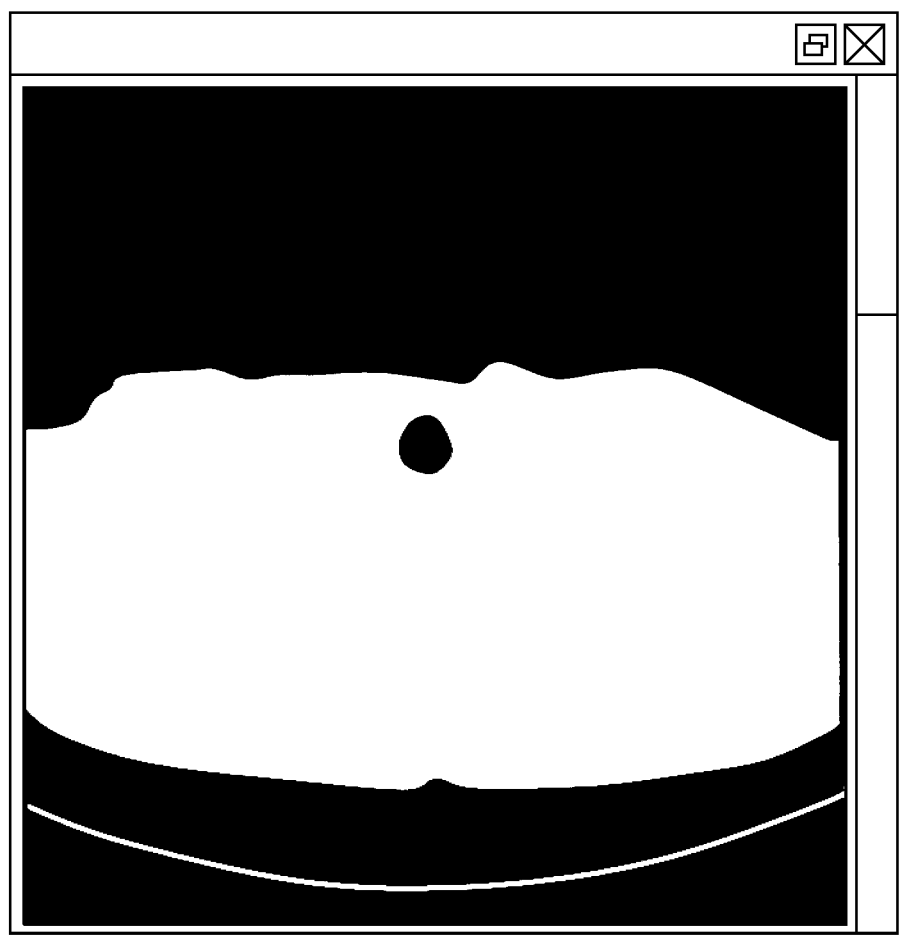
FIG. 47 is a diagram illustrating the first slice in chest CT imaging, and illustrates a slice image of a shoulder part which is nearer the head than the apex of the lung.

The user selects a series to be interpreted in the area 810. When the selection of the series is detected by the display control unit 104, as illustrated in FIG. 47, the initial slice image in the selected series is displayed in the display 101*a* (S570). FIG. 47 is a diagram illustrating a slice image displayed on the display 101*a* when a user selects a series. FIG. 47 is a diagram illustrating the first slice in chest CT imaging, and illustrates a slice image of a shoulder part which is nearer the head than the apex of the lung. The display control unit 104 displays all the slice images of the selected series in the display 101*a* in such a manner that the slice images can be forwarded on a series-by-series basis. No image is displayed on the display 101*b*. For example, the user inputs a slice-based forwarding operation which involves rotating the mouse wheel while the mouse pointer is on the display 101*a*, and the input operation is detected by the input control unit 103. Then, the display control unit 104 switches the slice image displayed on the display 101*a* to a slice image corresponding to another slice position in accordance with the amount of rotation of the mouse wheel. The user performs image-based diagnosis while inputting a slice-based forwarding operation. When confused about image-based diagnosis, the user starts the similar case search application.

The similar case search application may be started in response to the input of a predetermined shortcut key on the keyboard of the operation unit 102, or may be started by specifying a similar case search menu from a medical image viewer menu which is displayed in response to the right click of the mouse. When an instruction is given to start the similar case search application, the management of the information terminal 100 is passed to the ROI management unit 105, and the information terminal 100 waits for a region of interest (ROI) to be received.

Figure 25:
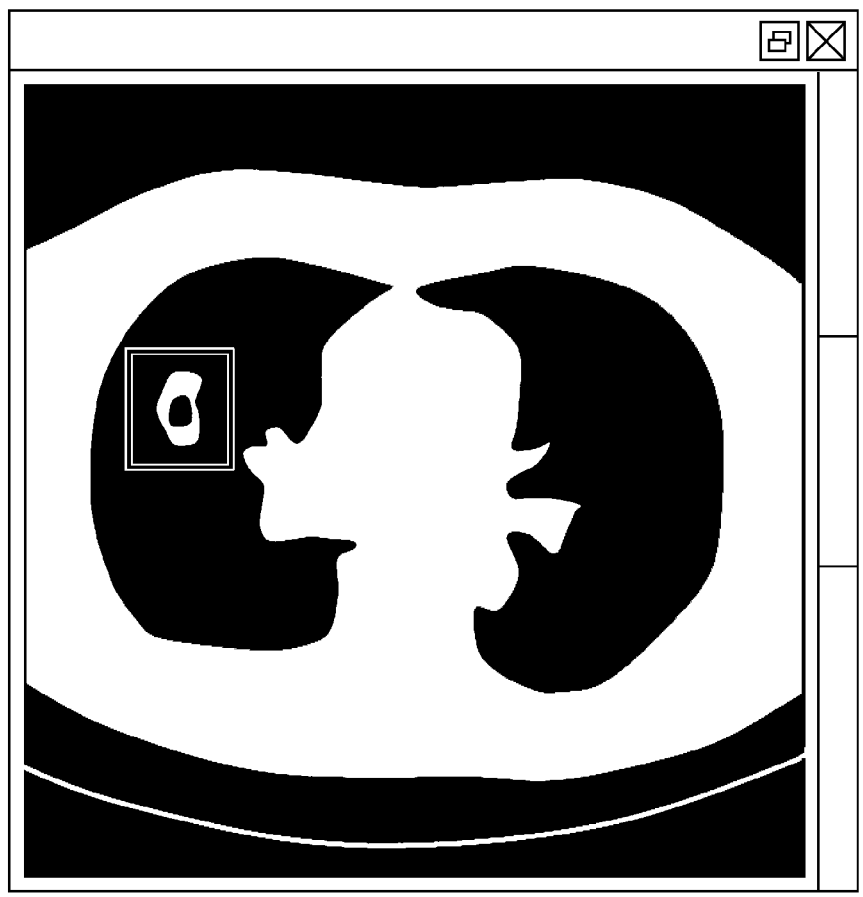
FIG. 25 illustrates an example of a screen obtained after a region of interest is set on a lesion.

The user sets a region of interest (ROI) on a lesion in the slice image displayed on the display 101*a* through the operation unit 102 (S580). As illustrated in FIG. 21, the user may enter the coordinates of the upper left corner of the region of interest by, for example, left-clicking on the mouse. Then, the user may enter the coordinates of the lower right corner of the region of interest by dragging the mouse diagonally down from left to right while left-clicking on the mouse and then by releasing the left click. FIG. 25 illustrates an example of a screen obtained after a region of interest is set on a lesion.

When the input control unit 103 detects the operation of setting a region of interest, the ROI management unit 105 receives coordinate data of the upper left and lower right corners of the region of interest from the input control unit 103, and generates region-of-interest information by using the received coordinate data. Then, the ROI management unit 105 transmits the generated region-of-interest information to the communication control unit 110 (S590).

Also, the ROI management unit 105 transmits the slice image of the case to be diagnosed to the communication control unit 110 (S600). In this case, one slice image (i.e., a search query image) in which the user has set a region of interest in the series selected by the user among the slice images of all the series received by the information terminal 100 from the medical information management system 200 in S550 is transmitted.

Then, the communication control unit 110 receives the region-of-interest information transmitted from the ROI management unit 105, and transmits the region-of-interest information to the communication control unit 304 of the case search system 300 (S601).

Also, the communication control unit 110 receives the slice image transmitted from the ROI management unit 105, and transmits the slice image to the communication control unit 304 of the case search system 300 (S602).

In S600 and S601, a slice image itself is transmitted. The slice ID of a slice image may be transmitted instead. In this case, upon receipt of the slice ID, the case search system 300 may acquire a slice image from the medical information management system 200 by specifying the slice ID.

Next, a process in which the case search system 300 performs a similar case search and the information terminal 100 initially displays similar case search results will be described.

Figure 26:
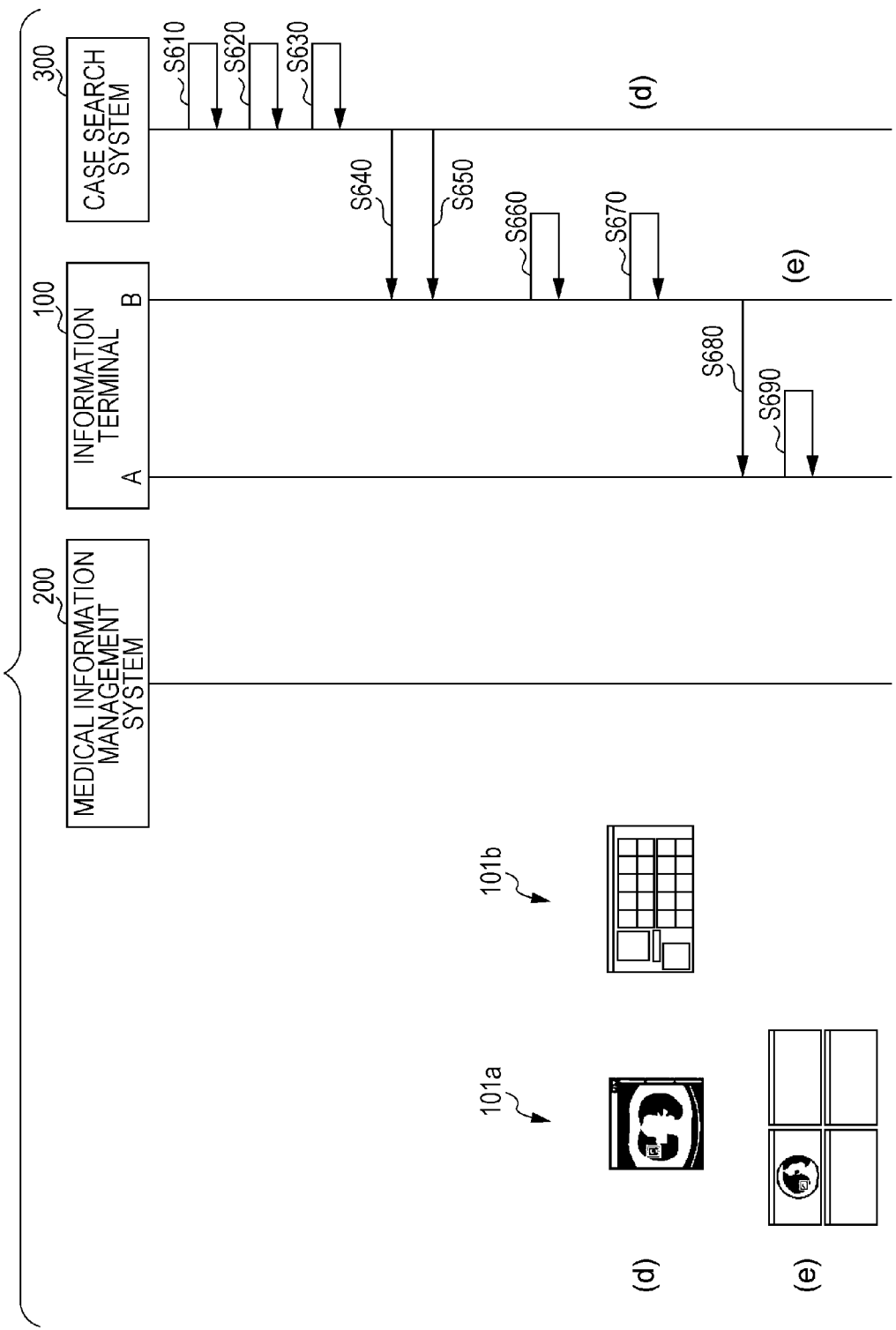
FIG. 26 is a sequence diagram illustrating a process in which, after receiving a similar case search request, the case search system returns similar case search results to the information terminal.

FIG. 26 is a sequence diagram illustrating a process in which, after receiving a similar case search request, the case search system 300 returns similar case search results to the information terminal 100.

The image feature extraction unit 302 of the case search system 300 extracts predetermined multi-dimensional image features from the region of interest set in the search query image (S610).

Examples of the "image features" include image features for the shape of organs or lesions in medical images, and image features for a luminance distribution. For example, NEMOTO et al. describes, in "Improvement of Tumor Detection Performance in Mammograms by Feature Selection from a Large Number of Features and Proposal of Fast Feature Selection Method", the transactions of the Institute of Electronics, Information and Communication Engineers D-II, Vol. J88-D-II, No. 2, pp. 416-426, February 2005, the use of 490-dimensional image features. In this embodiment, for example, the image features described in this non-patent literature are used. However, this is merely an example, and other image features may be used.

The similar case search unit 303 compares the image feature extracted by the image feature extraction unit 302 with an image feature in each of the similar cases accumulated in the similar case data accumulation unit 301 (S620). The similar case search unit 303 compares the two image features by calculating a distance between image feature data extracted from the search query image and the image feature data 4400 registered in the similar case data 4000 (FIG. 20) accumulated for each similar case in the similar case data accumulation unit 301.

Then, the similar case search unit 303 sorts similar cases for which the distance is less than or equal to a predetermined threshold value in order of increasing distance, and determines the resulting similar cases as similar cases to be transmitted (S630). Then, the communication control unit 304 transmits, within the similar case data 4000 of the similar cases determined to be transmitted, which is accumulated in the similar case data accumulation unit 301, the similar case ID 4100, the slice ID 4200, the region-of-interest information 4300, the thumbnail image data 4500, the distribution-of-lesion information 4600, the definite diagnosis (major-category disease name) 4700, and the definite diagnosis (subcategory disease name) 4800, and further the distance calculated by the similar case search unit 303 to the information terminal 100 (S640).

Subsequently, a process for generating the initial basic screen K2 (FIG. 6) on which similar case search results are displayed is executed. First, management information used to generate the layout area 720 on the initial basic screen K2 will be described.

First, the communication control unit 304 of the case search system 300 transmits layout information to the information terminal 100 (S650). The layout information is information for specifying the number of rows and columns of display boxes in the layout area 720.

Then, when the communication control unit 110 of the information terminal 100 receives the layout information, the display box management unit 106 registers the number of rows and columns of display boxes, which is specified in the transmitted layout information, in the display box management information 4410 (FIG. 35), and also registers the slice ID of the search query image in the display box management information 4410 (FIG. 35) (S660).

FIG. 35 is a diagram illustrating the data configuration of the display box management information 4410. The display box management information 4410 includes a table 4411 in which the number of rows and the number of columns are registered, and a table 4412 in which the slice ID of a slice image to be displayed in each display box is registered. Accordingly, the display box management unit 106 registers the number of rows and the number of columns, which are specified in the layout information transmitted from the case search system 300, in a number-of-row field and a number-of-column field of the table 4411. In this embodiment, the thumbnail image of the search query image is displayed in the upper left display box 721 among the four display boxes 721 to 724. The display box management unit 106 registers the slice ID of the search query image transmitted from the medical information management system 200 in the "first row and first column" item of the table 4412.

The default value of the number of rows and columns of display boxes in the layout area 720 is set in advance by the case search system 300. For example, the default values of the number of rows and the number of columns are two and two, respectively. Thus, "two rows and two columns" is registered in the display box management information 4410 illustrated in FIG. 35.

Then, the display control unit 104 generates the initial basic screen K2 on which similar case search results are displayed, by using the similar case data transmitted in S640 and the display box management information 4410 stored in S660 (S670).

In this case, the basic screen K2 illustrated in FIG. 6 is displayed on the display 101*b*. Further, the search query image is displayed on the display 101*a*.

Figure 27:
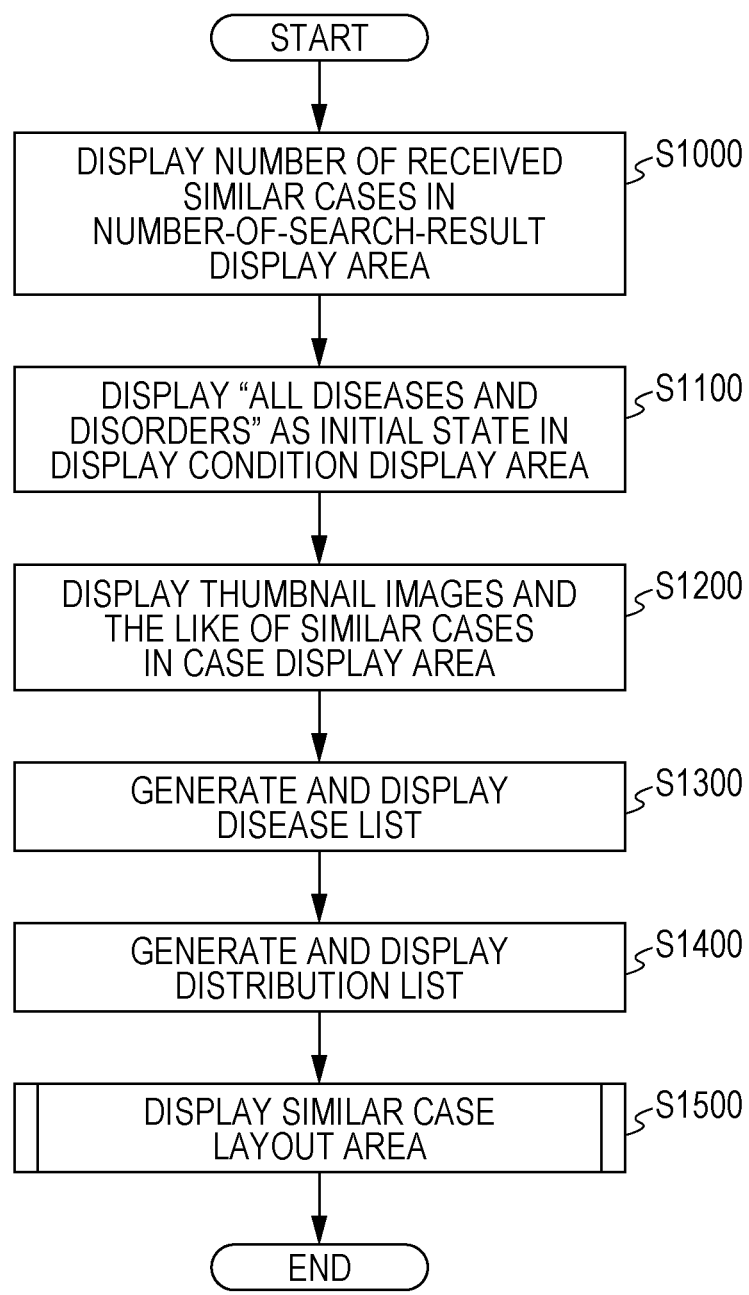
FIG. 27 is a flowchart illustrating the details of a process for generating an initial basic screen illustrated in S670 in FIG. 26.

FIG. 27 is a flowchart illustrating the details of the process for generating the initial basic screen K2 illustrated in S670 in FIG. 26.

First, in S1000, the display control unit 104 counts the number of similar cases received in S640 in FIG. 26, and displays the count value in the number-of-search-result display area 713.

Then, in S1100, the display control unit 104 displays "all diseases and disorders" in the display condition display area 714. Here, "all diseases and disorders" is displayed because no refinement is performed in accordance with a disease name or a distribution of lesions by the user on the initial basic screen K2.

Then, in S1200, the display control unit 104 displays in the case display area 710 thumbnail images of similar cases, the number of which is equal to the number of similar cases whose thumbnail images can be displayed in the case display area 710 among the similar cases received in S640 in FIG. 26, and also displays definite diagnoses and similarities in association with the respective thumbnail images.

In the example illustrated in FIG. 6, the maximum number of similar cases that can be displayed in the case display area 710 is 20. The maximum number of similar cases that can be displayed is determined in advance. The maximum number of similar cases that can be displayed may also be changed as desired by the user. If the number of similar cases received in S640 in FIG. 26 is larger than the maximum number of similar cases that can be displayed, the display control unit 104 displays the vertical scrollbar 715 at the right end of the case display area 710. By moving the scrollbar 715, the user is able to view the thumbnail images of similar cases that are not currently visible on the initial basic screen K2.

Then, in S1300, a disease list is generated and displayed. First, a disease list is generated based on the similar cases received in S640 in FIG. 26. The disease list is a list in which the similar cases received in S640 are classified by each definitely diagnosed disease name.

It is assumed here that the number of similar cases received in S640 is represented by NC. The disease list management unit 108 generates a disease list by using the definite diagnosis (major-category disease name) 4700 and the definite diagnosis (subcategory disease name) 4800 registered in each of the NC pieces of similar case data 4000.

The generated disease list is managed by the disease list management unit 108 as data in table format, as illustrated in FIG. 29.

FIG. 29 is a diagram illustrating the data configuration of the disease list generated in S1300 in FIG. 27. The disease list includes the following fields: "disease ID", "major-category disease name", "subcategory disease name", "number of results", and "similar case ID". The "disease ID" field represents a disease ID that is an identifier assigned to each definitely diagnosed disease name. Here, a disease ID is assigned to a combination of major-category and subcategory disease names.

The "major-category disease name" field represents the name of a definitely diagnosed disease indicated by the definite diagnosis (major-category disease name) 4700 registered in the similar case data 4000. The "subcategory disease name" field represents the name of a definitely diagnosed disease indicated by the definite diagnosis (subcategory disease name) 4800 registered in the similar case data 4000. The "number of results" field represents the number of similar cases corresponding to the definitely diagnosed disease name identified by the "disease ID". The "similar case ID" field represents a similar case ID that identifies a similar case corresponding to the disease name identified by the "disease ID".

The disease list management unit 108 extracts the definite diagnosis (major-category disease name) 4700 and the definite diagnosis (subcategory disease name) 4800 in each of the pieces of similar case data 4000 received in S640, and classifies pieces of similar case data 4000 having the same definite diagnosis (major-category disease name) 4700 and the same definite diagnosis (subcategory disease name) 4800 as pieces of similar case data indicating similar cases of the same definitely diagnosed disease. Further, the disease list management unit 108 counts the number of similar cases corresponding to the same definitely diagnosed disease name, and registers the number of similar cases in the "number of results" field of the record of the corresponding definitely diagnosed disease name. The disease list management unit 108 also registers the similar case IDs of the similar cases classified as the same definitely diagnosed disease name in the "similar case ID" field of the record of the corresponding definitely diagnosed disease name.

In the example illustrated in FIG. 29, the disease ID "DIS528" is assigned to the definitely diagnosed disease name categorized as the major-category disease name "neoplastic" and the subcategory disease name "lung cancer". The number of similar cases corresponding to this definitely diagnosed disease name is 10. Thus, "10" is registered in the "number of results" field of the corresponding record, and the similar case IDs "SIM258", "SIM551", "SIM1209", "SIM2341", and so forth of the similar cases corresponding to this definitely diagnosed disease name are registered in the "similar case ID" field of the corresponding record.

The display control unit 104 generates the disease list display area 730 by using the disease list generated in the way described above, and displays the disease list display area 730 on the display 101.

FIG. 30, FIG. 31, and FIG. 32 are diagrams illustrating a first example display, a second example display, and a third example display of the disease list display area 730, respectively. As illustrated in FIG. 30, in the first example display, subcategory disease names are displayed in list form in association with the numbers of similar cases corresponding thereto, which are obtained as a result of the similar case search, according to the decreasing number of similar cases.

As illustrated in FIG. 31, in the second example display, major-category disease names are displayed in list form in association with the numbers of similar cases corresponding thereto, which are obtained as a result of the similar case search, according to the decreasing number of similar cases.

As illustrated in FIG. 32, in the third example display, major-category disease names are displayed in list form in association with the numbers of similar cases corresponding thereto, which are obtained as a result of the similar case search, according to the decreasing number of similar cases, and subcategory disease names included in each of the major-category disease names are further displayed in list form in association with the numbers of similar cases corresponding thereto according to the decreasing number of similar cases. In this case, each definitely diagnosed disease name is expressed using a hierarchical structure of a major-category disease name and a subcategory disease name.

Figure 33:
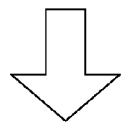
FIG. 33 is a diagram illustrating a screen transition in the disease list display area illustrated in FIG. 31.

FIG. 33 is a diagram illustrating a screen transition in the disease list display area 730 illustrated in FIG. 31. As illustrated in the upper part of FIG. 33, when the input control unit 103 detects the selection of a major-category disease name by the user among the major-category disease names displayed in list form, as illustrated in the lower part of FIG. 33, the display control unit 104 displays the subcategory disease names that belong to the selected major-category disease name in association with the numbers of similar cases corresponding thereto according to the decreasing number of similar cases. In this case, the user may select a desired major-category disease name from among, for example, the major-category disease names displayed in list form in the disease list display area 730 by, for example, double clicking or single clicking. In the example illustrated in FIG. 33, "nonneoplastic" is double-clicked. Thus, subcategory disease names that belong to "nonneoplastic" are displayed in list form.

In the lower part of FIG. 33, when an area showing a list of subcategory disease names is double-clicked or single-clicked by the user, the display control unit 104 may hide the subcategory disease names displayed in the area.

The display control unit 104 may determine subcategory disease names that belong to a major-category disease name by referring to the disease list (FIG. 29). For example, in the example illustrated in FIG. 29, aspergillosis and cryptococcosis are associated with mycosis. Thus, the display control unit 104 may determine that aspergillosis and cryptococcosis belong to mycosis.

In the example FIG. 30 to in FIG. 33, one disease name is selected by way of example. Alternatively, a plurality of disease names may be simultaneously selected. In the example illustrated in FIG. 30, the user may select a plurality of disease names among the subcategory disease names displayed in list form by single clicking or double clicking on the items of a plurality of disease names while pressing a predetermined key (e.g., the Ctrl key or the shift key) on the keyboard. In this case, as illustrated in FIG. 49, sub-areas are created in the case display area 710 for the respective subcategory disease names selected by the user, and thumbnail images are displayed so as to be aligned in a column in each of the sub-areas.

In the example illustrated in FIG. 31, furthermore, major-category disease names are displayed in list form. When a plurality of disease names are selected through the operation described above, as illustrated in FIG. 49, sub-areas are created in the case display area 710 for the respective selected major-category disease names, and thumbnail images are displayed so as to be aligned in a column in each of the sub-areas.

In the example illustrated in FIG. 32, major-category disease names and subcategory disease names are simultaneously displayed. This enables the user to simultaneously select both a major-category disease name and a subcategory disease name through the operation described above. In this case, if the user selects a certain major-category disease name (e.g., mycosis), the user is able to select one or more subcategory disease names (e.g., lung cancer) from among the subcategory disease names that belong to major-category disease names other than the selected major-category disease name. If the user selects a certain subcategory disease name (e.g., lung cancer), the user is able to select one or more major-category disease names (e.g., mycosis) other than the major-category disease name to which the selected subcategory disease name belongs. In this case, a sub-area is created in the case display area 710 for each of the major-category disease name and subcategory disease name selected by the user, and thumbnail images are displayed in each sub-area.

In the example illustrated in the upper part of FIG. 33, major-category disease names are displayed in list form. Thus, the user is able to simultaneously select a plurality of major-category disease names through the operation described above. In the example illustrated in the lower part of FIG. 33, major-category disease names and subcategory disease names are concurrently displayed. Thus, the user is able to simultaneously select both a major-category disease name and a subcategory disease name through the operation described above.

Referring back to FIG. 27, in S1400, a distribution list is generated and displayed. First, a distribution list is generated based on the similar cases received in S640. The distribution list is a list in which the similar cases received in S640 are classified by the distribution of lesions.

The disease list management unit 108 generates a distribution list by using the distribution-of-lesion information 4600 registered in each of the NC pieces of similar case data 4000. The generated distribution list is managed by the distribution list management unit 109 as data in table format, as illustrated in FIG. 34.

FIG. 34 is a diagram illustrating the data configuration of the distribution list generated in S1400 in FIG. 27. The distribution list includes the following fields: "name of distribution", "number of cases", and "similar case ID". The "name of distribution" field represents the names of a plurality of predetermined distributions of lesions such as diffuse and segmental distributions. The "number of cases" field represents the number of similar cases corresponding to each distribution of lesions. The "similar case ID" field represents a similar case ID that identifies a similar case corresponding to each distribution of lesions.

The distribution list management unit 109 extracts the distribution-of-lesion information 4600 in each of the pieces of similar case data 4000 received in S640, counts the number of distributions of lesions with the distribution flag value set to "1" (Applicable) in the extracted distribution-of-lesion information 4600, and registers the count value in the "number of cases" field of the record of the corresponding distribution of lesions. The distribution list management unit 109 also registers the similar case IDs of the similar cases with the distribution flag value set to "1" in the "similar case ID" field of the record of the corresponding distribution of lesions.

In the example illustrated in FIG. 34, the number of similar cases corresponding to the diffuse distribution is three. Thus, "3" is registered in the "number of cases" field of the record of the diffuse distribution. Further, the similar case IDs "SIM2521", "SIM4123", "SIM5225", and so forth of the similar cases corresponding to the diffuse distribution are registered in the "similar case ID" field of the record of the diffuse distribution.

The display control unit 104 generates the distribution list display area 750 by using the distribution list generated in the way described above, and displays the distribution list display area 750 on the display 101.

FIG. 11 illustrates the distribution list display area 750 generated using the distribution list illustrated in FIG. 34. In FIG. 34, the number of cases corresponding to the segmental and subpleural distributions is 0. Accordingly, the "segmental" 752 and the "subpleural" 756 are displayed as inactive in FIG. 11. The number of cases corresponding to the other distributions of lesions is greater than or equal to one, and such distributions of lesions are displayed as active accordingly.

Referring back to FIG. 27, in S1500, the layout area 720 is displayed. This process is performed by the display control unit 104.

Figure 28:
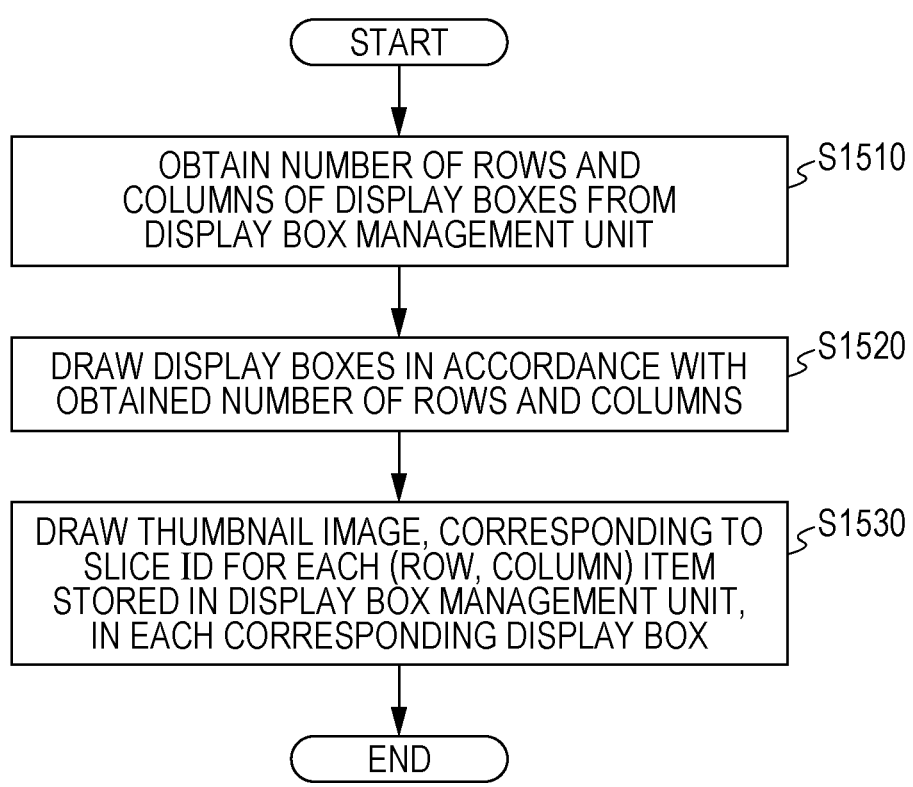
FIG. 28 is a flowchart illustrating the processing of S1500 illustrated in FIG. 27.

FIG. 28 is a flowchart illustrating the processing of S1500 illustrated in FIG. 27. In S1510, the display control unit 104 obtains the number of rows and columns of display boxes in the layout area 720 from the display box management information 4410 set in S660. In the example of the display box management information 4410 illustrated in FIG. 35, the number of rows and the number of columns are set to two and two, respectively. Thus, information indicating "two rows and two columns" is obtained.

Then, in S1520, the display control unit 104 draws display boxes in accordance with the number of rows and columns obtained in S1510.

Finally, in S1530, the display control unit 104 identifies a slice ID for each display box from the display box management information 4410, and draws a thumbnail image corresponding to the identified slice ID in the corresponding one of the display boxes.

In the example illustrated in FIG. 35, the slice ID of the case to be diagnosed is stored in the display box in the first row and the first column. Accordingly, the display control unit 104 generates a thumbnail image from the slice image of the case to be diagnosed, which is transmitted in S600 in FIG. 22, and draws the generated thumbnail image in the display box 721.

In this stage, no slice IDs are stored in the other display boxes (i.e., the display boxes 722, 723, and 724 in the first row and the second column, the second row and the first column, the second row and the second column, respectively). Thus, the display control unit 104 displays no images in these display boxes. A thumbnail image of a similar case is displayed in these display boxes through a process described below.

Referring back to FIG. 26, the communication control unit 110 transmits the display box management information 4410 stored in the display box management unit 106 to the display control unit 104 (S680).

Then, the display control unit 104 starts a medical image viewer in the same display state and layout as the display state and layout of the layout area 720 (S690).

Figure 36:
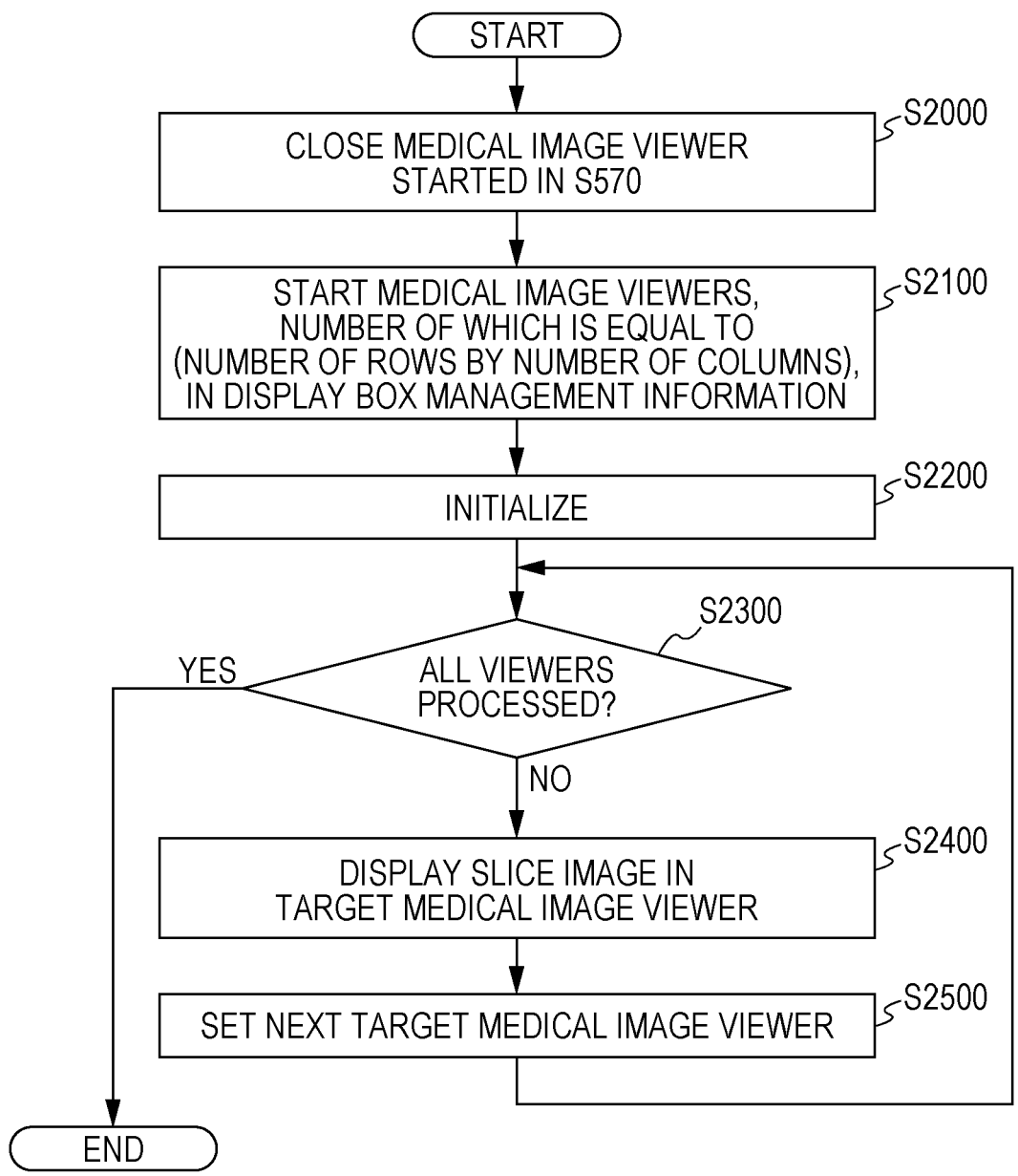
FIG. 36 is a flowchart illustrating a medical image viewer starting process.

FIG. 36 is a flowchart illustrating a medical image viewer starting process.

In S2000, the display control unit 104 closes the medical image viewer started in S570 in FIG. 22.

In S2100, the display control unit 104 starts medical image viewers corresponding to the display boxes registered in the display box management information 4410, with the layout of the rows and columns registered in the display box management information 4410. In the display box management information 4410 illustrated in FIG. 35, two rows and two columns of display boxes, that is, four display boxes, are registered. Accordingly, as illustrated in FIG. 5, the display control unit 104 starts the four medical image viewers 610 to 640 which are arranged in a grid of two rows and two columns.

In S2200, the display control unit 104 initializes a variable for identifying a target medical image viewer to be processed. Here, the medical image viewer in the first row and the first column is a target to be processed. Thus, the variable is set to the first row and first column.

In S2300, the display control unit 104 determines whether or not the processing for all (here, four) medical image viewers is completed. If the processing is completed (YES in S2300), the process ends. If there is any medical image viewer yet to be processed (NO in S2300), the process proceeds to S2400.

In S2400, the display control unit 104 displays a slice image having the slice ID associated with the row and column set as the variable in the target medical image viewer, and associates the series including the slice ID with the target medical image viewer.

For example, in the example of the display box management information 4410 illustrated in FIG. 35, the slice ID "CT12353515" is registered for the first row and the first column. Accordingly, the slice ID "CT12353515" is displayed in the medical image viewer 610. The display control unit 104 further draws a rectangular region indicating the region of interest set in the initially displayed slice image so that the rectangular region overlaps the slice image. The series including the slice ID registered for the first row and the first column is obtained in S550 in FIG. 22. In addition, the region of interest is set in S580 in FIG. 22.

Referring back to FIG. 36, in S2500, the next medical image viewer is set as the target medical image viewer to be processed. The target to be processed is set in such a manner that the medical image viewer in the first row and the first column is followed by, for example, the medical image viewers in the first row and the second column, the second row and the first column, and the second row and the second column in this order.

In the second loop, in S2400, the medical image viewer 620 in the first row and the second column is set as the target to be processed. In the display box management information 4410 illustrated in FIG. 35, no slice IDs are associated with the medical image viewers other than that in the first row and the first column. Thus, the display control unit 104 performs no processing on the medical image viewer in the first row and the second column, and makes it blank. The same applies to the medical image viewer 630 in the second row and the first column and the medical image viewer 640 in the second row and the second column.

At the end of the flowchart, the initial basic screen K1 illustrated in FIG. 5 is displayed on the display 101*a*. The search query image is displayed in the medical image viewer 610 in the first row and the first column (upper left), and the region of interest is further drawn so as to overlap the search query image.

Figure 37:
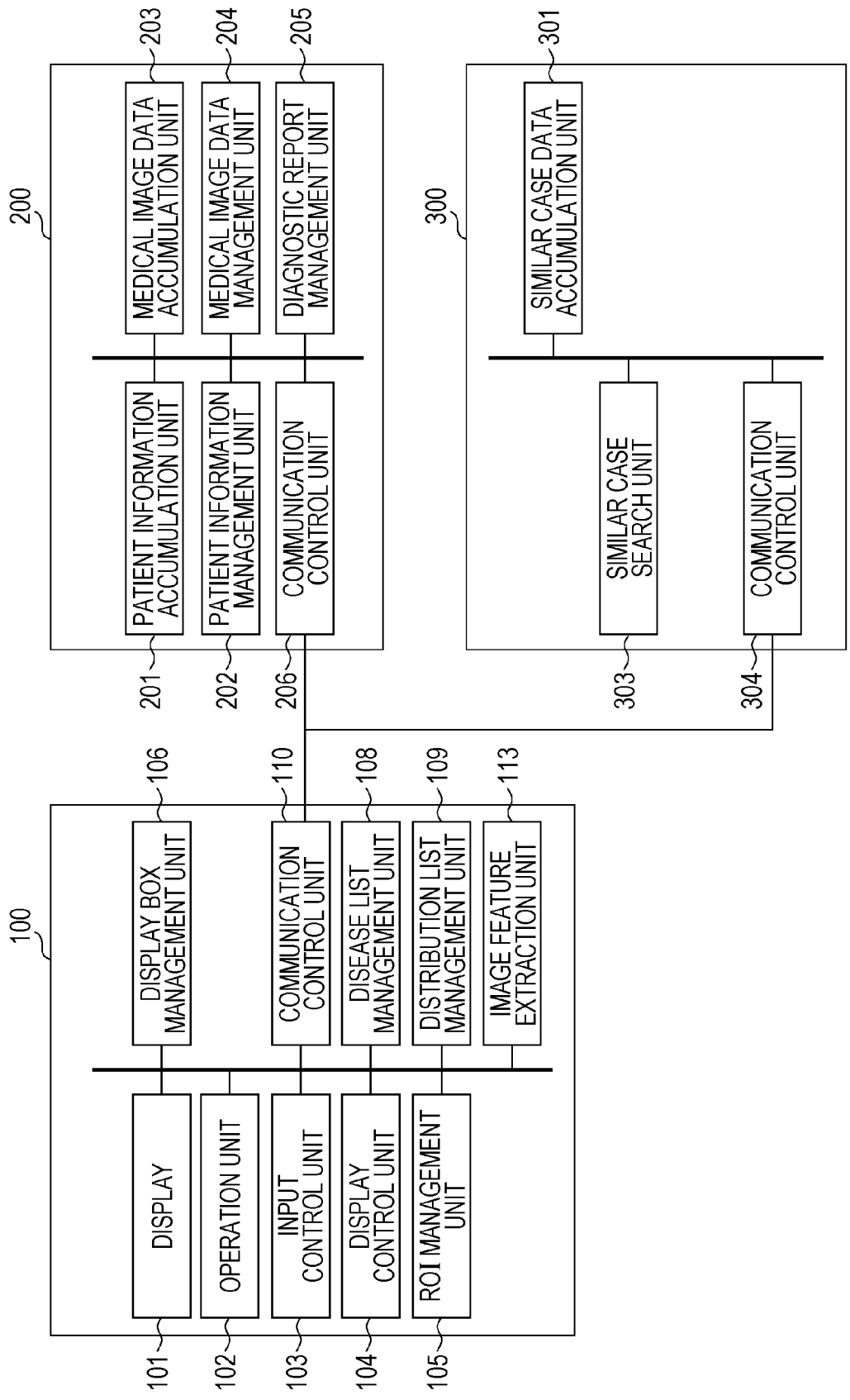
FIG. 37 is a block diagram of an information terminal, a medical information management system, and a case search system according to an embodiment in which the case search system extracts an image feature.

In the illustrated example, the case search system 300 extracts an image feature. Alternatively, the information terminal 100 may extract an image feature. FIG. 37 is a block diagram of the information terminal 100, the medical information management system 200, and the case search system 300 according to an embodiment in which the case search system 300 extracts an image feature.

The configuration illustrated in FIG. 37 is different from that illustrated in FIG. 2 in that the information terminal 100 further includes an image feature extraction unit 113 and the case search system 300 does not include the image feature extraction unit 302.

Figure 38:
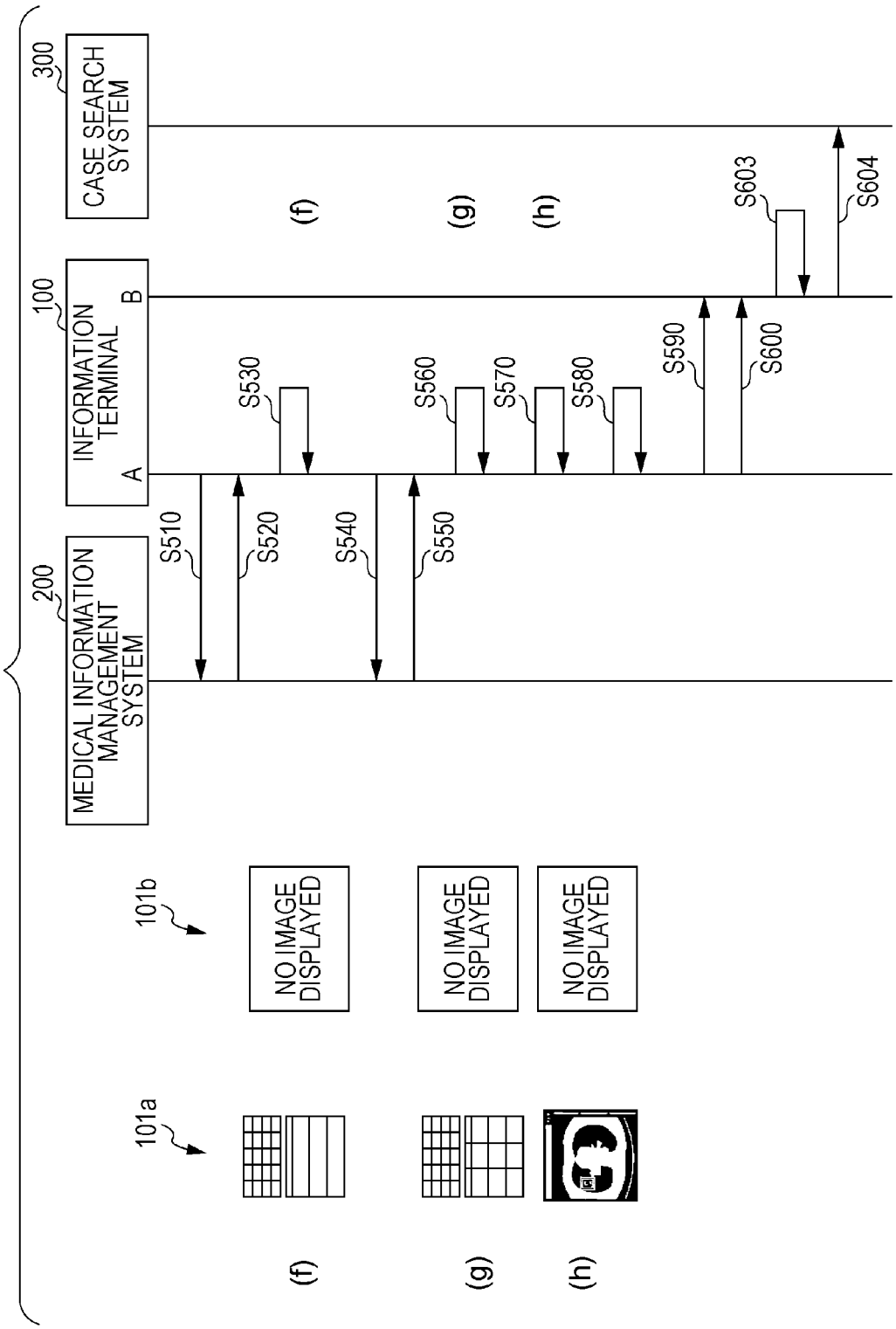
FIG. 38 is a sequence diagram illustrating a process in which the information terminal obtains a case to be diagnosed from the medical information management system and thereafter the case search system receives a similar case search request.

FIG. 38 is a sequence diagram illustrating a process in which the information terminal 100 obtains a case to be diagnosed from the medical information management system 200 and thereafter the case search system 300 receives a similar case search request.

The operation illustrated in FIG. 38 is different from that illustrated in FIG. 22 in that, after the ROI management unit 105 transmits a slice image of the case to be diagnosed to the communication control unit 110 (S600), the information terminal 100 extracts an image feature (S603) and transmits the extracted image feature to the case search system 300 (S604). The process for extracting an image feature (S604) is similar to that in the case where the case search system 300 extracts an image feature.

Figure 39:
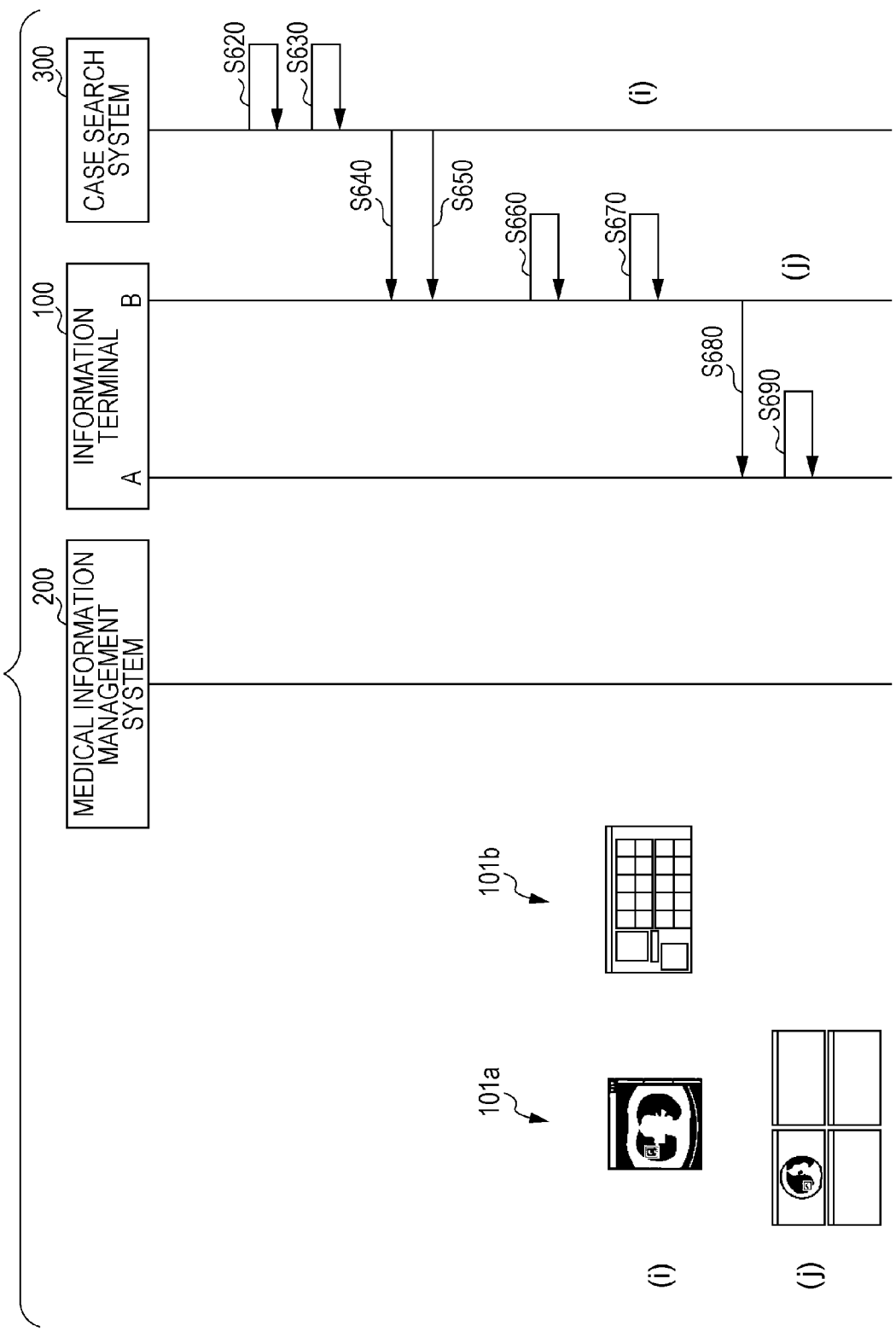
FIG. 39 is a sequence diagram illustrating a process in which, after receiving the similar case search request, the case search system returns similar case search results to the information terminal.

FIG. 39 is a sequence diagram illustrating a process in which, after receiving the similar case search request, the case search system 300 returns similar case search results to the information terminal 100. The operation illustrated in FIG. 39 is different from that illustrated in FIG. 26 in that, since an image feature is extracted by the information terminal 100, the extraction of an image feature (S610) in FIG. 26 is omitted in FIG. 39.

Figure 40:
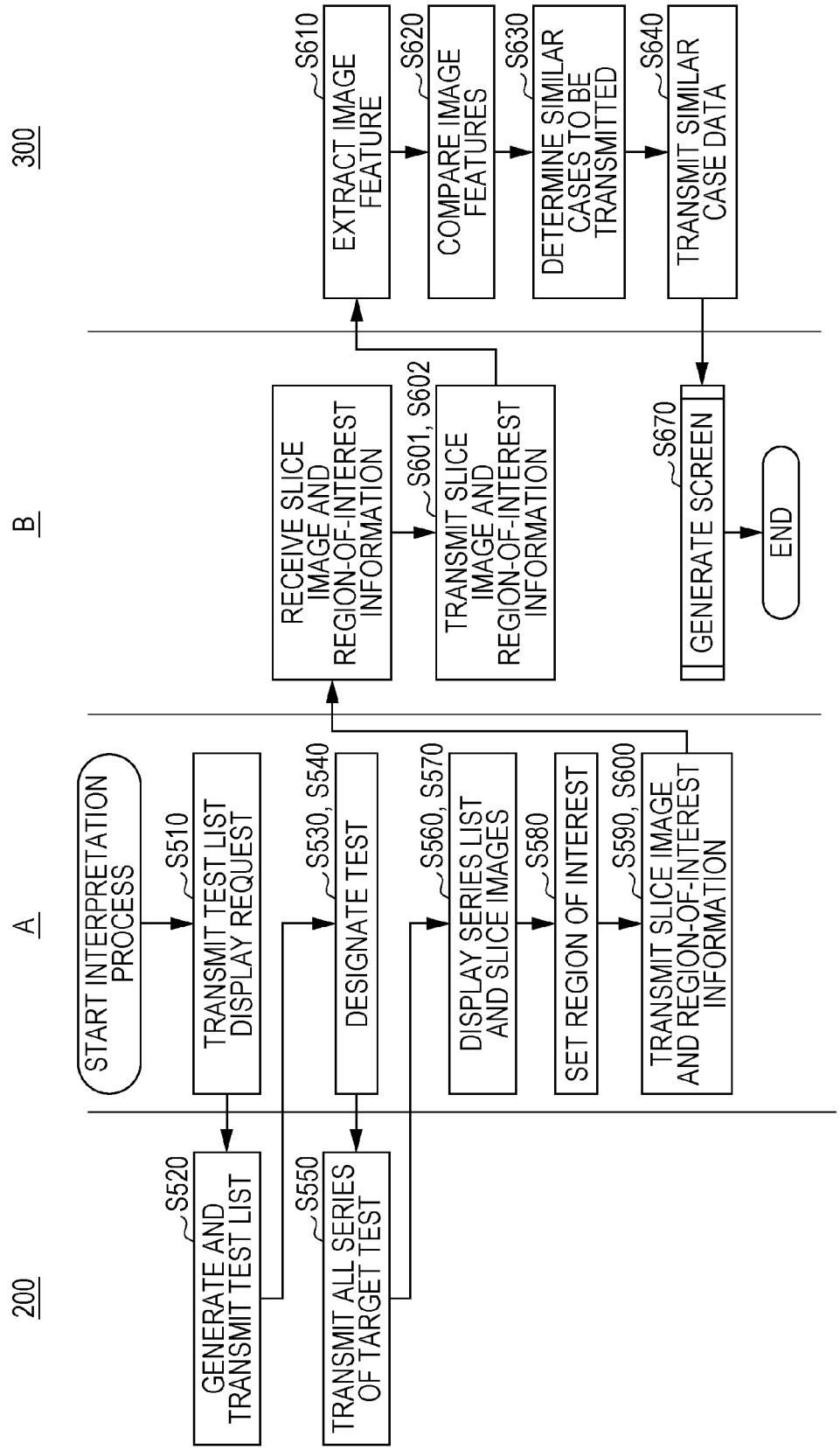
FIG. 40 is a sequence diagram focusing on the sequence diagrams illustrated in FIG. 22 and FIG. 26 at the application level.

Next, the process performed by the information terminal 100, the medical information management system 200, and the case search system 300 when the focus is on the sequence diagrams illustrated in FIG. 22 and FIG. 26 at the application level will be described. FIG. 40 is a sequence diagram focusing on the sequence diagrams illustrated in FIG. 22 and FIG. 26 at the application level. In FIG. 40, substantially the same processing steps as those in FIG. 22 are assigned the same numerals.

In FIG. 40, part "A" illustrates the process of the medical information management application implemented by the information terminal 100, and part "B" illustrates the process of the similar case search application implemented by the information terminal 100. In the following, the medical information management application is represented by the "app A", and the similar case search application is represented by the "app B".

First, the app A accepts a request for displaying a test list for image interpretation from the user, and transmits the request to the medical information management system 200 (S510). Upon receipt of the request, the medical information management system 200 lists tests in which image interpretation is yet to be performed after the completion of an imaging test to generate a test list in which image interpretation is to be performed, and transmits the test list to the app A.

Upon receipt of the test list, the app A displays the test list as illustrated in FIG. 23 on the display 101. When the user selects a test from the test list (S530), the app A transmits a request for displaying the selected test to the medical information management system 200 (S540).

Upon receipt of the request for displaying the test, the medical information management system 200 transmits all the slice images of all the series included in the test ID specified in the request to the app A (S550).

Then, the app A displays a series list as illustrated in FIG. 24 in which pieces of information concerning all the series included in the specified test ID are displayed in list form (S560).

Then, when a series to be interpreted is selected by the user from the series list, the app A displays the slice image corresponding to the initial slice position in the selected series in the medical image viewer 610 (S570). In this case, the user inputs a slice-based forwarding operation to display the desired slice image in the medical image viewer 610.

Then, the app A accepts an operation of setting a region of interest in the slice image displayed in the medical image viewer 610 from the user (S580).

Then, the app A generates region-of-interest information indicating the region of interest set by the user, and transmits the region-of-interest information together with the slice image in which the region of interest has been set (i.e., the slice image of the case to be diagnosed) to the app B (S590, S600).

Upon receipt of the slice image of the case to be diagnosed and the region-of-interest information, the app B transmits the slice image and the region-of-interest information to the case search system 300 (S601, S602).

Upon receipt of the slice image and the region-of-interest information, as in FIG. 26, the case search system 300 executes the processing of S610 to S640.

Then, the app B generates an initial basic screen by using the similar case data transmitted in S640 and the display box management information 4410 (S670). Then, the app B executes the processing of S670, the details of which are illustrated in FIG. 27.

Figure 41:
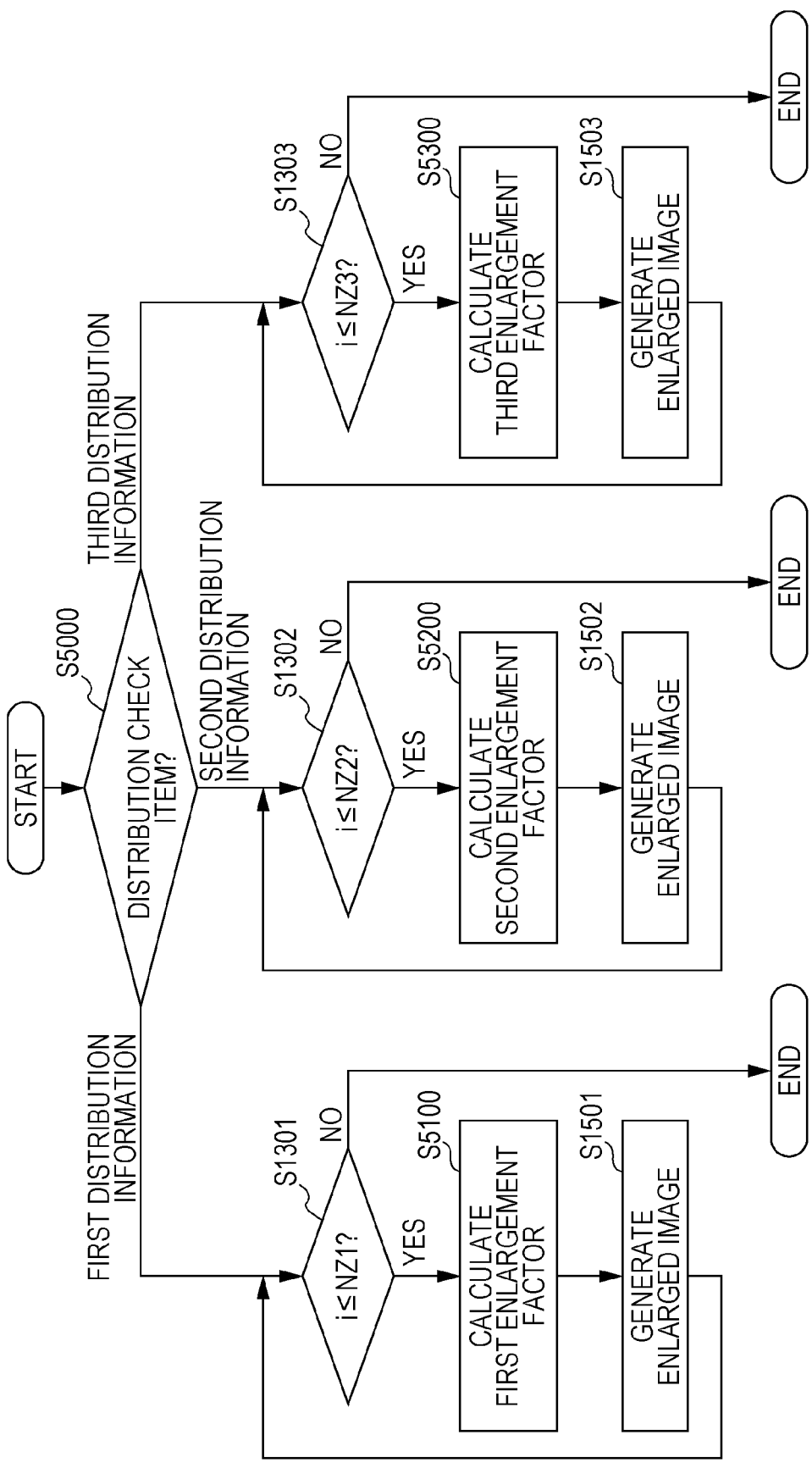
FIG. 41 is a flowchart illustrating a process performed when a distribution of lesions displayed in the distribution list display area is selected.

Next, a process performed when a distribution of lesions displayed in the distribution list display area 750 is selected illustrated in FIG. 11 will be described. FIG. 41 is a flowchart illustrating a process performed when a distribution of lesions displayed in the distribution list display area 750 is selected.

In S5000, when the input control unit 103 detects the operation of selecting a distribution check item from the distributions of lesions (or distribution check items) displayed in the distribution list display area 750, the display control unit 104 determines which of first distribution information, second distribution information, and third distribution information the detected distribution check item corresponds to. If the detected distribution check item corresponds to the first distribution information, the process proceeds to S1301. If the detected distribution check item corresponds to the second distribution information, the process proceeds to S1302. If the detected distribution check item corresponds to the third distribution information, the process proceeds to S1303.

The first distribution information is information for selection of thumbnail images that belong to a predetermined first range indicating that the size of the region of interest is wide relative to the lung area among the thumbnail images of the similar cases displayed in list form in the case display area 710. By way of example, the first distribution information includes "bilateral", "multiple", "diffuse", and "hematogenous". Accordingly, the first range is a range of values to which the size of the region of interest set for the diagnosis of such distributions of lesions belongs.

The second distribution information is information for selection of thumbnail images that belong to a predetermined second range (lower than the first range; the upper limit of the second range is less than or equal to the lower limit of the first range) indicating that the size of a region corresponding to the region of interest is part of the lung area among the thumbnail images of the similar cases displayed in list form in the case display area 710. By way of example, the second distribution information includes "bronchial" and "segmental". Accordingly, the second range is a range of values to which the size of the region of interest set for the diagnosis of such distributions of lesions belongs.

The third distribution information is information for selection of thumbnail images in which the region of interest includes a pleura among the thumbnail images of the similar cases displayed in list form in the case display area 710. By way of example, the third distribution information includes "subpleural".

In S1301, the display control unit 104 extracts similar cases, which are obtained as a result of the similar case search and the number of which is less than or equal to the maximum number of (in this embodiment, 20) thumbnail images that can be displayed in the case display area 710 among the similar cases corresponding to the distributions of lesions selected as the first distribution information by the user, in order of decreasing similarity, and determines the number of extracted similar cases as the number of similar cases NZ1 to be subjected to enlargement. The display control unit 104 further determines the thumbnail image of the extracted similar case i (where i is an index identifying an extracted similar case, and is an integer greater than or equal to 1) as a target thumbnail image to be processed. The display control unit 104 repeatedly performs the processing of S5100 and S1501 until the index i has reached the value NZ1. The display control unit 104 increments the index i by 1 each time the processing of S5100 and S1501 is executed. If the index i exceeds the value NZ1 (NO in S1301), the process ends.

In S5100, the display control unit 104 calculates a first enlargement factor for the first distribution information on the similar case i. By way of example, the first enlargement factor is 1.0. This is an example, and any value other than 1.0 may be used as the first enlargement factor as long as the entire region of interest set for the diagnosis of a distribution of lesions indicated by the first distribution information falls within the display area.

In S1501, the display control unit 104 enlarges the thumbnail image of the similar case i with the first enlargement factor for the similar case i.

Figure 42:
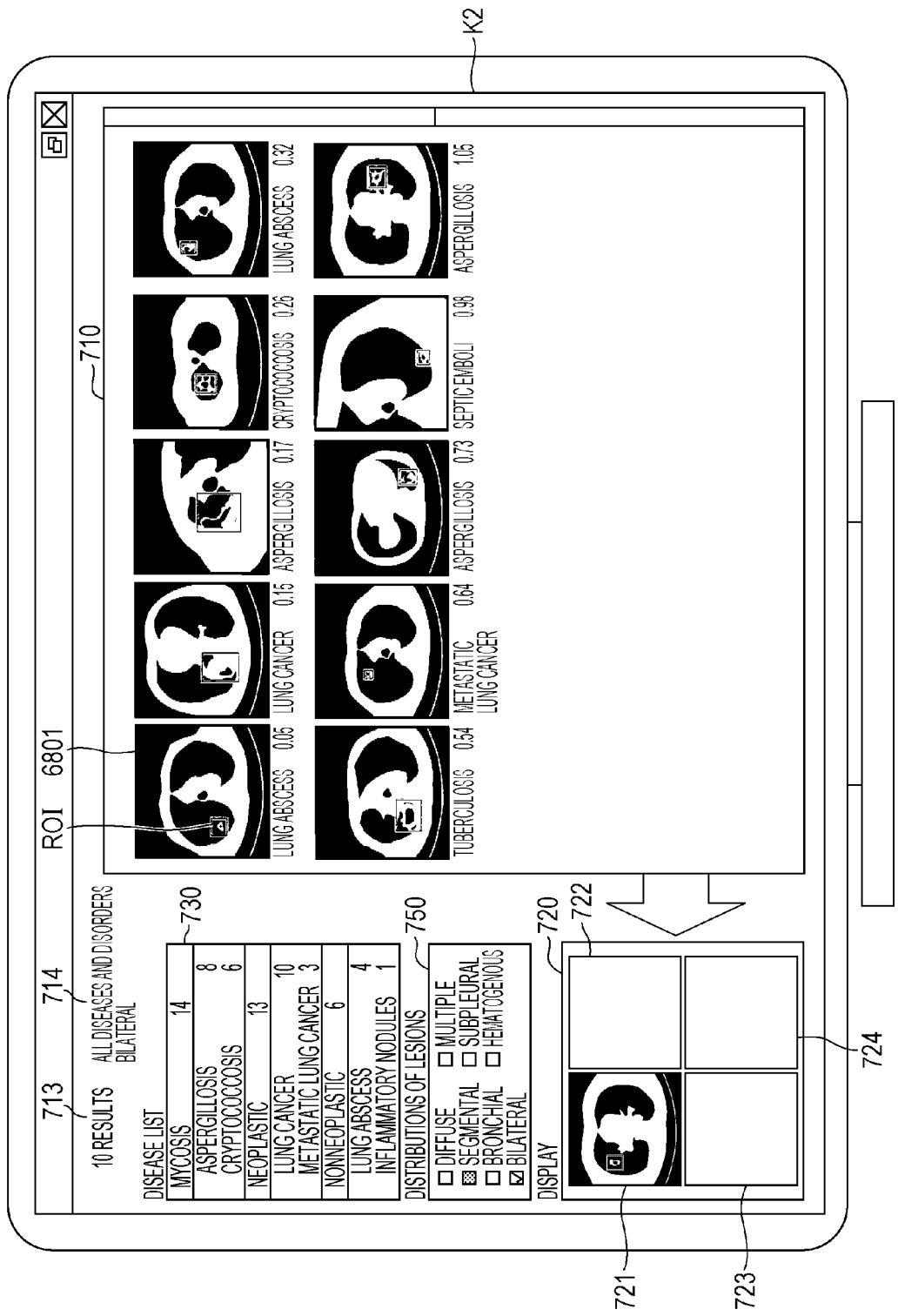
FIG. 42 is a diagram illustrating a basic screen on which the first distribution information is selected.

FIG. 42 is a diagram illustrating the basic screen K2 on which the first distribution information is selected. In FIG. 42, "bilateral" is selected. In this case, thumbnail images of similar cases corresponding to the bilateral distribution of lesions among the similar cases are displayed in the case display area 710. Since the enlargement factor is 1.0, the thumbnail images are displayed in the same display style as the thumbnail images displayed in the case display area 710 immediately after similar case search results are obtained. That is, the thumbnail images are displayed without adjusting the display positions of the thumbnail images so that the center of the region of interest ROI in each thumbnail image matches the center of a display area 6801 (an example of a display frame) or without enlarging the thumbnail images.

In S1302, the display control unit 104 extracts similar cases, which are obtained as a result of the similar case search and the number of which is less than or equal to the maximum number of thumbnail images that can be displayed in the case display area 710 among the similar cases corresponding to the distributions of lesions selected as the second distribution information by the user, in order of decreasing similarity, and determines the number of extracted similar cases as the number of similar cases NZ2 to be subjected to enlargement. The display control unit 104 further determines the thumbnail image of the extracted similar case i as a target thumbnail image to be processed. The display control unit 104 repeatedly performs the processing of S5200 and S1502 until the index i has reached the value NZ2. The display control unit 104 increments the index i by 1 each time the processing of S5200 and S1502 is executed. If the index i exceeds the value NZ2 (NO in S1302), the process ends.

In S5200, the display control unit 104 calculates a second enlargement factor for the second distribution information on the similar case i by using the size of a display area determined in advance for each thumbnail image in the case display area 710 and the region-of-interest information on the similar case i.

If the second distribution information is selected, the similar case i is enlarged so that the size of the region of interest is equal to approximately one half of the size of the display area. Accordingly, for example, the display control unit 104 calculates a second enlargement factor ki for the similar case i in accordance with the following equation:

$$ki = \tfrac{1}{2}(Sd/Si),$$

where Sd denotes the area of the display area and Si denotes the area of the region of interest in the thumbnail image of the similar case i to be subjected to enlargement.

In S1502, the display control unit 104 enlarges the thumbnail image of the similar case i with the second enlargement factor ki, and displays the thumbnail image in the case display area 710 so that the center of the region of interest in the thumbnail image matches the center of the display area.

Figure 43:
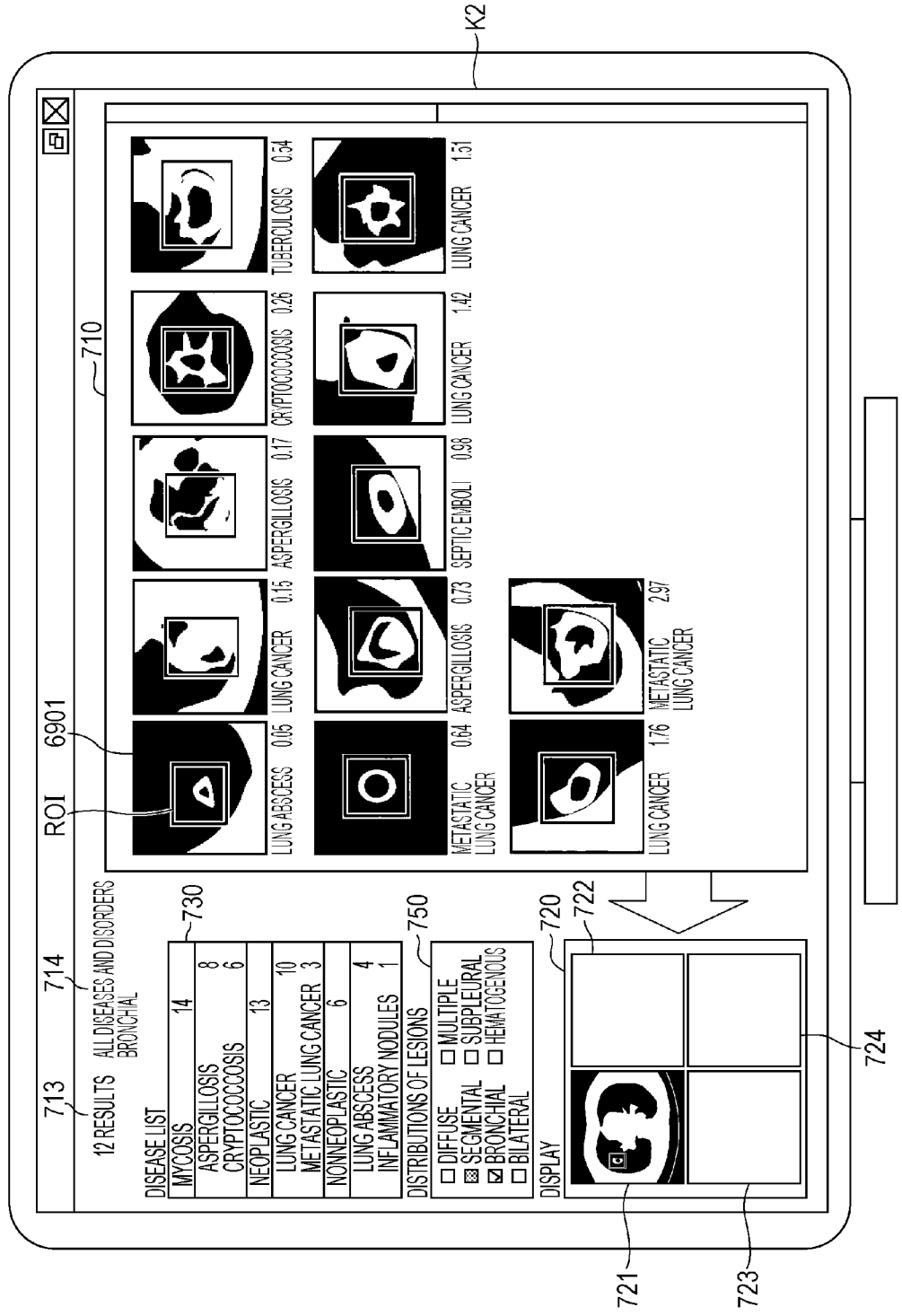
FIG. 43 is a diagram illustrating a basic screen on which the second distribution information is selected.

FIG. 43 is a diagram illustrating the basic screen K2 on which the second distribution information is selected. In FIG. 43, "bronchial" is selected. In this case, thumbnail images of similar cases corresponding to the bronchial distribution of lesions among the similar cases are displayed in the case display area 710. In addition, all the thumbnail images in the case display area 710 have been enlarged with the second enlargement factor so that the center of the region of interest ROI in each thumbnail image matches the center of a display area 6901 (an example of a display frame).

In S1303, the display control unit 104 extracts similar cases, which are obtained as a result of the similar case search and the number of which is less than or equal to the maximum number of thumbnail images that can be displayed in the case display area 710 among the similar cases corresponding to the distributions of lesions selected as the third distribution information by the user, in order of decreasing similarity, and determines the number of extracted similar cases as the number of similar cases NZ3 to be subjected to enlargement. The display control unit 104 further determines the thumbnail image of the extracted similar case i as a target thumbnail image to be processed. The display control unit 104 repeatedly performs the processing of S5300 and S1503 until the index i has reached the value NZ3. The display control unit 104 increments the index i by 1 each time the processing of S5300 and S1503 is executed. If the index i exceeds the value NZ3 (NO in S1303), the process ends.

In S5300, the display control unit 104 calculates a third enlargement factor for the third distribution information on the similar case i by using the size of a display area determined in advance for each thumbnail image in the case display area 710, the region-of-interest information on the similar case i, and pleural area information 4900.

FIG. 46 is a diagram illustrating the data configuration of similar case data 4000 that additionally includes the pleural area information 4900. If the similar case data 4000 does not have registered therein the pleural area information 4900, the pleural area information 4900 is not obtained. In this case, it may be sufficient that the display control unit 104 sets the third enlargement factor to 1.0, which is equal to the first enlargement factor. The pleural area information 4900 is information indicating the pleural area in a similar case.

In S1503, the display control unit 104 enlarges the thumbnail image of the similar case i with the third enlargement factor ki, and displays the thumbnail image in the case display area 710 so that the center of the region of interest in the thumbnail image matches the center of the display area.

Figure 45:
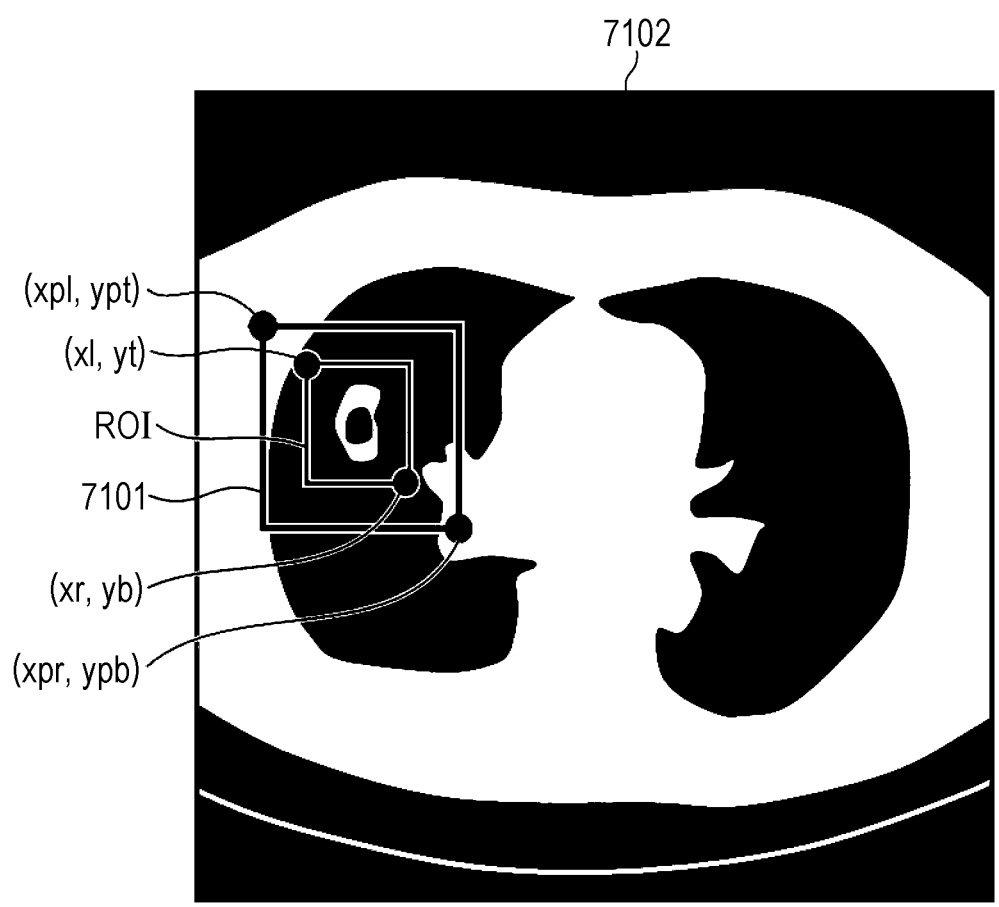
FIG. 45 is a diagram depicting a pleural area.

FIG. 45 is a diagram depicting a pleural area 7101. As illustrated in FIG. 45, the pleural area 7101 includes a pleura and is a rectangular area that is centered on the center of the region of interest ROI and that has a slightly larger size than the region of interest ROI. The pleural area information 4900 includes four values, namely, the coordinates (xpl, ypt) of the upper left corner of the pleural area 7101 and the coordinates (xrp, ypb) of the lower right corner of the pleural area 7101. If the third distribution information is selected, the display control unit 104 calculates the third enlargement factor ki in accordance with the following equation in order to display the pleural area in enlarged form:

$$ki = Sd/Sp,$$

where Sd denotes the area of a display area 7102 and Sp denotes the area of the pleural area 7101.

The user may input the pleural area information 4900 together with region-of-interest information when creating the similar case data 4000. Alternatively, the pleural area information 4900 may be automatically created by automatically extracting the lung area from a slice image and determining the pleural position using an image processing device.

Figure 44:
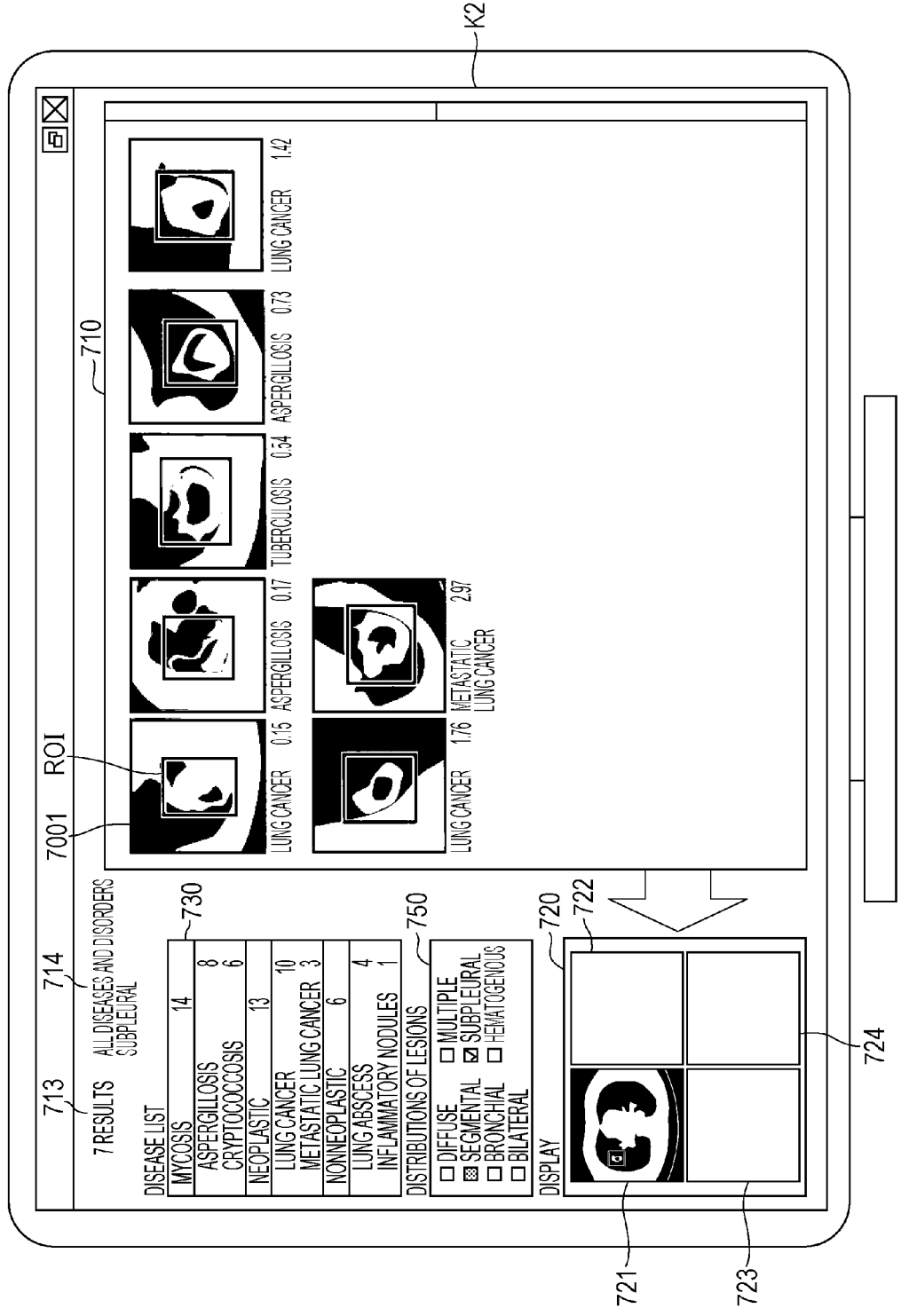
FIG. 44 is a diagram illustrating a basic screen on which the third distribution information is selected.

FIG. 44 is a diagram illustrating the basic screen K2 on which the third distribution information is selected. In FIG. 44, "subpleural" is selected. In this case, thumbnail images of similar cases corresponding to the subpleural distribution of lesions among the similar cases are displayed in the case display area 710. In addition, all the thumbnail images in the case display area 710 have been enlarged with the third enlargement factor so that the center of the region of interest ROI in each thumbnail image matches the center of a display area 7001 (an example of a display frame).

Through the process described above, thumbnail images are displayed in the case display area 710 with an enlargement factor that reflects the content of the diagnosis regarding a distribution of lesions. In addition, the thumbnail images are displayed in the case display area 710 with uniformity in size across the regions of interest in the individual thumbnail images. This may prevent the occurrence of oversight caused by the way in which the region of interest in some similar medical images has been enlarged but is so small, and may improve diagnosis accuracy. In addition, not all the similar cases obtained as a result of the similar case search but similar cases displayed in the case display area 710 are subjected to enlargement, resulting in a significantly reduced load on a system.

If a plurality of disease names are selected in the disease list display area 730 and sub-areas are displayed in the case display area 710, thumbnail images of similar cases displayed in the case display area 710 are enlarged on a per-sub-area basis in accordance with a user operation. In the following, the enlarged display of a thumbnail image of a similar case will be described.

Figure 52:
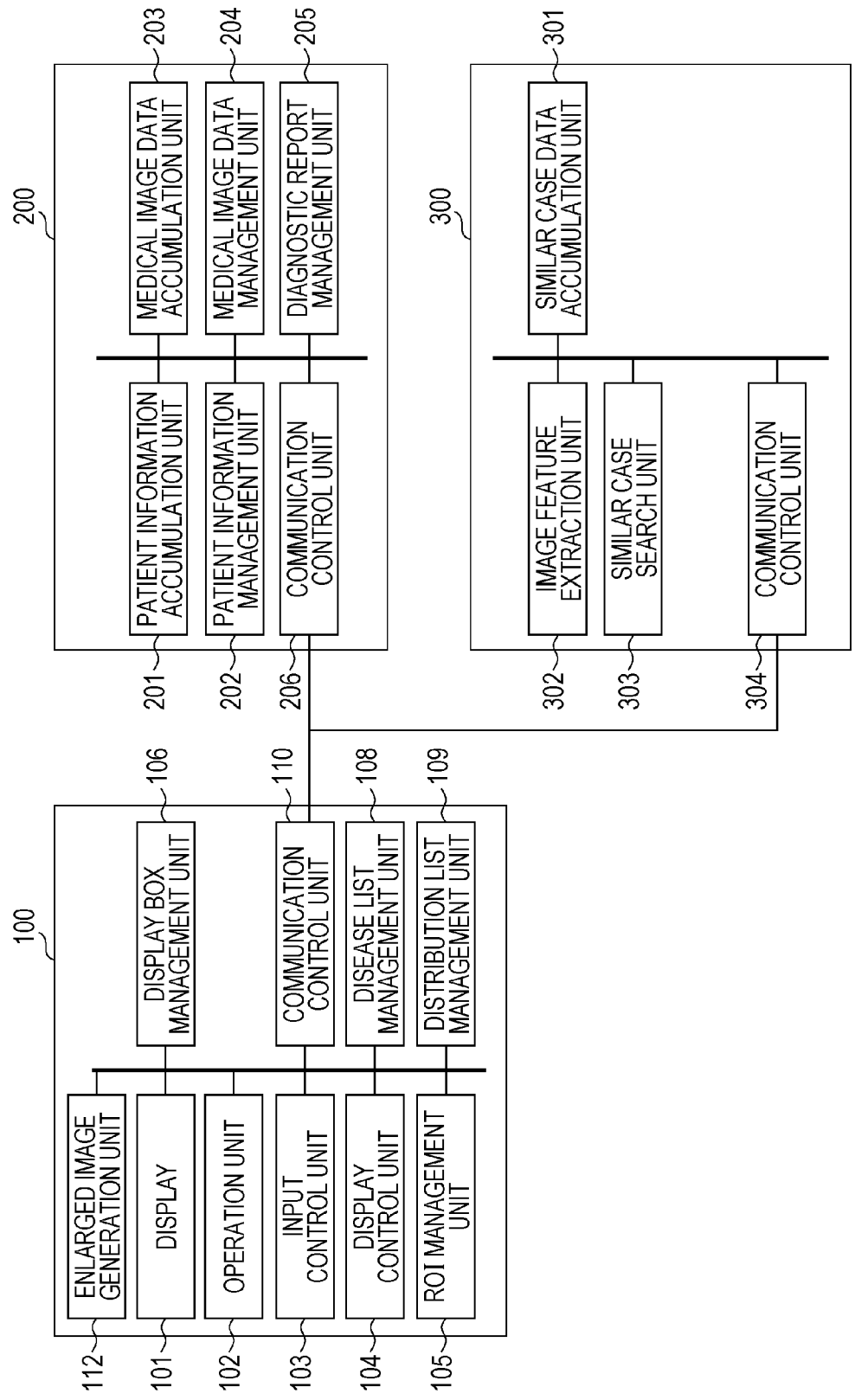
FIG. 52 is a block diagram illustrating the configuration of the information terminal, the medical information management system, and the case search system in a case where the information terminal has an enlarged display function.

FIG. 52 is a block diagram illustrating the configuration of the information terminal 100, the medical information management system 200, and the case search system 300 in a case where the information terminal 100 has an enlarged display function. The configuration illustrated in FIG. 52 is different from that illustrated in FIG. 2 in that the information terminal 100 further includes an enlarged image generation unit 112.

The enlarged image generation unit 112 generates an enlarged image of a thumbnail image of a similar case. The enlarged image generation unit 112 obtains the amount of operation performed on the operation unit 102 by the user from the input control unit 103. The enlarged image generation unit 112 receives, through the communication control unit 110, the similar case data 4000 (including the region-of-interest information 4300 and so forth) with which the similarity to the search query image is associated, which is transmitted from the case search system 300. When a plurality of sub-areas are formed in the case display area 710 in response to the selection of a plurality of disease names in the disease list display area 730, the enlarged image generation unit 112 calculates enlargement factors for the thumbnail images of the similar cases displayed in a sub-area selected by the user, where a different enlargement factor is set for each thumbnail image, to generate a number of enlarged images corresponding to the number of thumbnail images displayed.

Figure 54:
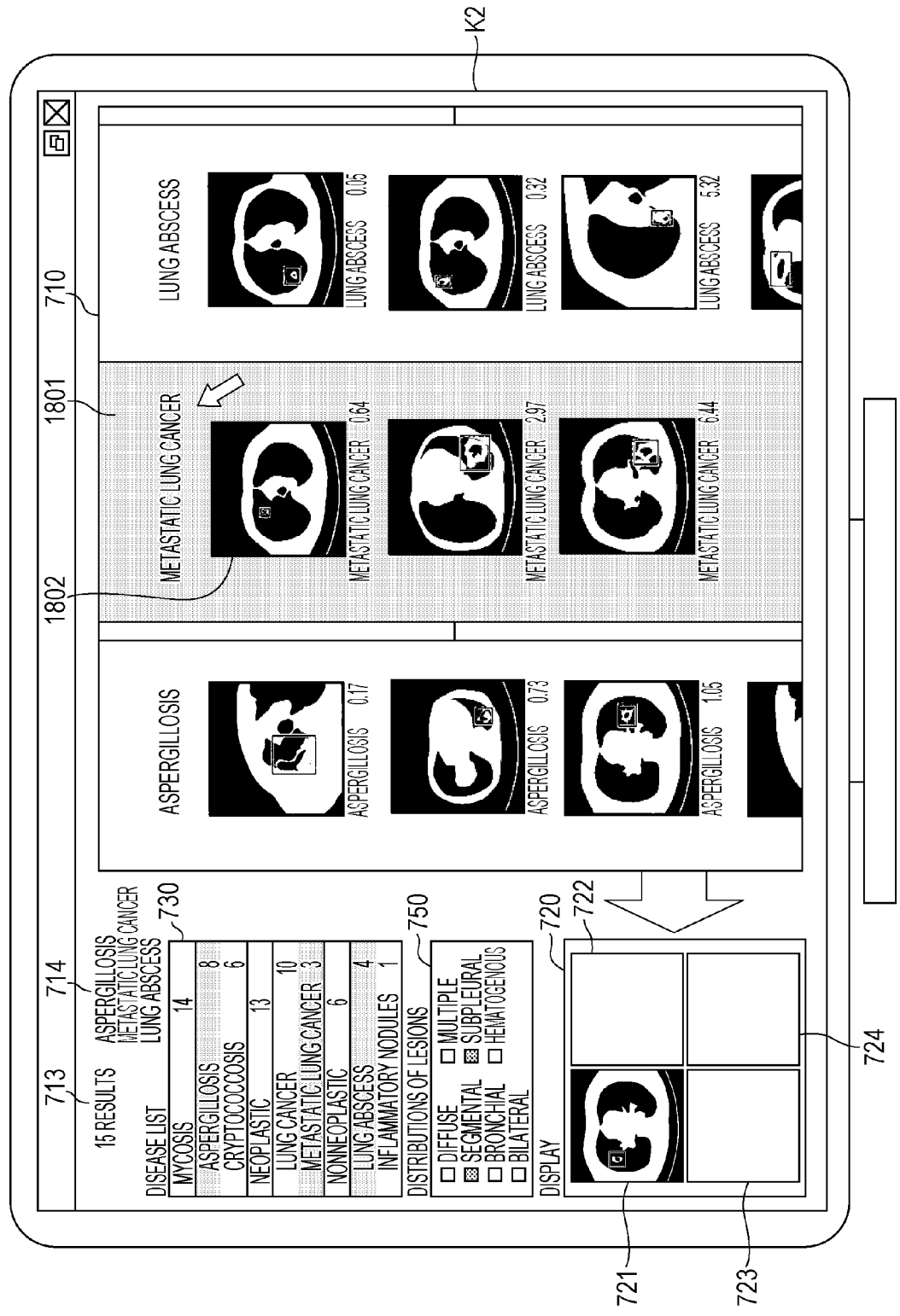
FIG. 54 is a diagram illustrating a basic screen on which one sub-area is selected from among sub-areas formed in the case display area.

FIG. 54 is a diagram illustrating the basic screen K2 on which a sub-area 1801 is selected from among the sub-areas formed in the case display area 710. As illustrated in FIG. 54, thumbnail images are entirely displayed in each sub-area immediately after a plurality of disease names are selected.

The input control unit 103 of the information terminal 100 constantly monitors the input through the operation unit 102 such as the mouse. The input control unit 103 detects that the operation of clicking the mouse has been input by the user and that a sub-area 1801 has been selected from among sub-areas displayed in the case display area 710 in accordance with the operation. Then, the display control unit 104 changes the color of the background of the selected sub-area 1801. Here, it may be sufficient that the input control unit 103 determines that the sub-area 1801 in which the mouse pointer is located when the mouse is clicked among the plurality of sub-areas is the sub-area selected by the user.

In the example illustrated in FIG. 54, the sub-area 1801 in the second column from the left is selected in the case display area 710. Accordingly, the color of the background against which the thumbnail images are displayed in the sub-area 1801 is changed. The user is thus notified that the thumbnail images displayed in the sub-area 1801 are available to be selected.

The color of the background is, for example, a color that is clearly distinguishable from the color of the background of the case display area 710. In the example illustrated in FIG. 54, yellow is used by way of example. The example illustrated in FIG. 54 provides an embodiment in which the color of the background of a sub-area is changed. In an alternative embodiment, the background of a sub-area may be marked with a flashing light, or a sub-area may be made brighter.

As illustrated in FIG. 54, for example, when the user performs an enlargement operation to rotate the mouse wheel while the sub-area 1801 is being selected, the input control unit 103 detects the amount of rotation of the mouse wheel, and notifies the enlarged image generation unit 112 of the detected amount of rotation. The enlarged image generation unit 112 then determines an enlargement factor by using, for example, the detected amount of rotation, and enlarges a thumbnail image displayed in the sub-area 1801 with the determined enlargement factor. The display control unit 104 displays the thumbnail image which has been enlarged by the enlarged image generation unit 112 in the case display area 710. The input control unit 103 may determine the input of the enlargement operation by the user in response to the rotation of the mouse wheel while the mouse pointer is in a display area 1802 (an example of a display frame) of a thumbnail image in the sub-area 1801 available to be selected.

Figure 55:
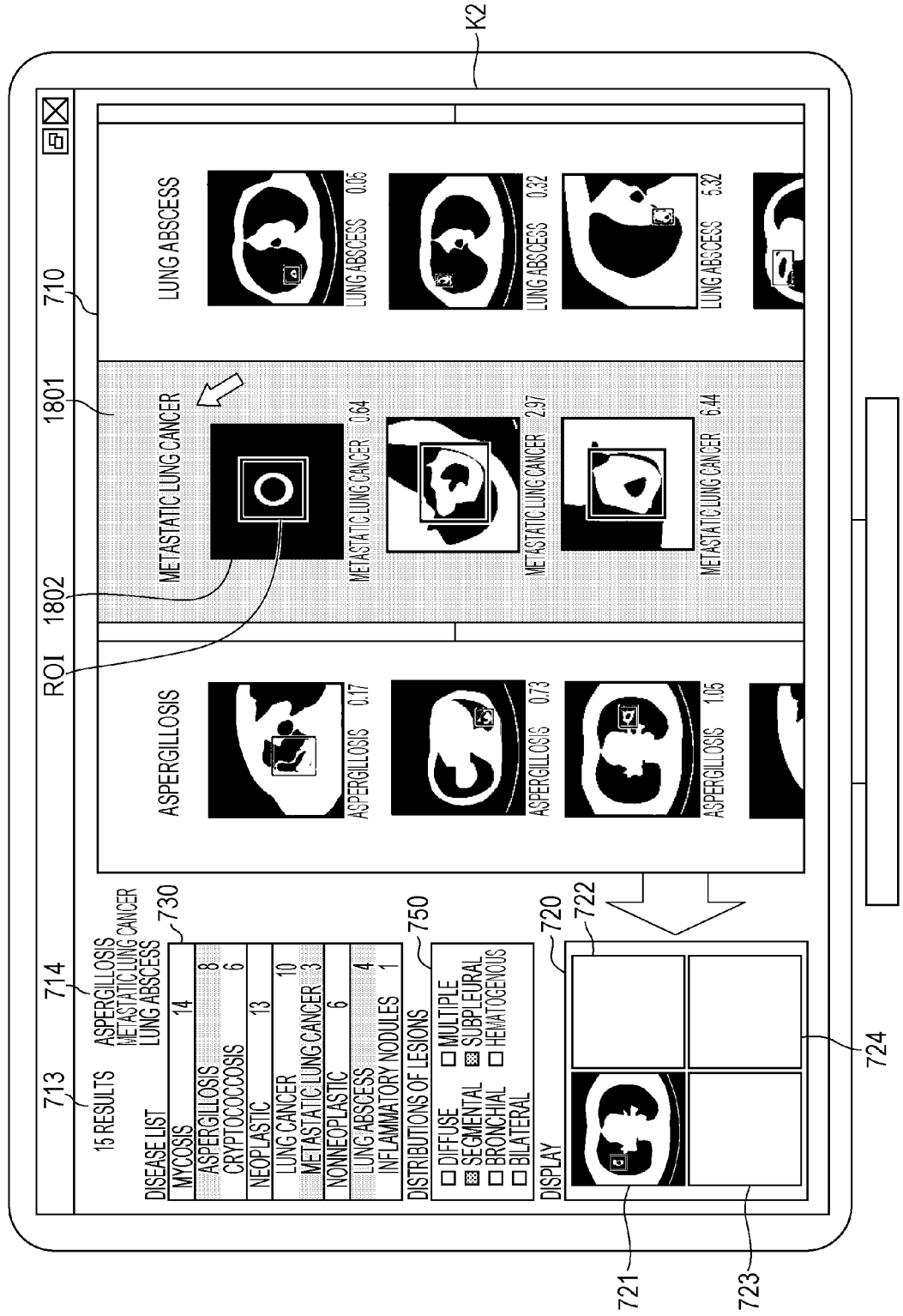
FIG. 55 is a diagram illustrating a basic screen on which thumbnail images in a sub-area are enlarged.

FIG. 55 is a diagram illustrating the basic screen K2 on which thumbnail images in a sub-area are enlarged. As illustrated in FIG. 55, all the thumbnail images displayed in the selected sub-area 1801 are enlarged in one batch. This will eliminate the need for the user to separately input an instruction to enlarge each of the thumbnail images displayed in the sub-area 1801. Thus, operational efficiency may be improved.

When enlarging a thumbnail image being displayed, as illustrated in FIG. 55, the enlarged image generation unit 112 generates an enlarged image so that the coordinates of the center of the region of interest ROI in the thumbnail image match the coordinates of the center of the display area 1802. When enlarging the thumbnail image, furthermore, as illustrated in FIG. 55, the display control unit 104 maintains the size of the display area 1802 as is without increasing the size of the display area 1802.

The enlarged image generation unit 112 may set different enlargement factors for the individual thumbnail images so that the regions of interest ROI in the thumbnail images have the same size. Accordingly, as illustrated in FIG. 55, the thumbnail images being displayed in the sub-area 1801 are enlarged so that the regions of interest ROI therein have the same size. This can prevent the user from overlooking a thumbnail image in which the region of interest ROI has not been sufficiently enlarged compared to the other thumbnail images.

Figure 56:
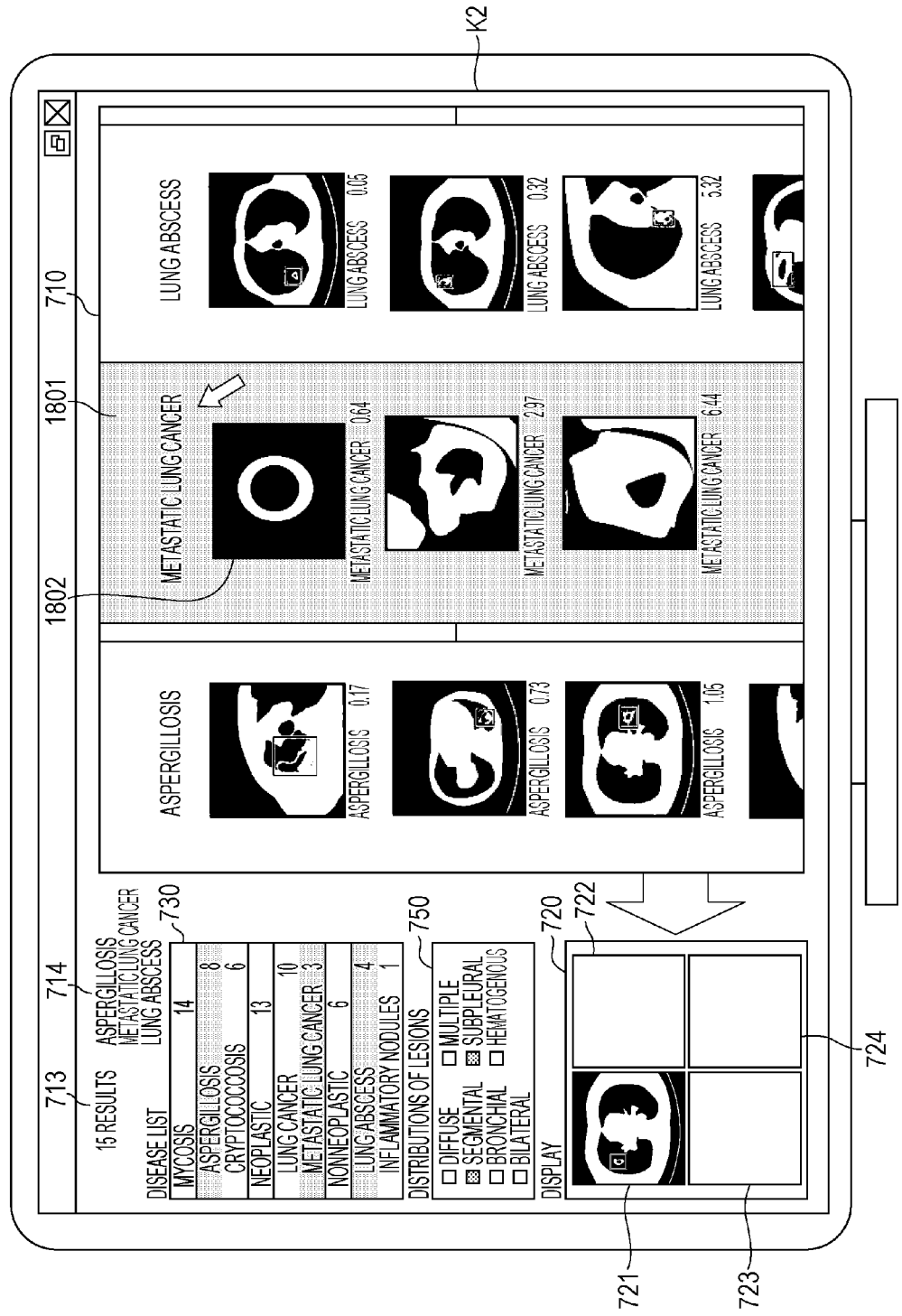
FIG. 56 is a diagram illustrating an example display of the basic screen that is different from that illustrated in FIG. 55 when some of the thumbnail images displayed in the case display area are enlarged.

FIG. 56 is a diagram illustrating an example display of the basic screen K2 that is different from that illustrated in FIG. 55 when some of the thumbnail images displayed in the case display area 710 are enlarged. In FIG. 56, the enlarged image generation unit 112 enlarges a thumbnail image until the size of the region of interest ROI become substantially the same as the size of the display area 1802.

In the way described above, in a case where a plurality of disease names are selected in the disease list display area 730 and the case display area 710 is divided into sub-areas for display, a user who makes image-based diagnosis is able to display a set of thumbnail images corresponding to a disease name on which they focus their attention, in enlarged form in one batch by performing a single operation. Accordingly, the user is able to compare a plurality of similar cases in detail by issuing an enlargement instruction once. This significantly reduces the number of operations, resulting in a reduction in the load on the user.

In the foregoing description, the user performs an enlargement operation by rotating the mouse wheel. However, this embodiment is not limited to this. The user may perform an enlargement operation by, for example, placing the mouse pointer on one of the thumbnail images displayed in the case display area 710 and pressing, for example, the up arrow key or down arrow key on the keyboard while pressing the mouse button. In this case, the input control unit 103 counts the length of time during which the up arrow key or down arrow key is pressed, and notifies the enlarged image generation unit 112 of the count value. The enlarged image generation unit 112 may then determine an enlargement factor so that as the count value of which the enlarged image generation unit 112 is notified increases, the enlargement factor increases.

Next, a thumbnail image enlargement process will be specifically described.

Figure 57:
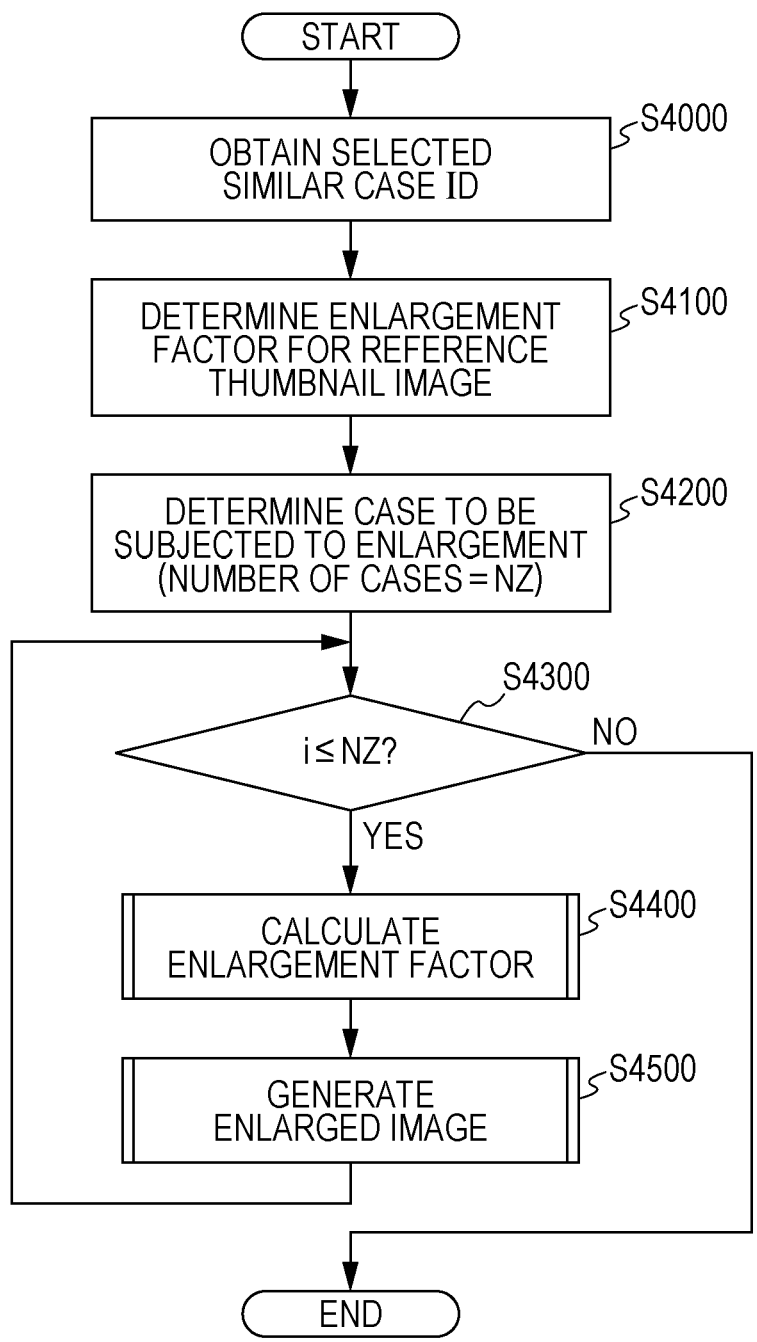
FIG. 57 is a flowchart illustrating a process for enlarging thumbnail images displayed in the case display area.

FIG. 57 is a flowchart illustrating a process for enlarging thumbnail images displayed in the case display area 710. It is assumed that one of the sub-areas in the case display area 710 is available to be selected before the start of the flowchart.

In S4000, the enlarged image generation unit 112 obtains the similar case ID 4100 of a thumbnail image selected by the user within the sub-area 1801 available to be selected (in the example illustrated in FIG. 54, the sub-area 1801 in the second column from the left) when the user inputs an enlargement operation, from the similar case data 4000 illustrated in FIG. 46. The user selects a thumbnail image by placing the mouse pointer on one of the thumbnail images displayed in the sub-area 1801. In the following description, the thumbnail image selected by the user when the user performs an enlargement operation is referred to as a "reference thumbnail image". The enlarged image generation unit 112 determines enlargement factors for the other thumbnail images displayed in the case display area 710 in association with the enlargement operation performed on the reference thumbnail image by the user.

In S4100, the enlarged image generation unit 112 obtains the amount of enlargement operation to be performed on the reference thumbnail image, which is input to the operation unit 102 by the user, from the input control unit 103. Then, the enlarged image generation unit 112 determines an enlargement factor for the reference thumbnail image by using the obtained the amount of operation.

Specifically, the input control unit 103 detects the amount of rotation of the mouse wheel when the mouse wheel is rotated while the mouse pointer is on a thumbnail image, and notifies the enlarged image generation unit 112 of the detected amount of rotation. The enlarged image generation unit 112 multiplies the amount of rotation by a predetermined coefficient to calculate an enlargement factor for the reference thumbnail image.

As described above, the user may perform an enlargement operation by using either the up arrow key or the down arrow key on the keyboard. In this case, the input control unit 103 counts the length of time during which the up arrow key or the down arrow key is pressed when the mouse button is pressed while the mouse pointer is on a thumbnail image, and notifies the enlarged image generation unit 112 of the count value. The enlarged image generation unit 112 may multiply the count value by a predetermined coefficient to calculate an enlargement factor for the reference thumbnail image.

In S4200, the enlarged image generation unit 112 determines a similar case to be subjected to enlargement among the plurality of similar cases obtained from the case search system 300. In this case, a similar case that is being displayed in the sub-area 1801 that includes the reference thumbnail image selected in S4000 is selected as a similar case to be subjected to enlargement. Here, the number of similar cases to be subjected to enlargement is represented by NZ. The term "similar case that is being displayed" does not include a similar case that is not currently visible in the sub-area 1801. For example, in FIG. 54, it is assumed that the sub-area 1801 for aspergillosis in the first column from the left is selected and an enlargement operation is input. It is also assumed that the sub-area 1801 for aspergillosis includes three similar cases, the entirety of which is being displayed, and one similar case, part of which is being displayed, that is, four similar cases in total, and also includes similar cases that are not currently visible. In this case, the four similar cases that are being displayed are targets to be subjected to enlargement, whereas the other similar cases that are not currently visible are not targets to be subjected to enlargement.

In S4300, the enlarged image generation unit 112 determines the thumbnail image of the similar case i (where i is an index identifying a target similar case to be processed, and is an integer greater than or equal to 1) as a target thumbnail image to be processed. The enlarged image generation unit 112 repeatedly performs the processing of S4400 and S4500 until the index i has reached the value NZ (YES in S4300). The enlarged image generation unit 112 increments the index i by 1 each time the processing of S4400 and S4500 is executed. If the index i exceeds the value NZ (NO in S4300), the process illustrated in FIG. 57 ends.

In S4400, the enlarged image generation unit 112 calculates an enlargement factor for the thumbnail image of the similar case i to be subjected to enlargement. The enlarged image generation unit 112 calculates the enlargement factor for the similar case i to be subjected to enlargement, on the basis of the enlargement factor for the reference thumbnail image determined in S4100, the region-of-interest information 4300 (FIG. 46) on the similar case corresponding to the reference thumbnail image, and the region-of-interest information 4300 (FIG. 46) on the similar case i to be subjected to enlargement.

Figure 58:
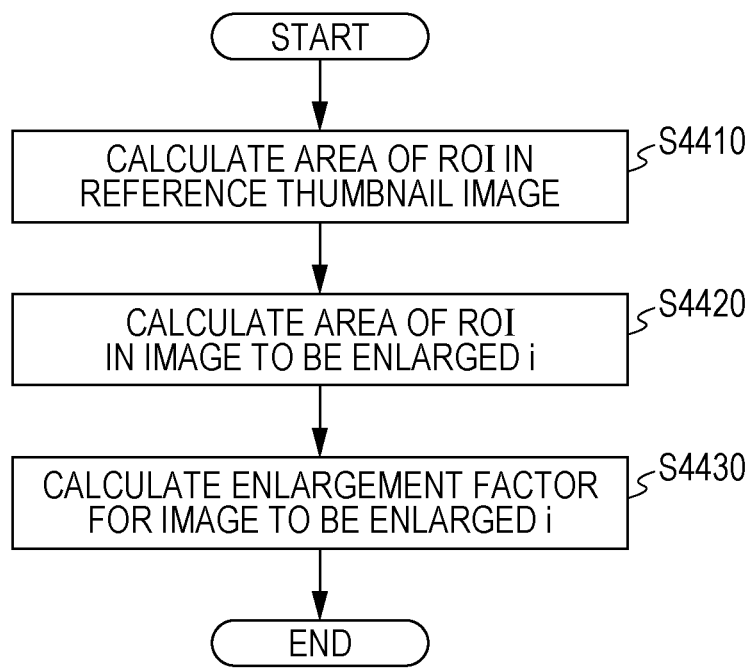
FIG. 58 is a flowchart illustrating a process in a subroutine of S4400 in FIG. 57.

FIG. 58 is a flowchart illustrating a process in a subroutine of S4400 in FIG. 57.

In S4410, the enlarged image generation unit 112 calculates the area of the region of interest in the reference thumbnail image by using the region-of-interest information 4300 on the similar case corresponding to the reference thumbnail image. Given that the area of the region of interest in the reference thumbnail image is represented by Sr, the coordinates of the upper left corner of the region of interest are represented by (xl, yt), and the coordinates of the lower right corner of the region of interest are represented by (xr, yb), the area Sr of the region of interest can be calculated in accordance with the following equation:

$$Sr=|xl-xr|\times|yt-yb|.$$

In S4420, the enlarged image generation unit 112 calculates the area of the region of interest in the thumbnail image of the similar case i to be subjected to enlargement by using the region-of-interest information 4300 on the similar case i to be subjected to enlargement. Given that the area of the region of interest in the thumbnail image of the similar case i to be subjected to enlargement is represented by Si, the coordinates of the upper left corner of the region of interest are represented by (xli, yti), and the coordinates of the lower right corner of the region of interest are represented by (xri, ybi), the area Si of the region of interest can be calculated in accordance with the following equation:

$$Si=|xli-xri|\times|yti-ybi|.$$

In S4430, the enlarged image generation unit 112 calculates an enlargement factor for the similar case i to be subjected to enlargement by using the area Sr of the region of interest in the reference thumbnail image, which is calculated in S4410, the area Si of the region of interest in the thumbnail image of the similar case i to be subjected to enlargement, which is calculated in S4420, and the enlargement factor for the reference thumbnail image, which is determined in S4100. Given that the enlargement factor for the reference thumbnail image is represented by kr, the enlargement factor ki for the similar case i to be subjected to enlargement can be calculated in accordance with the following equation:

$$ki=kr(Sr/Si).$$

Figure 59:
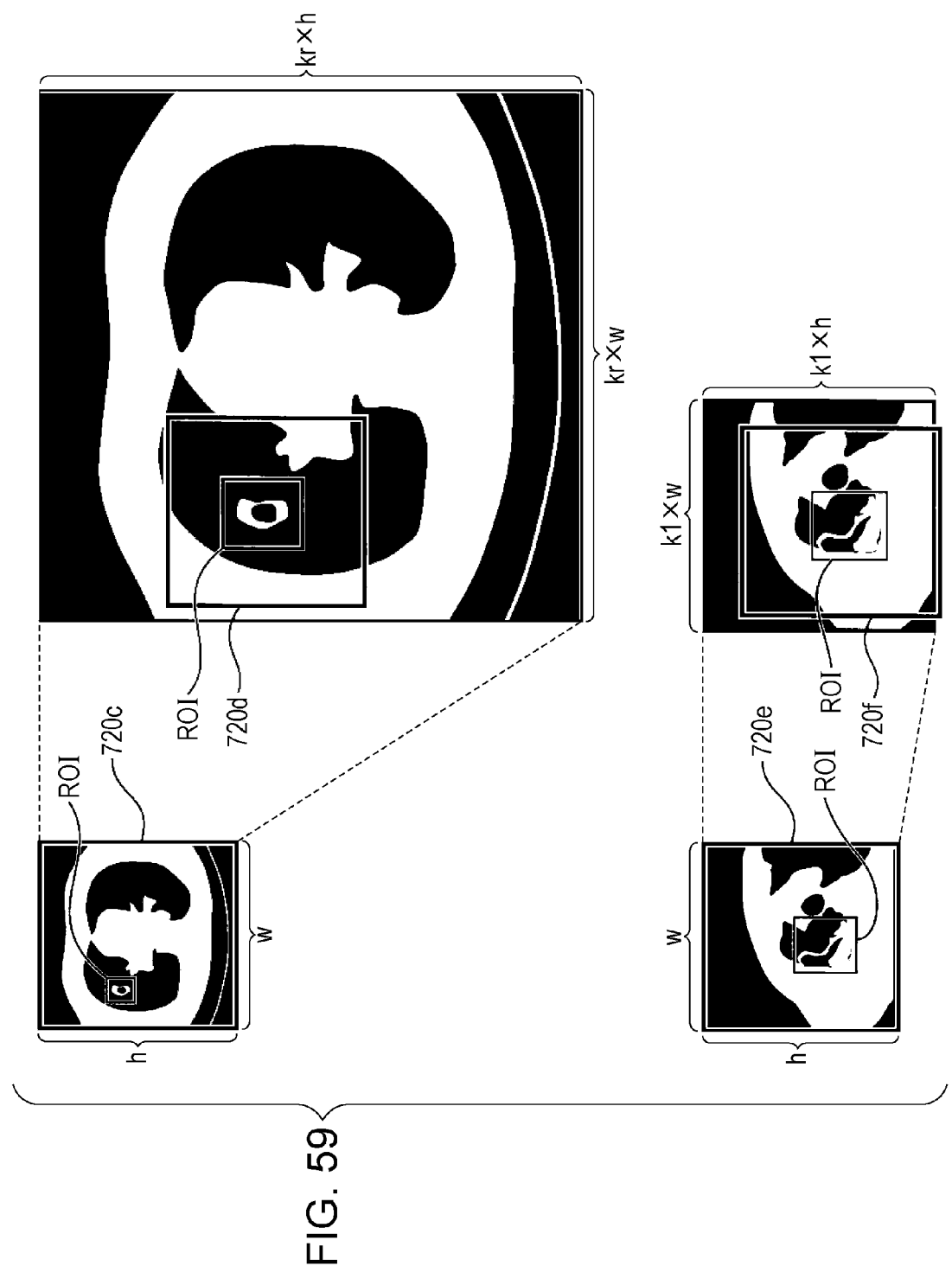
FIG. 59 is a schematic diagram illustrating reference thumbnail images obtained before and after an enlargement process is performed and thumbnail images to be enlarged which are obtained before and after an enlargement process is performed.

FIG. 59 is a schematic diagram illustrating reference thumbnail images obtained before and after an enlargement process is performed and thumbnail images to be enlarged which are obtained before and after an enlargement process is performed. The reference thumbnail image obtained before the enlargement process is performed is illustrated in the upper left part of FIG. 59. The reference thumbnail image obtained after the enlargement process is performed is illustrated in the upper right part of FIG. 59. The thumbnail image to be enlarged which is obtained before the enlargement process is performed is illustrated in the lower left part of FIG. 59. The thumbnail image to be enlarged which is obtained after the enlargement process is performed is illustrated in the lower right part of FIG. 59.

As a result of enlarging the reference thumbnail image illustrated in the upper left part of FIG. 59 with the enlargement factor kr, the thumbnail image illustrated in the upper right part of FIG. 59 is obtained. The enlarged image generation unit 112 determines a display area 720d so that, in the upper right part of FIG. 59, the coordinates of the center of the region of interest ROI match the coordinates of the center of the display area 720d. The enlarged image generation unit 112 maintains the size of the display area 720d to be equal to the size of a display area 720c in the image obtained before the enlargement process is performed.

As a result of enlarging the thumbnail image to be enlarged illustrated in the lower left part of FIG. 59 with the enlargement factor ki, the thumbnail image illustrated in the lower right part of FIG. 59 is obtained. The enlarged image generation unit 112 sets a display area 720f so that, in the lower right part of FIG. 59, the coordinates of the center of the region of interest ROI match the coordinates of the center of the display area 720f. The enlarged image generation unit 112 maintains the size of the display area 720f to be equal to the size of a display area 720e in the image obtained before the enlargement process is performed.

In FIG. 59, the enlargement factor ki is determined so that the area of a region of interest ROI obtained as a result of enlarging the region of interest ROI in the reference thumbnail image with the enlargement factor kr is the same as the area of a region of interest ROI obtained as a result of enlarging the region of interest ROI in the thumbnail image of the similar case i to be subjected to enlargement with the enlargement factor ki. Accordingly, as illustrated in FIG. 59, the size of the region of interest ROI in the reference thumbnail image, which is obtained after enlargement, is equal to the size of the region of interest ROI in the thumbnail image of the similar case i to be subjected to enlargement, which is obtained after enlargement.

Referring back to FIG. 57, in S4500, the enlarged image generation unit 112 enlarges the similar case i to be subjected to enlargement, by using the enlargement factor ki calculated in S4400 and the region-of-interest information 4300 and the thumbnail image data 4500 registered in the similar case data 4000 (FIG. 46) to generate an enlarged image. The display control unit 104 displays the enlarged image generated by the enlarged image generation unit 112.

Figure 60:
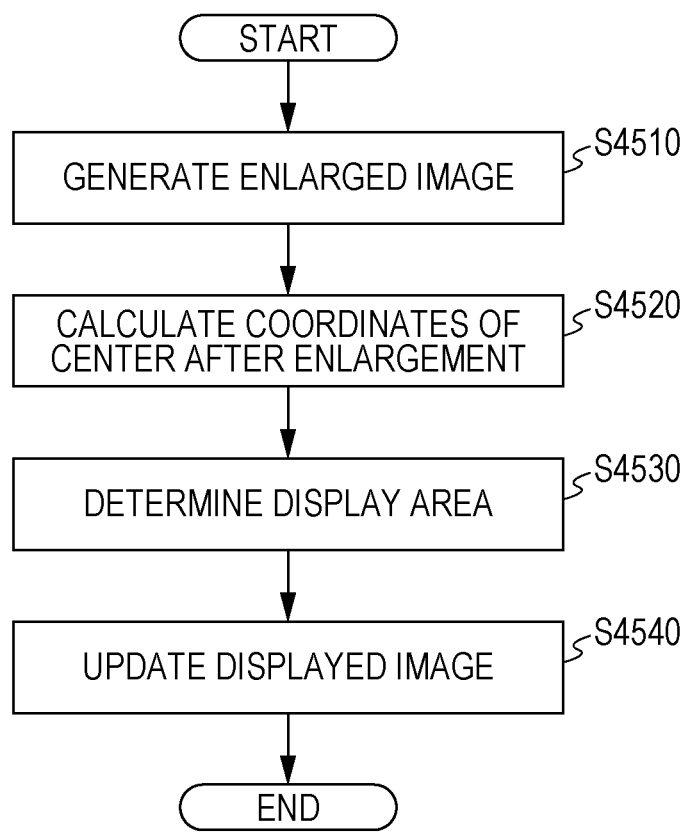
FIG. 60 is a flowchart illustrating a process in a subroutine of S4500 in FIG. 57.
Figure 61:
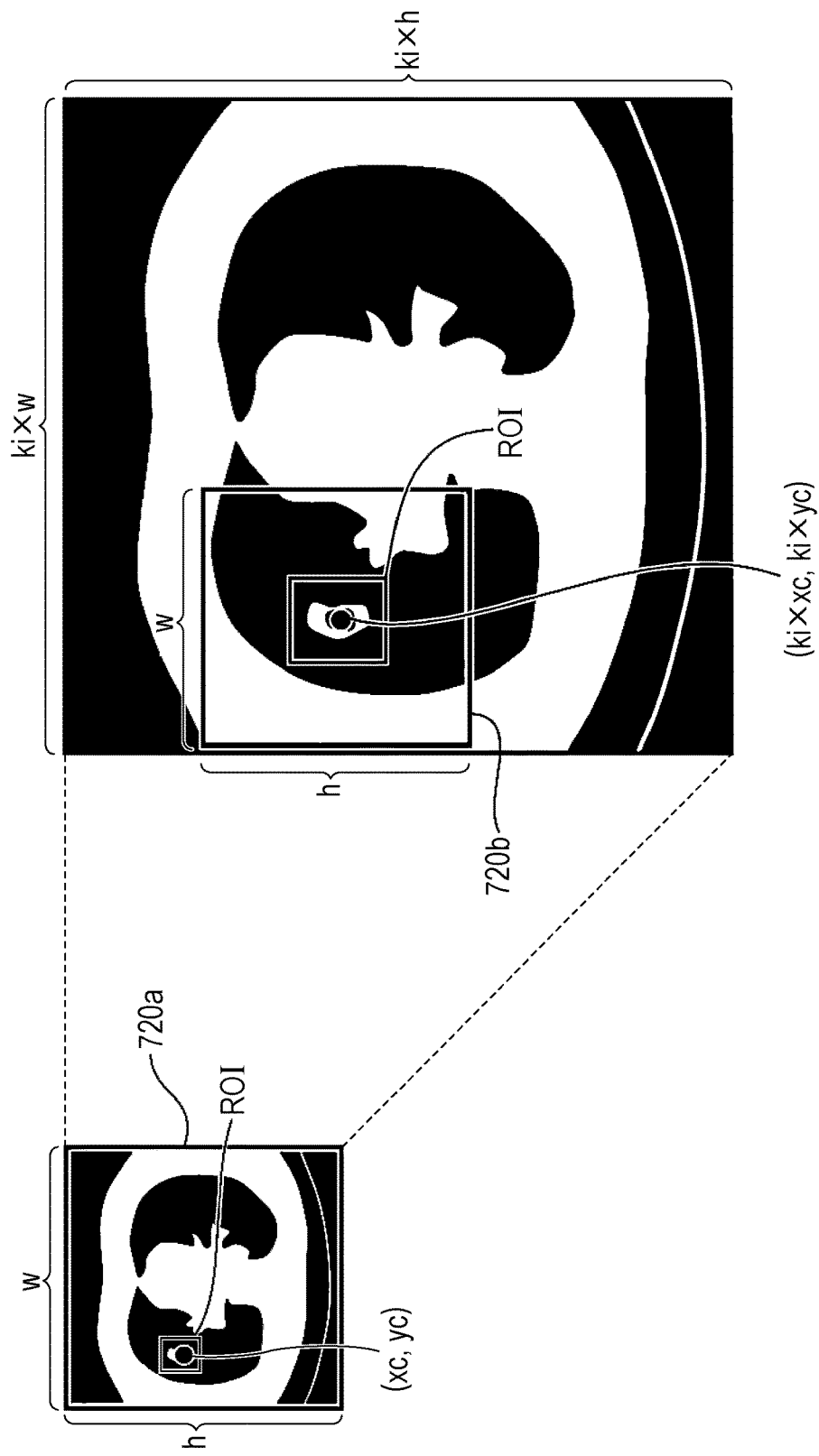
FIG. 61 is a schematic diagram illustrating the relationship between an enlargement factor and a display area.

FIG. 60 is a flowchart illustrating a process in a subroutine of S4500 in FIG. 57. FIG. 61 is a schematic diagram illustrating the relationship between an enlargement factor and a display area. The process for generating an enlarged image so that the coordinates of the center of the region of interest in the enlarged image match the coordinates of the center of the display area will be described in detail with reference to FIG. 60 and FIG. 61.

In S4510, the enlarged image generation unit 112 generates an enlarged image by using the enlargement factor ki calculated in S4400 and the thumbnail image data 4500 registered in the similar case data 4000 (FIG. 46). An enlarged image illustrated in the right part of FIG. 61 is generated from a thumbnail image illustrated in the left part of FIG. 61 using the enlargement factor ki.

In S4520, the enlarged image generation unit 112 calculates the coordinates of the center of the region of interest in the enlarged image by using the region-of-interest information 4300 registered in the similar case data 4000 (FIG. 46) and the enlargement factor calculated in S4400. Given that the coordinates of the center of the region of interest before enlargement are represented by (xc, yc), as illustrated in FIG. 61, the coordinates (ki×xc, ki×yc), which are obtained by multiplying the coordinates of the center of the region of interest before enlargement by the enlargement factor, are the coordinates of the center of the region of interest after enlargement.

In S4530, the enlarged image generation unit 112 determines a display area of an enlarged version of the thumbnail image of the similar case i by using the coordinates (ki×xc, ki×yc) of the center of the region of interest after enlargement, which are calculated in S4520, and the predetermined size of the display area. As illustrated in the left part of FIG. 61, a display area 720a is set to have a width dimension w and a height dimension h. In this case, a rectangular area having a width dimension w and a height dimension h illustrated in the right part of FIG. 61 is a display area 720b. The coordinates of the upper left corner of the display area 720b are given by (ki×xc−w/2, ki×yc−h/2), and the coordinates of the lower right corner of the display area 720b are given by (ki×xc+w/2, ki×yc+h/2).

In S4540, the display control unit 104 displays an image corresponding to the display area 720b calculated in S4530 within the enlarged image generated by the enlarged image generation unit 112 in S4510, in the display area of the similar case i in the case display area 710. Through the process illustrated in FIG. 60, an enlarged image of the similar case i is generated so that the coordinates of the center of the region of interest in the enlarged image match the coordinates of the center of the display area.

Through the process described above, when the user designates an enlargement factor for the reference thumbnail image, the other thumbnail images that are being displayed in the sub-area 1801 that includes the reference thumbnail image are enlarged in one batch in the case display area 710. This enables the user to enlarge all the thumbnail images that are being displayed in the sub-area 1801 by using a single enlargement operation. This results in a reduction in the operation load on the user. In addition, thumbnail images are displayed in the sub-area 1801 with uniformity in size across the regions of interest in the thumbnail images. This may prevent the occurrence of oversight from a set of candidates for image interpretation, because the region of interest in a certain thumbnail image has been enlarged but is still so small, compared to the other thumbnail images, improving diagnosis accuracy. In addition, not all the similar cases obtained as a result of the similar case search but similar cases that are being displayed in the sub-area 1801 are subjected to enlargement. This results in a significantly reduced processing load on a system.

In the first embodiment, the display 101b is landscape-oriented. Alternatively, the display 101b may be portrait-oriented.

Second Embodiment

Next, a second embodiment of the present disclosure will be described with reference to the drawings. In the drawings, the same or similar components are represented by the same numerals.

In the first embodiment, when one or more disease names are selected, the case display area 710 is divided into one or more vertically elongated sub-areas, each for a disease name, and similar cases are displayed in each sub-area so as to be aligned in a column. In the first embodiment, furthermore, a display style of a typical search screen on the Internet or the like is used in which similar cases having high similarity to the search query image are collected in an upper portion of the case display area 710 in such a manner that search results are displayed, from left to right, in order of decreasing relevance.

It is also conceivable that, after similar cases are refined by selecting one or more disease names, if the similar case having the highest similarity to each disease is displayed closest to the search query image displayed in the layout area 720, a user will be able to efficiently compare the search query image with the similar case. In the second embodiment, the display style described above is used.

In the first embodiment, furthermore, the display 101b is in landscape orientation. In the second embodiment, the display 101b is in portrait orientation. In the second embodiment, the display 101a may be in either landscape or portrait orientation.

The difference between the first embodiment and the second embodiment is a portion related to the display control of the case display area 710, and the following description will focus on this portion while the other portions are not described herein.

Figure 62:
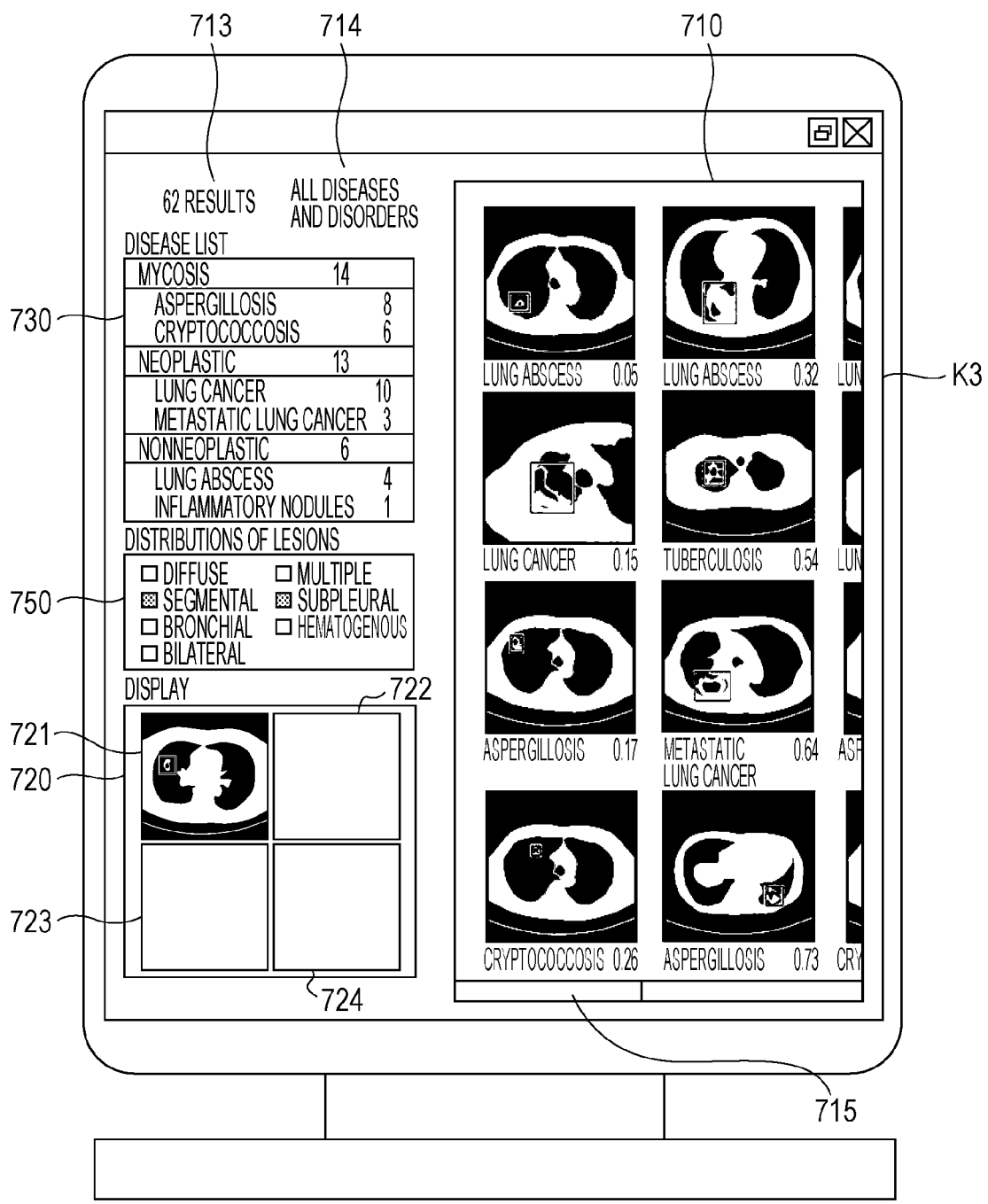
FIG. 62 is a diagram illustrating an example of a basic screen displayed on a display immediately after the similar case search application is started on the information terminal.

FIG. 62 is a diagram illustrating an example of a basic screen K3 displayed on the display 101b immediately after the similar case search application is started on the information terminal 100. As in FIG. 6, the basic screen K3 illustrated in FIG. 62 has the case display area 710, the layout area 720, the disease list display area 730, and the distribution list display area 750.

If the number of similar cases is very large, it will be difficult to display all the similar cases in the case display area 710 at the same time. Accordingly, the case display area 710 has, in a lower portion thereof, for example, a horizontal scrollbar 715.

The display control unit 104 provides horizontal scrolling through the thumbnail images displayed in the case display area 710 in accordance with the amount of movement of the scrollbar 715. This allows currently invisible similar cases to be displayed in the case display area 710 to enables the user to observe the similar cases.

Figure 63:
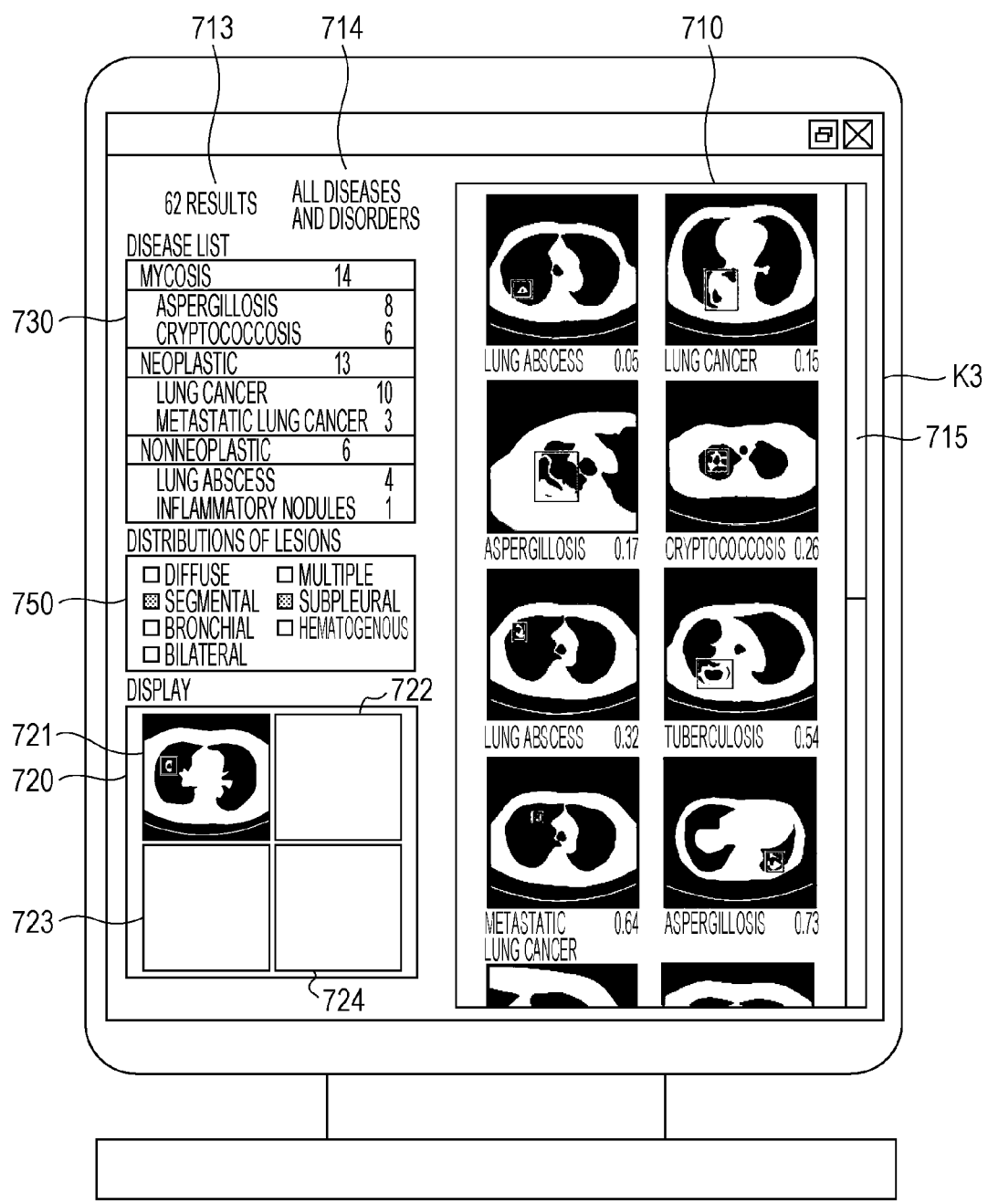
FIG. 63 is a diagram illustrating a basic screen on which the case display area has a vertical scrollbar.

As illustrated in FIG. 63, the scrollbar 715 may be a vertical scrollbar. FIG. 63 is a diagram illustrating the basic screen K3 on which the case display area 710 has a vertical scrollbar 715. In this case, the display control unit 104 may be configured to provide vertical scrolling through the thumbnail images displayed in the case display area 710 in accordance with the amount of movement of the scrollbar 715. Alternatively, the display control unit 104 may be configured to, in response to pressing any arrow key on the keyboard while the mouse pointer is in the case display area 710, provide scrolling through the thumbnail images displayed in the case display area 710, over a period during which the key is pressed, in the direction corresponding to the pressed key.

The thumbnail images may be displayed in the case display area 710 in such a manner that, for example, as illustrated in FIG. 62, the thumbnail image with the shortest distance from the search query image is displayed at the left end of the top row and the distance sequentially increases from top to bottom, where, once the bottom end of the same column is reached, the next, large-distance thumbnail image is displayed at the top end of the second column from the left. That is, the following display technique may be used: The thumbnail images are displayed in the case display area 710, top to bottom from top left, in order of increasing distance.

Other display technique may be used in this embodiment. For example, as illustrated in FIG. 63, a display technique may be used in which thumbnail images are displayed in such a manner that the thumbnail image with the shortest distance from the search query image is displayed at the left end of the top row and the distance sequentially increases from left to right, where, once the right end of the same row is reached, the next, large-distance thumbnail image is displayed at the left end of the second row from the top. That is, the following display technique may be used: The thumbnail images are displayed in the case display area 710, from left to right, top to bottom in order of increasing distance. Alternatively, the plurality of display techniques described above may be switched between by the user.

Next, a screen transition responsive to the selection of a plurality of disease names in the disease list display area 730 will be described. When a plurality of disease names are selected in the disease list display area 730, as in the first embodiment, the case display area 710 is divided into sub-areas in accordance with the number of selected disease names, and associated similar cases are displayed in each of the sub-areas.

Figure 64:
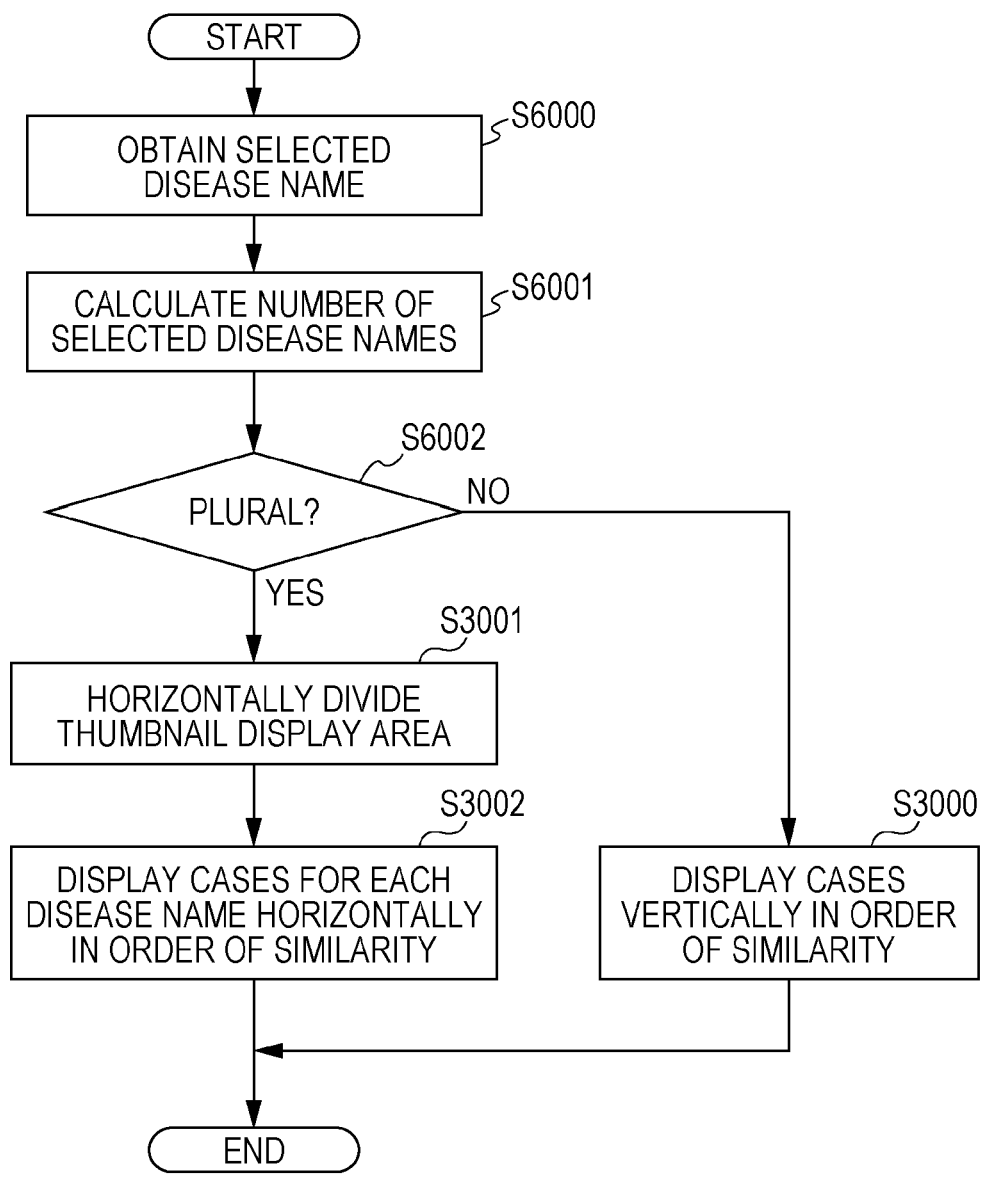
FIG. 64 is a flowchart illustrating an example of a display process performed when a disease name is selected in the disease list display area.

FIG. 64 is a flowchart illustrating an example of a display process performed when a disease name is selected in the disease list display area 730. A display process performed for the case display area 710 when a disease name displayed in the disease list display area 730 is selected will be described in detail with reference to the flowchart illustrated in FIG. 64.

The flowchart illustrated in FIG. 64 includes the processing of S3000, S3001, and S3002 in place of the processing of S6003, S6004, and S6005 in the flowchart illustrated in FIG. 48, respectively.

The processing of S3000 is a display process performed for the case display area 710 when one disease name is selected in the disease list display area 730. In this case, as illustrated in FIG. 65, thumbnail images of similar cases corresponding to the disease name selected in S6000 are displayed in the case display area 710 so as to be arranged vertically in order of increasing distance.

Figure 65:
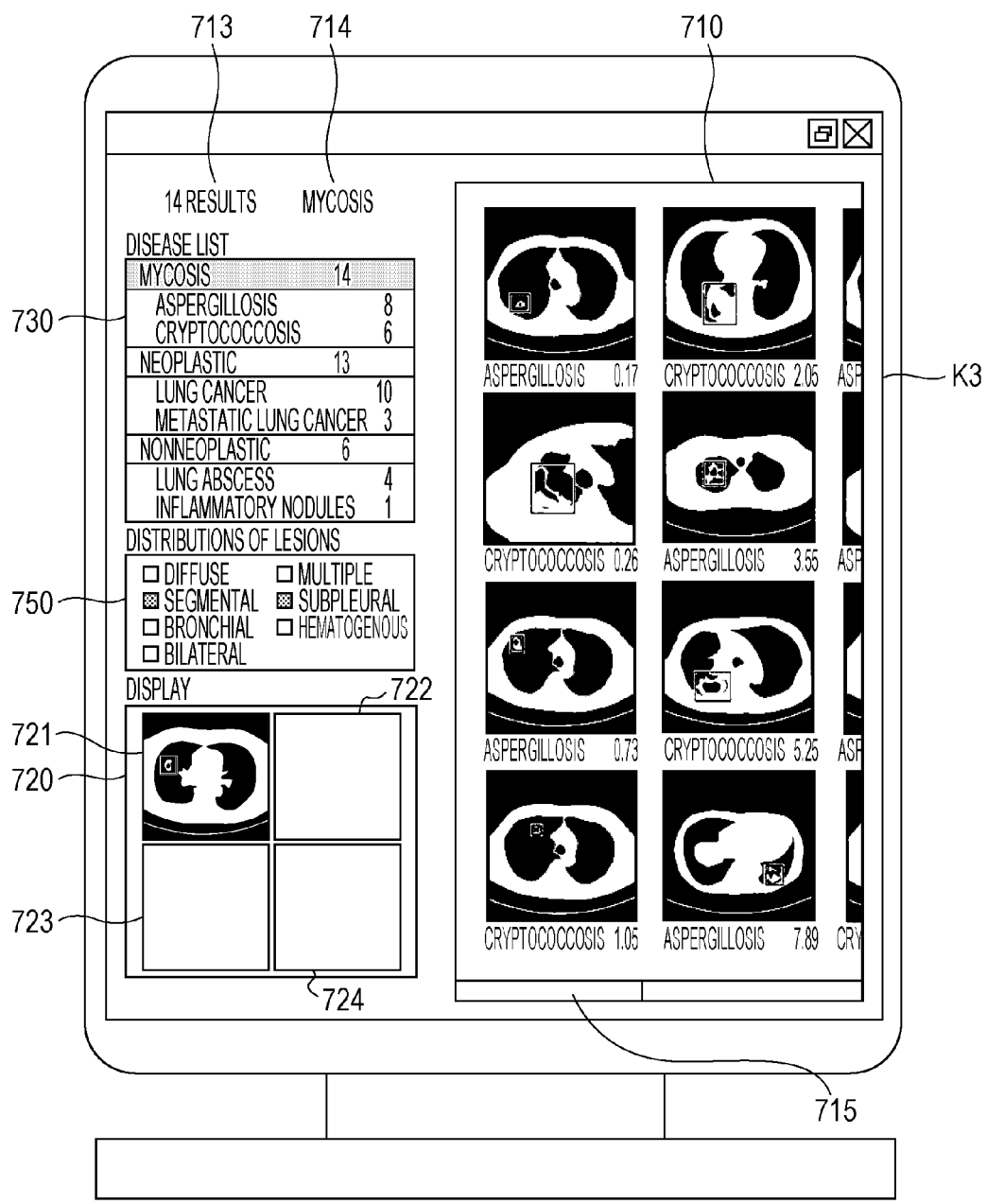
FIG. 65 is a diagram illustrating a first example of a basic screen on which one disease name is selected.

FIG. 65 is a diagram illustrating a first example of the basic screen K3 on which one disease name is selected. In the example illustrated in FIG. 65, thumbnail images of similar cases are displayed in such a manner that the similar case with the shortest distance from (or the highest similarity to) the search query image is displayed at the top end of the first column from the left and similar cases are displayed so as to be arranged from top to bottom in order of increasing distance (or in order of decreasing similarity), where, once the bottom end of the first column is reached, the next, large-distance similar case is displayed at the top end of the second column from the left.

Accordingly, similar cases with high similarity are collected in a left portion of the case display area 710, and are displayed in a location as close to the search query image displayed in the layout area 720 as possible. This helps the user efficiently compare the search query image with the similar cases, which may contributes to an improvement in medical treatment accuracy.

Figure 66:
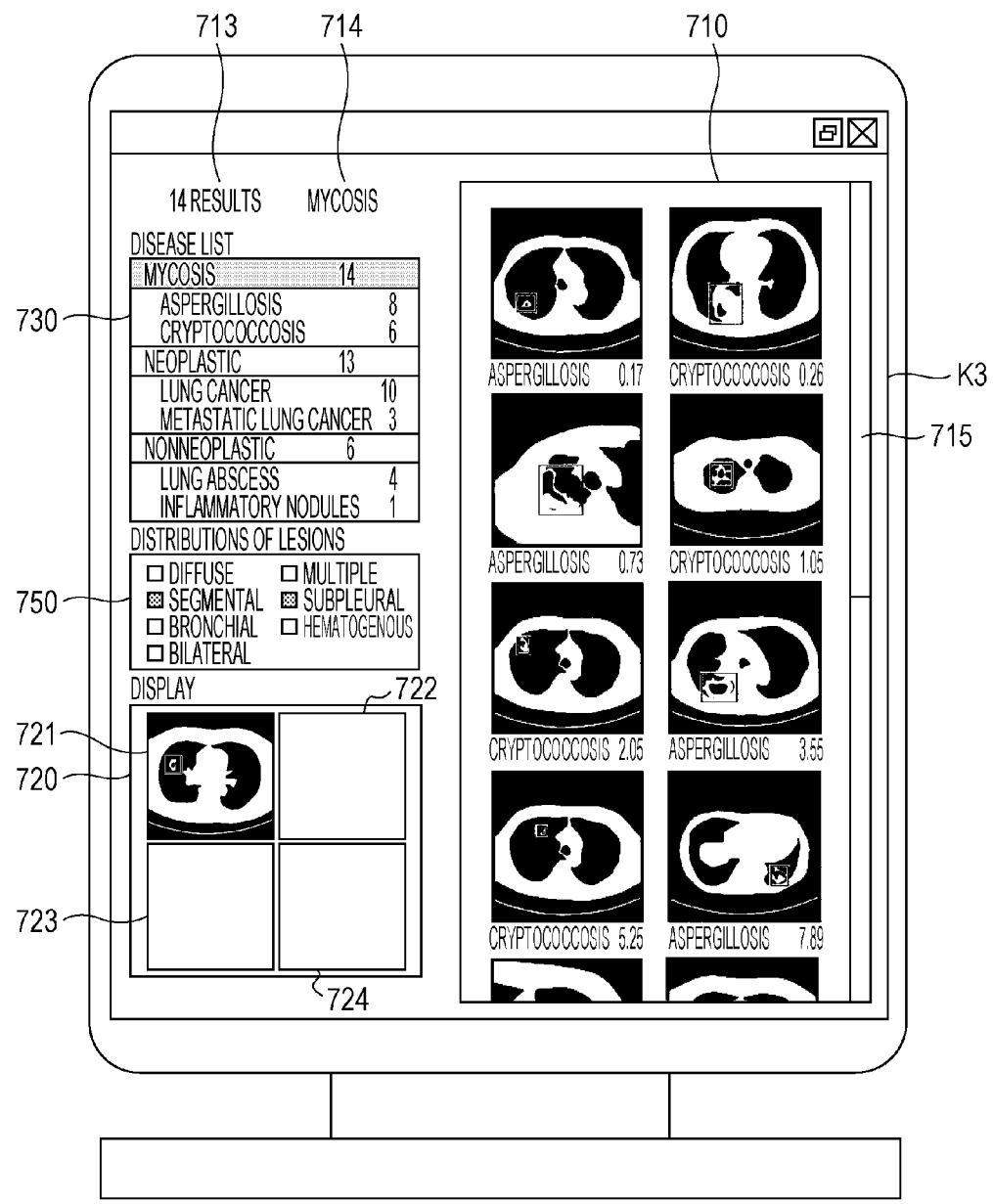
FIG. 66 is a diagram illustrating a second example of a basic screen on which one disease name is selected.

In FIG. 65, the thumbnail images of the similar cases corresponding to the disease name selected in S6000 are displayed so as to be arranged vertically in order of increasing distance. However, this embodiment is not limited to this. For example, as illustrated in FIG. 66, the thumbnail images of the similar cases corresponding to the disease name selected in S6000 may be displayed so as to be arranged horizontally in order of increasing distance. FIG. 66 is a diagram illustrating a second example of the basic screen K3 on which one disease name is selected. In the example illustrated in FIG. 66, thumbnail images of similar cases are displayed in such a manner that the similar case with the shortest distance from (or the highest similarity to) the search query image is displayed at the top end of the first column from the left and similar cases are displayed so as to be arranged from left to right in order of increasing distance (or in order of decreasing similarity), where, once the right end of the first row is reached, the next, large-distance similar case is displayed at the left end of the second row from the top.

In this case, a display style of a typical search screen on the Internet or the like is used in which similar cases having high similarity are collected in an upper portion of the case display area 710 in such a manner that search results are displayed, from left to right, in order of decreasing relevance.

The processing of S3001 to S3002 is a display process performed for the case display area 710 when a plurality of disease names are selected in the disease list display area 730.

In S3001, the display control unit 104 horizontally divides the case display area 710 into sub-areas in accordance with the number of disease names calculated in S6001. Through this process, a number of sub-areas equal to the number of disease names obtained in S6000 are created. The created sub-areas are horizontally elongated so that thumbnail images of similar cases having each of the disease names are aligned side-by-side in a row.

In S3002, the display control unit 104 displays, in each of the sub-areas created in S3001, thumbnail images of similar cases of the corresponding one of the disease names so that the thumbnail images are aligned side-by-side in a row in order of decreasing similarity.

Figure 67:
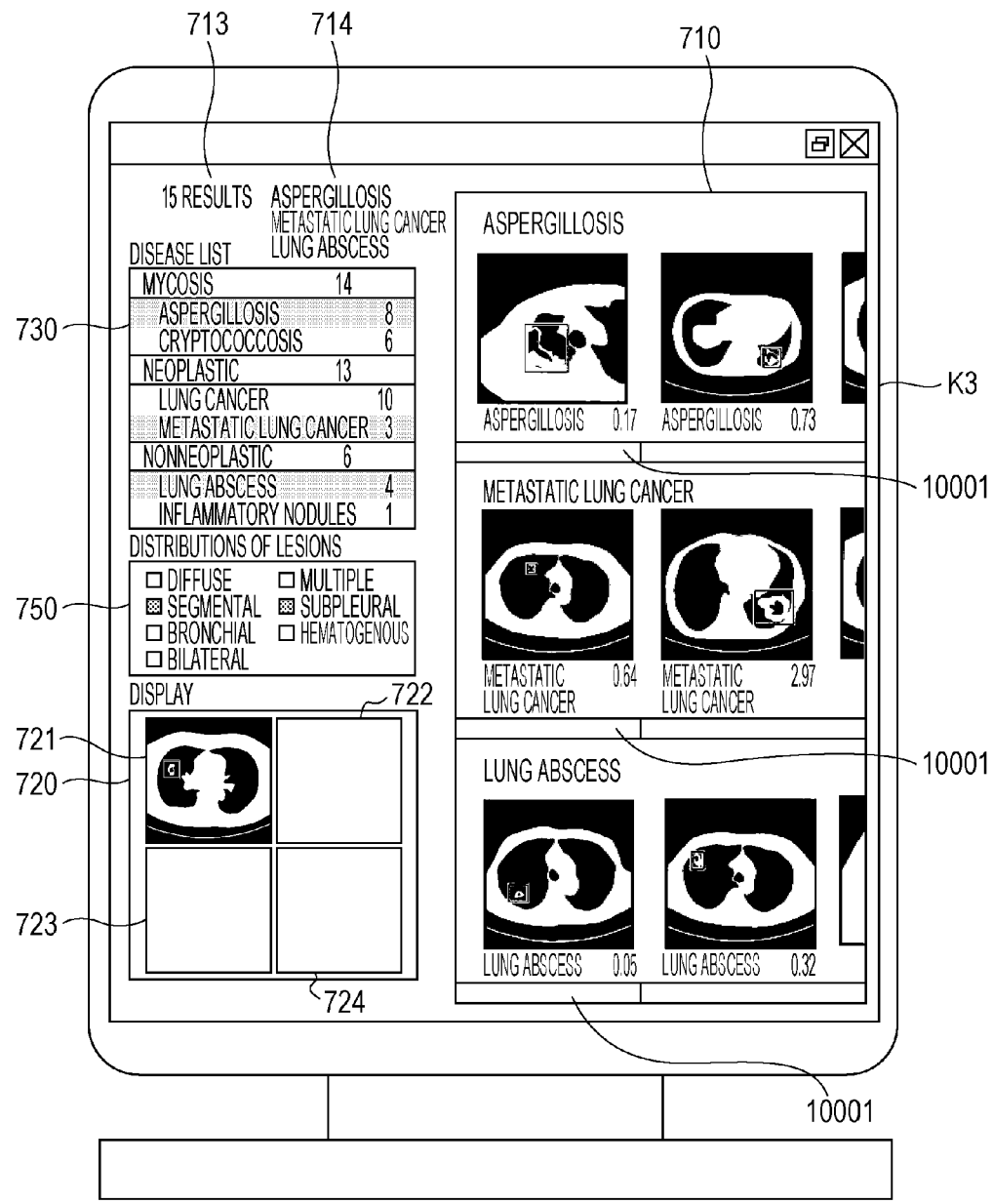
FIG. 67 is a diagram illustrating an example of a basic screen created when a plurality of disease names are selected.

FIG. 67 is a diagram illustrating an example of the basic screen K3, which is created when a plurality of disease names are selected. The illustrated basic screen K3 shows the state after three disease names, namely, aspergillosis, metastatic lung cancer, and lung abscess, are selected in the disease list display area 730 illustrated in FIG. 63. Accordingly, "aspergillosis", "metastatic lung cancer", and "lung abscess" are displayed in the display condition display area 714. Since there are 15 similar cases corresponding to the three disease names, "15 results" is displayed in the number-of-search-result display area 713. Furthermore, since the three disease names are selected, the case display area 710 is horizontally divided into three sub-areas each corresponding to one of the three disease names. In each of the sub-areas, thumbnail images of similar cases of the corresponding one of the disease names are displayed so as to be aligned side-by-side in a row in order of decreasing similarity.

In the illustrated example, three sub-areas with the headings "aspergillosis", "metastatic lung cancer", and "lung abscess", which correspond to the three disease names, are displayed in order from top to bottom. In each of the sub-areas, thumbnail images of similar cases of the corresponding one of the disease names are displayed so as to be aligned side-by-side in a row.

With the display described above, after similar cases are refined by selecting one or more disease names, the similar case having the highest similarity to each disease is displayed at the closest position to the search query image displayed in the layout area 720. This enables the physician to give priority to the study of a thumbnail image of a similar case having high similarity to the search query image. Accordingly, providing a system with efficiently improved comparison accuracy may contribute to an improvement in medical treatment accuracy.

If there are thumbnail images to be displayed in a sub-area, the number of which is greater than or equal to a certain value, and not all the thumbnail images are displayed in the sub-area at the same time, the display control unit 104 may provide the sub-area with a scrollbar 10001. In the example illustrated in FIG. 67, there are thumbnail images to be displayed in each of three sub-areas, the number of which is greater than or equal to a certain value, and not all the thumbnail images are displayed in such sub-areas at the same time. Thus, horizontal scrollbars 10001 are placed in the three sub-areas. When each of the scrollbars 10001 slides to the right, the display control unit 104 scrolls the corresponding one of the sub-areas to the left with the heading of the associated disease name or while maintaining the heading of the associated disease name in place by a distance corresponding to the amount of sliding. When each of the scrollbars 10001 slides to the left, the display control unit 104 scrolls the corresponding one of the sub-areas to the right with the heading of the associated disease name or while maintaining the heading of the associated disease name in place by a distance corresponding to the amount of sliding. This enables the user to view the thumbnail images of all the similar cases corresponding to the selected disease name. In the example illustrated in FIG. 67, up to two thumbnail images can be displayed in each sub-area at the same time. Thus, it may be sufficient that the display control unit 104 provides a sub-area with the scrollbar 10001 if there are three or more thumbnail images to be displayed in the sub-area.

Figure 68:
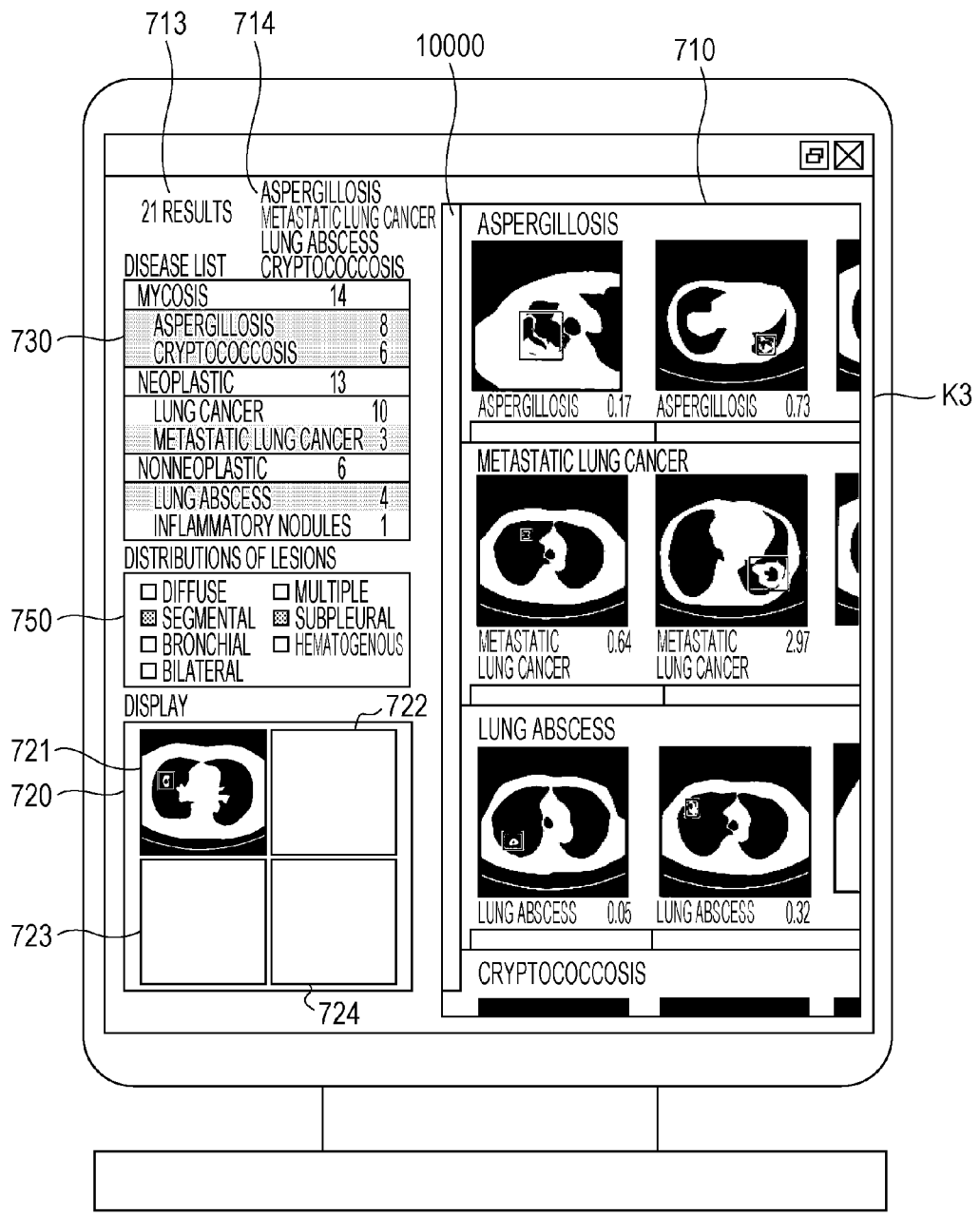
FIG. 68 is a diagram illustrating a basic screen on which the number of selected disease names is greater than or equal to a certain value.

In FIG. 67, if the number of selected disease names is greater than or equal to a certain value, as illustrated in FIG. 68, the case display area 710 may be extended using a scrollbar 10000 or the like. FIG. 68 is a diagram illustrating the basic screen K3 on which the number of selected disease names is greater than or equal to a certain value. In a case where the size of a thumbnail image to be displayed in the case display area 710 is kept at a predetermined value or more in terms of image interpretability, if the number of selected disease names is greater than or equal to a certain value, not all the selected disease names will be displayed in the case display area 710 at the same time. Accordingly, if the number of selected disease names is greater than or equal to a certain value, the display control unit 104 provides the case display area 710 with the scrollbar 10000 to substantially extend the case display area 710.

In the example illustrated in FIG. 68, the basic screen K3, which is obtained after four disease names, namely, aspergillosis, metastatic lung cancer, lung abscess, and cryptococcosis, are selected in the disease list display area 730 illustrated in FIG. 63, is illustrated. As illustrated in FIG. 68, the case display area 710 is horizontally divided into four sub-areas each corresponding to one of the four disease names, and shows, in each of the sub-areas, thumbnail images of similar cases of the corresponding one of the disease names. Part of the sub-area for cryptococcosis, which is in the fourth row from the top, is not currently visible. Accordingly, the display control unit 104 provides the case display area 710 with a vertical scrollbar 10000. When the scrollbar 10000 slides up, the display control unit 104 scrolls the case display area 710 down by a distance corresponding to the amount of sliding to make the sub-area for cryptococcosis, part of which is not currently visible, visible in the case display area 710 in its entirety. In the manner described above, in a case where the number of selected disease names is greater than or equal to a certain value, scrolling the case display area 710 with the scrollbar 10000 allows the user to view the similar cases corresponding to all the selected disease names. In the foregoing description, by way of example, the scrollbar 10000 is used. Another embodiment may be used in which, as described with reference to FIG. 50, the case display area 710 is scrolled up and down by dragging the mouse while the mouse is in the case display area 710.

In the example illustrated in FIG. 68, furthermore, the entirety of up to three sub-areas can be displayed at the same time in the case display area 710. If the user selects four or more disease names, the scrollbar 10000 is displayed.

In S3000, if one disease name is selected in the disease list display area 730, thumbnail images are displayed in the case display area 710, by way of example, so as to be arranged vertically in order of decreasing similarity. However, this embodiment is not limited to this example. For example, if one disease name is selected in the disease list display area 730, the display control unit 104 may display thumbnail images in the case display area 710 so that the thumbnail images are aligned side-by-side in a row in order of decreasing similarity.

FIG. 69 is a diagram illustrating the basic screen K3, which is obtained after aspergillosis is selected in the disease list display area 730 illustrated in FIG. 63. In the example illustrated in FIG. 69, thumbnail images of aspergillosis, which is selected as a disease name, are displayed so as to be aligned side-by-side in a row in order of decreasing similarity. The display described above enables the user to view similar cases within the same line of sight as that when a plurality of disease names are selected, improving searching usability.

In the second embodiment, the display 101b is portrait-oriented. Alternatively, the display 101b may be landscape-oriented.

Figure 53:
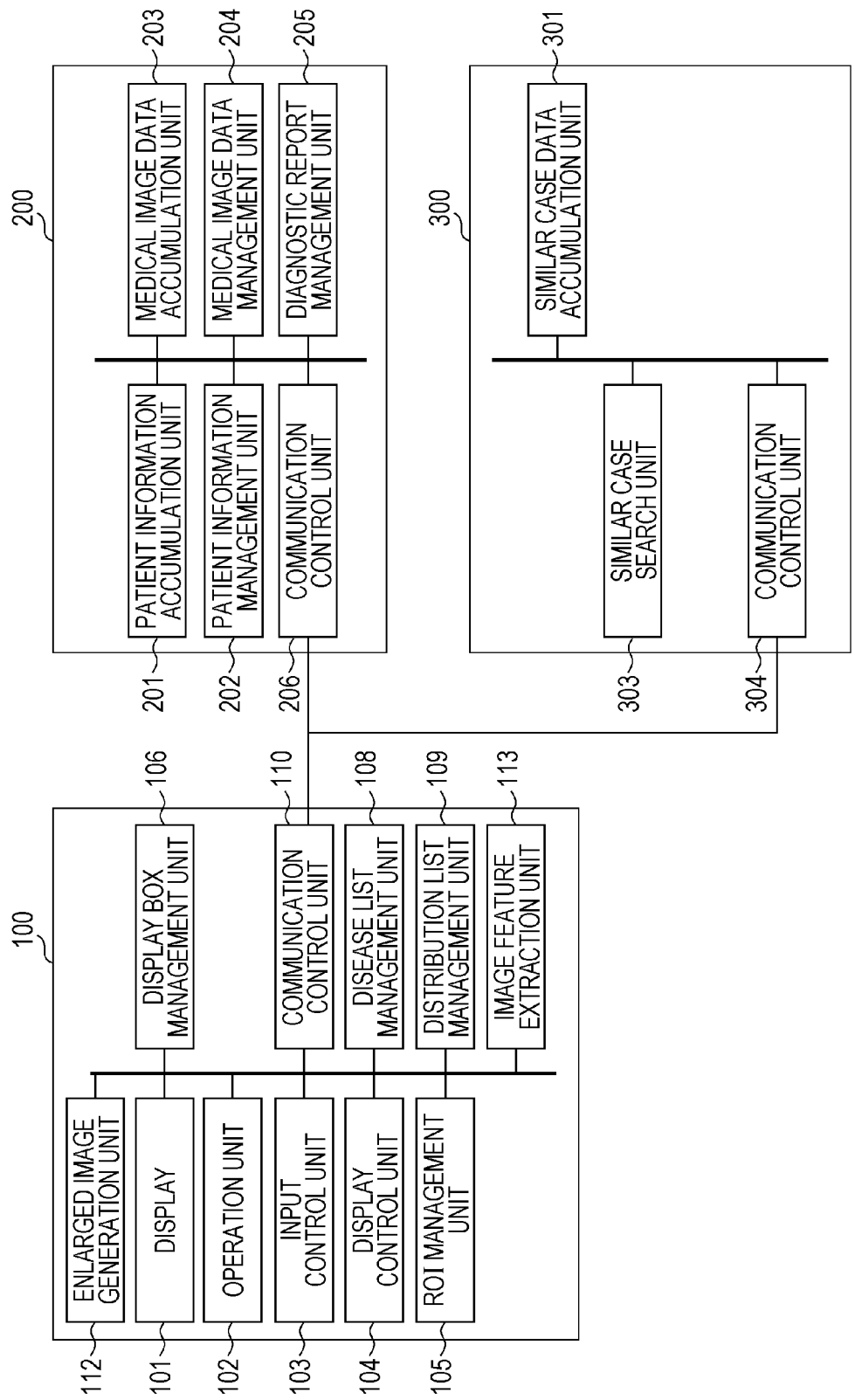
FIG. 53 is a block diagram illustrating the configuration of the information terminal, the medical information management system, and the case search system in a case where the information terminal includes an image feature extraction unit.

In FIG. 52, the image feature extraction unit 302 is included in the case search system 300. Alternatively, as illustrated in FIG. 53, the information terminal 100 may include the image feature extraction unit 302. FIG. 53 is a block diagram illustrating the configuration of the information terminal 100, the medical information management system 200, and the case search system 300 in a case where the information terminal 100 includes an image feature extraction unit. As illustrated in FIG. 53, the case search system 300 does not include an image feature extraction unit, and the information terminal 100 includes an image feature extraction unit 113. Other is substantially the same as FIG. 52.

Aspects of the present disclosure are applicable to a similar case search device that presents similar cases to be used as reference for diagnosis using medical images to be interpreted, an image interpretation training device for trainee radiologists, and the like.

What is claimed is:

1. A control method for controlling an information terminal for access to a case search system that searches for a medical image with reference to a medical image database having medical images registered therein, the information terminal including a display and a computer, wherein a target medical image is displayed on the display, the target medical image being a medical image that is a target to be interpreted and that is selected from among candidates for image interpretation, the control method comprising:
  causing the computer of the information terminal to detect first designation information indicating a region of interest in the target medical image;
  causing the computer of the information terminal to receive from the case search system, in accordance with the region of interest indicated by the first designation information, a plurality of similar medical images each having a feature value having a predetermined similarity to a feature value of the region of interest;
  causing the computer of the information terminal to display a display screen including a first display area and a second display area, the first display area being used to display the target medical image, the second display area being an area in which a certain number of images among the plurality of similar medical images are displayed so as to be arranged horizontally in order of decreasing similarity to the target medical image, the display screen further including a third display area used to select one or more disease names;
  causing the computer of the information terminal to, in response to selection of disease names using the third display area, select disease-associated similar medical images corresponding to each of the selected disease names from among the plurality of similar medical images, a total number of the selected disease names being n, n being two or more, ith selected disease-associated similar medical images corresponding to ith selected disease names, 1≤i≤n; and
  causing the computer of the information terminal, in response to selection of the disease names using the third display area, to display the selected disease-associated similar medical images in the second display area in association with the selected disease names,
  wherein the second display area is divided vertically into adjacent sub-areas, each sub-area being associated with a different one of the selected disease names, a total number of the sub-areas being n and a shape of each of the sub-areas being rectangular,
  wherein the ith selected disease-associated similar medical images are arranged in a sub-area associated with the ith selected disease name in order of decreasing similarity to the target medical image, and
  wherein the target medical image has attached information that does not include disease information, and the received plurality of similar medical images have attached information that includes disease information.

2. The control method according to claim 1, wherein the computer of the information terminal is caused to, in response to selection of a single disease name using the third display area, display disease-associated similar medical images corresponding to the selected single disease name in the second display area so that the disease-associated similar medical images are arranged horizontally in order of decreasing similarity to the target medical image.

3. The control method according to claim 1, wherein the computer of the information terminal is caused to, in response to selection of a single disease name using the third display area, display disease-associated similar medical images corresponding to the selected single disease name in the second display area so that the disease-associated similar medical images are arranged vertically in order of decreasing similarity to the target medical image.

4. The control method according to claim 1, wherein the computer of the information terminal is caused to, in response to detection of an instruction to display a disease-associated similar medical image in a sub-area among the sub-areas in enlarged form, enlarge the disease-associated similar medical images included in the sub-area with respect to corresponding regions in the disease-associated similar medical images, which correspond to the region of interest, in such a manner that display sizes of display frames within which the disease-associated similar medical images are displayed are maintained to be equal to each other.

5. The control method according to claim 4, wherein each of the received plurality of similar medical images includes second designation information indicating a corresponding region thereof which corresponds to the region of interest, and
  the computer of the information terminal is caused to, in the enlarging of the disease-associated similar medical images with respect to the corresponding regions in the disease-associated similar medical images, which correspond to the region of interest, enlarge the disease-associated similar medical images in accordance with a size of the corresponding regions indicated by the second designation information.

6. The control method according to claim 5, wherein the computer of the information terminal is caused to enlarge the disease-associated similar medical images so that, in a case where the size of the corresponding regions indicated by the second designation information is equal to a first size, the corresponding regions are enlarged a larger amount than in a case where the size of the corresponding regions indicated by the second designation information is equal to a second size larger than the first size.

7. The control method according to claim 4, wherein each of the received plurality of similar medical images includes second designation information indicating a corresponding region thereof which corresponds to the region of interest, and
  the computer of the information terminal is caused to, in enlarging of each of the plurality of similar medical images with respect to the corresponding region in the similar medical image, which corresponds to the region of interest, enlarge each of the plurality of similar medical images with an enlargement factor that makes a size of the corresponding region indicated by the second designation information have a certain ratio to the display size of the display frame within which each of the plurality of similar medical images is displayed.

8. The control method according to claim 1, further comprising:
  causing the computer of the information terminal to transmit information indicating the feature value of the region of interest to the case search system; and
  causing the computer of the information terminal to receive from the case search system a similar medical image having a feature value having the predetermined similarity to the feature value of the region of interest.

9. The control method according to claim 1, further comprising:
  causing the computer of the information terminal to transmit the target medical image and the first designation information indicating the region of interest to the case search system; and
  causing the computer of the information terminal to receive from the case search system a similar medical image having a feature value having the predetermined similarity to the feature value of the region of interest, which is obtained from the target medical image and the first designation information.

10. The control method according to claim 1, wherein the target medical image comprises a medical image of a lung,
  the similar medical image comprises a medical image of a lung,
  the first display image includes
    first distribution information for selection of a similar medical image that belongs to a predetermined first range indicating that a corresponding region of the similar medical image, which corresponds to the region of interest, is a large area of a lung,
    second distribution information for selection of a similar medical image that belongs to a predetermined second range lower than the first range, the second range indicating that a corresponding region of the similar medical image, which corresponds to the region of interest, is a portion of a lung, and
    third distribution information for selection of a similar medical image in which a corresponding region which corresponds to the region of interest includes a pleura, and
  the computer of the information terminal is caused to, in response to selection of distribution information among the first distribution information, the second distribution information, and the third distribution information, select a similar medical image corresponding to the selected distribution information from among the plurality of similar medical images and to display the selected similar medical image in the second display area.

11. The control method according to claim 10, wherein the computer of the information terminal is caused to
  in response to selection of the first distribution information, display a similar medical image corresponding to the first distribution information among the plurality of similar medical images in a display frame with an initial display size,
  in response to selection of the second distribution information, display a similar medical image corresponding to the second distribution information in a display frame in such a manner that the similar medical image is enlarged with respect to a corresponding region thereof which corresponds to the region of interest, and
  in response to selection of the third distribution information, display a similar medical image corresponding to the third distribution information in a display frame in such a manner that the similar medical image is enlarged with respect to a corresponding region thereof which corresponds to the region of interest and in such a manner that the corresponding region includes the pleura.

12. The control method according to claim 10, wherein the first distribution information comprises information indicating a distribution that belongs to a bilateral category, a multiple category, a diffuse category, or a hematogenous category,
  the second distribution information comprises information indicating a distribution that belongs to a segmental category or a bronchial category, and
  the third distribution information comprises information indicating a distribution that belongs to a subpleural category.

13. A control method for controlling an information terminal for access to a case search system that searches for a medical image with reference to a medical image database having medical images registered therein, the information terminal including a display and a computer, wherein a target medical image is displayed on the display, the target medical image being a medical image that is a target to be interpreted and that is selected from among candidates for image interpretation, the control method comprising:
  causing the computer of the information terminal to detect first designation information indicating a region of interest in the target medical image;
  causing the computer of the information terminal to receive from the case search system, in accordance with the region of interest indicated by the first designation information, a plurality of similar medical images each having a feature value having a predetermined similarity to a feature value of the region of interest;
  causing the computer of the information terminal to display a display screen including a first display area and a second display area, the first display area being used to display the target medical image, the second display area being an area in which a certain number of images among the plurality of similar medical images are displayed so as to be arranged horizontally in order of decreasing similarity to the target medical image, the display screen further including a third display area used to select one or more disease names;
  causing the computer of the information terminal to, in response to selection of disease names using the third display area, select disease-associated similar medical images corresponding to each of the selected disease names from among the plurality of similar medical images, a total number of the selected disease names being n, n being two or more, ith selected disease-associated similar medical images corresponding to ith selected disease names, $1 \leq i \leq n$; and
  causing the computer of the information terminal, in response to selection of the disease names using the third display area, to display the selected disease-associated similar medical images in the second display area in association with the selected disease names, wherein the second display area is divided vertically into adjacent sub-areas, each sub-area being associated with a different one of the selected disease names, a total number of the sub-areas being n and a shape of each of the sub-areas being rectangular, and
  wherein the ith selected disease-associated similar medical images are arranged in a sub-area associated with the ith selected disease name in order of decreasing similarity to the target medical image, and
    a similar medical image having highest similarity to the target medical image among the similar medical images displayed in the second display area is displayed at a position that is closest to the first display area,
    wherein the target medical image has attached information that does not include disease information, and the received plurality of similar medical images have attached information that includes disease information.

14. The control method according to claim 13, wherein the computer of the information terminal is caused to, in response to selection of a single disease name using the third display area, display disease-associated similar medical images corresponding to the selected single disease name in the second display area so that the disease-associated similar medical images are arranged horizontally in order of decreasing similarity to the target medical image.

15. The control method according to claim 13, wherein the computer of the information terminal is caused to, in response to selection of a single disease name using the third display area, display disease-associated similar medical images corresponding to the selected single disease name in the second display area so that the disease-associated similar medical images are arranged vertically in order of decreasing similarity to the target medical image.

16. The control method according to claim 13, further comprising:
   causing the computer of the information terminal to transmit information indicating the feature value of the region of interest to the case search system; and
   causing the computer of the information terminal to receive from the case search system a similar medical image having a feature value having the predetermined similarity to the feature value of the region of interest.

17. The control method according to claim 13, further comprising:
   causing the computer of the information terminal to transmit the target medical image and the first designation information indicating the region of interest to the case search system; and
   causing the computer of the information terminal to receive from the case search system a similar medical image having a feature value having the predetermined similarity to the feature value of the region of interest, which is obtained from the target medical image and the first designation information.

18. A control method for controlling an information terminal for access to a case search system that searches for a medical image with reference to a medical image database having medical images registered therein, the information terminal including a display and a computer, wherein a target medical image is displayed on the display, the target medical image being a medical image that is a target to be interpreted and that is selected from among candidates for image interpretation, the control method comprising:
   causing the computer of the information terminal to detect first designation information indicating a region of interest in the target medical image;
   causing the computer of the information terminal to receive from the case search system, in accordance with the region of interest indicated by the first designation information, a plurality of similar medical images each having a feature value having a predetermined similarity to a feature value of the region of interest;
   causing the computer of the information terminal to display a display screen including a first display area and a second display area, the first display area being used to display the target medical image, the second display area being an area in which a certain number of images among the plurality of similar medical images are displayed so as to be arranged vertically in order of decreasing similarity to the target medical image, the display screen further including a third display area used to select one or more disease names;
   causing the computer of the information terminal to, in response to selection of disease names using the third display area, select disease-associated similar medical images corresponding to each of the disease names from among the plurality of similar medical images, a total number of the selected disease names being n, n being two or more, ith selected disease-associated similar medical images corresponding to ith selected disease names, $1 \leq i \leq n$; and
   causing the computer of the information terminal, in response to selection of the disease names using the third display area, to display the selected disease-associated similar medical images in the second display area in association with the selected disease names, wherein the second display area is divided vertically into adjacent sub-areas, each sub-area being associated with a different one of the selected disease names, a total number of the sub-areas being n and a shape of each of the sub-areas being rectangular, and
   wherein the ith selected disease-associated similar medical images are arranged horizontally in a sub-area associated with the ith selected disease name in order of decreasing similarity to the target medical image,
   wherein a similar medical image having highest similarity to the target medical image among the similar medical images displayed in the second display area is displayed at a position that is closest to the first display area, and
   wherein the target medical image has attached information that does not include disease information, and the received plurality of similar medical images have attached information that includes disease information.

19. A non-transitory computer-readable recording medium storing a program executable by an information terminal for access to a case search system that searches for a medical image with reference to a medical image database having medical images registered therein, the information terminal including a display and a computer, wherein a target medical image is displayed on the display, the target medical image being a medical image that is a target to be interpreted and that is selected from among candidates for image interpretation, the program comprising:
   causing the computer of the information terminal to detect first designation information indicating a region of interest in the target medical image;
   causing the computer of the information terminal to receive from the case search system, in accordance with the region of interest indicated by the first designation information, a plurality of similar medical images each having a feature value having a predetermined similarity to a feature value of the region of interest;
   causing the computer of the information terminal to display a display screen including a first display area and a second display area, the first display area being used to display the target medical image, the second display area being an area in which a certain number of images among the plurality of similar medical images are displayed so as to be arranged horizontally in order of decreasing similarity to the target medical image, the display screen further including a third display area used to select one or more disease names;
   causing the computer of the information terminal to, in response to selection of disease names using the third display area, select disease-associated similar medical images corresponding to each of the selected disease names from among the plurality of similar medical images, a total number of the selected disease names being n, n being two or more, ith selected disease-associated similar medical images corresponding to ith selected disease names, $1 \leq i \leq n$; and causing the computer of the information terminal, in response to selection of the disease names using the third display area, to display the selected disease-associated similar medical images in the second display area in association with the selected disease names, wherein the second display area is divided vertically into adjacent sub-areas, each sub-area being associated with a different one of the selected disease names, a total number of the sub-areas being n and a shape of each of the sub-areas being rectangular, and wherein the ith selected disease-associated similar medical images are arranged vertically in a sub-area associated with the ith selected disease name in order of decreasing similarity to the target medical image, and wherein the target medical image has attached information that does not include disease information, and the received plurality of similar medical images have attached information that includes disease information.

20. A non-transitory computer-readable recording medium storing a program executable by an information terminal for access to a case search system that searches for a medical image with reference to a medical image database having medical images registered therein, the information terminal including a display and a computer, wherein a target medical image is displayed on the display, the target medical image being a medical image that is a target to be interpreted and that is selected from among candidates for image interpretation, the program comprising:

causing the computer of the information terminal to detect first designation information indicating a region of interest in the target medical image;

causing the computer of the information terminal to receive from the case search system, in accordance with the region of interest indicated by the first designation information, a plurality of similar medical images each having a feature value having a predetermined similarity to a feature value of the region of interest;

causing the computer of the information terminal to display a display screen including a first display area and a second display area, the first display area being used to display the target medical image, the second display area being an area in which a certain number of images among the plurality of similar medical images are displayed so as to be arranged horizontally in order of decreasing similarity to the target medical image, the display screen further including a third display area used to select one or more disease names;

causing the computer of the information terminal to, in response to selection of disease names using the third display area, select disease-associated similar medical images corresponding to each of the selected disease names from among the plurality of similar medical images, a total number of the selected disease names being n, n being two or more, ith selected disease associated similar medical images corresponding to ith selected disease names, 1≤i≤n; and causing the computer of the information terminal, in response to selection of the disease names using the third display area, to display the selected disease-associated similar medical images in the second display area in association with the selected disease names, wherein the second display area is divided vertically into adjacent sub-areas, each sub-area being associated with a different one of the selected disease name, a total number of the sub-areas being n and a shape of each of the sub-areas being rectangular, and wherein the ith selected disease-associated similar medical images are arranged horizontally in a sub-area associated with the ith selected disease name in order of decreasing similarity to the target medical image, wherein a similar medical image having highest similarity to the target medical image among the similar medical images displayed in the second display area is displayed at a position that is closest to the first display area, and wherein the target medical image has attached information that does not include disease information, and the received plurality of similar medical images have attached information that includes disease information.

21. A non-transitory computer-readable recording medium storing a program executable by an information terminal for access to a case search system that searches for a medical image with reference to a medical image database having medical images registered therein, the information terminal including a display and a computer, wherein a target medical image is displayed on the display, the target medical image being a medical image that is a target to be interpreted and that is selected from among candidates for image interpretation, the program comprising:

causing the computer of the information terminal to detect first designation information indicating a region of interest in the target medical image;

causing the computer of the information terminal to receive from the case search system, in accordance with the region of interest indicated by the first designation information, a plurality of similar medical images each having a feature value having a predetermined similarity to a feature value of the region of interest;

causing the computer of the information terminal to display a display screen including a first display area and a second display area, the first display area being used to display the target medical image, the second display area being an area in which a certain number of images among the plurality of similar medical images are displayed so as to be arranged vertically in order of decreasing similarity to the target medical image, the display screen further including a third display area used to select one or more disease names;

causing the computer of the information terminal to, in response to selection of disease names using the third display area, select disease-associated similar medical images corresponding to each of the selected disease names from among the plurality of similar medical images, a total number of the selected disease names being n, n being two or more, ith selected disease-associated similar medical images corresponding to ith selected disease names, 1≤i≤n; and causing the computer of the information terminal, in response to selection of the disease names using the third display area, to display the selected disease-associated similar medical images in the second display area in association with the selected disease names, wherein the second display area is divided vertically into adjacent sub-areas, each sub-area being associated with a different one of the selected disease names, a total number of the sub-areas being n and a shape of each of the sub-areas being rectangular, and wherein the ith selected disease-associated similar medical images are arranged horizontally in a sub-area associated with the ith selected disease name in order of decreasing similarity to the target medical image, wherein a similar medical image having highest similarity to the target medical image among the similar medical images displayed in the second display area is displayed at a position that is closest to the first display area, and wherein the target medical image has attached information that does not include disease information, and the received plurality of similar medical images have attached information that includes disease information.

\* \* \* \* \*